(12) United States Patent
Peck et al.

(10) Patent No.: US 11,550,939 B2
(45) Date of Patent: Jan. 10, 2023

(54) NUCLEIC ACID BASED DATA STORAGE USING ENZYMATIC BIOENCRYPTION

(71) Applicant: TWIST BIOSCIENCE CORPORATION, South San Francisco, CA (US)

(72) Inventors: Bill James Peck, Santa Clara, CA (US); Ramsey Ibrahim Zeitoun, San Francisco, CA (US)

(73) Assignee: TWIST BIOSCIENCE CORPORATION, South San Francisco, CA (US)

( * ) Notice: Subject to any disclaimer, the term of this patent is extended or adjusted under 35 U.S.C. 154(b) by 1110 days.

(21) Appl. No.: 15/902,855

(22) Filed: Feb. 22, 2018

(65) Prior Publication Data

US 2018/0253563 A1 Sep. 6, 2018

Related U.S. Application Data

(60) Provisional application No. 62/462,284, filed on Feb. 22, 2017.

(51) Int. Cl.
  *G06F 21/62* (2013.01)
  *H04L 9/32* (2006.01)
  *G16B 50/00* (2019.01)
  *G16B 50/40* (2019.01)
  *G16B 50/30* (2019.01)

(52) U.S. Cl.
  CPC ......... *G06F 21/6218* (2013.01); *G16B 50/00* (2019.02); *G16B 50/30* (2019.02); *G16B 50/40* (2019.02); *H04L 9/3231* (2013.01)

(58) Field of Classification Search
  None
  See application file for complete search history.

(56) References Cited

U.S. PATENT DOCUMENTS

| | | |
|---|---|---|
| 3,549,368 A | 12/1970 | Robert et al. |
| 3,920,714 A | 11/1975 | Streck |
| 4,123,661 A | 10/1978 | Wolf et al. |
| 4,415,732 A | 11/1983 | Caruthers et al. |
| 4,613,398 A | 9/1986 | Chiong et al. |
| 4,726,877 A | 2/1988 | Fryd et al. |
| 4,808,511 A | 2/1989 | Holmes |
| 4,837,401 A | 6/1989 | Hirose et al. |
| 4,863,557 A | 9/1989 | Kokaku et al. |
| 4,981,797 A | 1/1991 | Jessee et al. |
| 4,988,617 A | 1/1991 | Landegren et al. |
| 5,102,797 A | 4/1992 | Tucker et al. |
| 5,118,605 A | 6/1992 | Urdea |
| 5,137,814 A | 8/1992 | Rashtchian et al. |
| 5,143,854 A | 9/1992 | Pirrung et al. |
| 5,242,794 A | 9/1993 | Whiteley et al. |
| 5,242,974 A | 9/1993 | Holmes |
| 5,288,514 A | 2/1994 | Ellman |
| 5,299,491 A | 4/1994 | Kawada |
| 5,368,823 A | 11/1994 | McGraw et al. |
| 5,384,261 A | 1/1995 | Winkler et al. |
| 5,387,541 A | 2/1995 | Hodge et al. |
| 5,395,753 A | 3/1995 | Prakash |
| 5,431,720 A | 7/1995 | Nagai et al. |
| 5,445,934 A | 8/1995 | Fodor et al. |
| 5,449,754 A | 9/1995 | Nishioka |
| 5,459,039 A | 10/1995 | Modrich et al. |
| 5,474,796 A | 12/1995 | Brennan |
| 5,476,930 A | 12/1995 | Letsinger et al. |
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |
| 5,510,270 A | 4/1996 | Fodor et al. |
| 5,514,789 A | 5/1996 | Kempe |
| 5,527,681 A | 6/1996 | Holmes |
| 5,530,516 A | 6/1996 | Sheets |
| 5,534,507 A | 7/1996 | Cama et al. |
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |
| 5,679,522 A | 10/1997 | Modrich et al. |
| 5,683,879 A | 11/1997 | Laney et al. |
| 5,688,642 A | 11/1997 | Chrisey et al. |

(Continued)

FOREIGN PATENT DOCUMENTS

| | | |
|---|---|---|
| AU | 3157000 A | 9/2000 |
| CA | 2362939 A1 | 8/2000 |

(Continued)

OTHER PUBLICATIONS

Wikipedia, "Central dogma of molecular biology," URL: https://en.wikipedia.org/wiki/Central_dogma_of_molecular_biology, 9 pages, downloaded Dec. 4, 2021.*
Hood, Leroy, and David Galas. "The digital code of DNA." Nature 421.6921 (2003): 444-448.*
Alberts et al.: Molecular Biology of the Cell. 4th edition. New York: Garland Science; 2002. The Generation of Antibody Diversity. https://www.ncbi.nlm.nih.gov/books/NBK26860/.
Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.
Bai. A Novel Human scFv Library with Non-Combinatorial Synthetic CDR Diversity. PLoS One. 10(10):1-18 (2015).
Berg: Biochemistry. 5th ED. New York (2002) 148-149.

(Continued)

*Primary Examiner* — G Steven Vanni
(74) *Attorney, Agent, or Firm* — Wilson Sonsini Goodrich & Rosati

(57) ABSTRACT

Provided herein are compositions, devices, systems and methods for the generation and use of secured biomolecule-based information for storage. Further described herein are compositions, devices, systems and methods for bioencryption or biodecryption of information. Conversion of a digital sequence to a nucleic based sequence includes a step of selection of one or more bioencryption methods.

13 Claims, 21 Drawing Sheets

Specification includes a Sequence Listing.

(56) References Cited

U.S. PATENT DOCUMENTS

| | | | |
|---|---|---|---|
| 5,700,637 | A | 12/1997 | Southern |
| 5,700,642 | A | 12/1997 | Monforte et al. |
| 5,702,894 | A | 12/1997 | Modrich et al. |
| 5,707,806 | A | 1/1998 | Shuber |
| 5,712,124 | A | 1/1998 | Walker |
| 5,712,126 | A | 1/1998 | Weissman et al. |
| 5,739,386 | A | 4/1998 | Holmes |
| 5,750,672 | A | 5/1998 | Kempe |
| 5,780,613 | A | 7/1998 | Letsinger et al. |
| 5,830,643 | A | 11/1998 | Yamamoto et al. |
| 5,830,655 | A | 11/1998 | Monforte et al. |
| 5,830,662 | A | 11/1998 | Soares et al. |
| 5,834,252 | A | 11/1998 | Stemmer et al. |
| 5,843,669 | A | 12/1998 | Kaiser et al. |
| 5,843,767 | A | 12/1998 | Beattie |
| 5,846,717 | A | 12/1998 | Brow et al. |
| 5,854,033 | A | 12/1998 | Lizardi |
| 5,858,754 | A | 1/1999 | Modrich et al. |
| 5,861,482 | A | 1/1999 | Modrich et al. |
| 5,863,801 | A | 1/1999 | Southgate et al. |
| 5,869,245 | A | 2/1999 | Yeung |
| 5,877,280 | A | 3/1999 | Wetmur |
| 5,882,496 | A | 3/1999 | Northrup et al. |
| 5,922,539 | A | 7/1999 | Modrich et al. |
| 5,922,593 | A | 7/1999 | Livingston |
| 5,928,907 | A | 7/1999 | Woudenberg et al. |
| 5,962,272 | A | 10/1999 | Chenchik et al. |
| 5,976,842 | A | 11/1999 | Wurst |
| 5,976,846 | A | 11/1999 | Passmore et al. |
| 5,989,872 | A | 11/1999 | Luo et al. |
| 5,994,069 | A | 11/1999 | Hall et al. |
| 6,001,567 | A | 12/1999 | Brow et al. |
| 6,008,031 | A | 12/1999 | Modrich et al. |
| 6,013,440 | A | 1/2000 | Lipshutz et al. |
| 6,015,674 | A | 1/2000 | Woudenberg et al. |
| 6,017,434 | A | 1/2000 | Simpson et al. |
| 6,020,481 | A | 2/2000 | Benson et al. |
| 6,027,898 | A | 2/2000 | Gjerde et al. |
| 6,028,189 | A | 2/2000 | Blanchard |
| 6,028,198 | A | 2/2000 | Liu et al. |
| 6,040,138 | A | 3/2000 | Lockhart et al. |
| 6,077,674 | A | 6/2000 | Schleifer et al. |
| 6,087,482 | A | 7/2000 | Teng et al. |
| 6,090,543 | A | 7/2000 | Prudent et al. |
| 6,090,606 | A | 7/2000 | Kaiser et al. |
| 6,103,474 | A | 8/2000 | Dellinger et al. |
| 6,107,038 | A | 8/2000 | Choudhary et al. |
| 6,110,682 | A | 8/2000 | Dellinger et al. |
| 6,114,115 | A | 9/2000 | Wagner, Jr. |
| 6,130,045 | A | 10/2000 | Wurst et al. |
| 6,132,997 | A | 10/2000 | Shannon |
| 6,136,568 | A | 10/2000 | Hiatt et al. |
| 6,171,797 | B1 | 1/2001 | Perbost |
| 6,180,351 | B1 | 1/2001 | Cattell |
| 6,201,112 | B1 | 3/2001 | Ach |
| 6,218,118 | B1 | 4/2001 | Sampson et al. |
| 6,221,653 | B1 | 4/2001 | Caren et al. |
| 6,222,030 | B1 | 4/2001 | Dellinger et al. |
| 6,232,072 | B1 | 5/2001 | Fisher |
| 6,235,483 | B1 | 5/2001 | Wolber et al. |
| 6,242,266 | B1 | 6/2001 | Schleifer et al. |
| 6,251,588 | B1 | 6/2001 | Shannon et al. |
| 6,251,595 | B1 | 6/2001 | Gordon et al. |
| 6,251,685 | B1 | 6/2001 | Dorsel et al. |
| 6,258,454 | B1 | 7/2001 | Lefkowitz et al. |
| 6,262,490 | B1 | 7/2001 | Hsu et al. |
| 6,274,725 | B1 | 8/2001 | Sanghvi et al. |
| 6,284,465 | B1 | 9/2001 | Wolber |
| 6,287,776 | B1 | 9/2001 | Hefti |
| 6,287,824 | B1 | 9/2001 | Lizardi |
| 6,297,017 | B1 | 10/2001 | Schmidt et al. |
| 6,300,137 | B1 | 10/2001 | Earhart et al. |
| 6,306,599 | B1 | 10/2001 | Perbost |
| 6,309,822 | B1 | 10/2001 | Fodor et al. |
| 6,309,828 | B1 | 10/2001 | Schleifer et al. |
| 6,312,911 | B1 | 11/2001 | Bancroft et al. |
| 6,319,674 | B1 | 11/2001 | Fulcrand et al. |
| 6,323,043 | B1 | 11/2001 | Caren et al. |
| 6,329,210 | B1 | 12/2001 | Schleifer |
| 6,346,423 | B1 | 2/2002 | Schembri |
| 6,365,355 | B1 | 4/2002 | McCutchen-Maloney |
| 6,372,483 | B2 | 4/2002 | Schleifer et al. |
| 6,375,903 | B1 | 4/2002 | Cerrina et al. |
| 6,376,285 | B1 | 4/2002 | Joyner et al. |
| 6,384,210 | B1 | 5/2002 | Blanchard |
| 6,387,636 | B1 | 5/2002 | Perbost et al. |
| 6,399,394 | B1 | 6/2002 | Dahm et al. |
| 6,399,516 | B1 | 6/2002 | Ayon |
| 6,403,314 | B1 | 6/2002 | Lange et al. |
| 6,406,849 | B1 | 6/2002 | Dorsel et al. |
| 6,406,851 | B1 | 6/2002 | Bass |
| 6,408,308 | B1 | 6/2002 | Maslyn et al. |
| 6,419,883 | B1 | 7/2002 | Blanchard |
| 6,428,957 | B1 | 8/2002 | Delenstarr |
| 6,440,669 | B1 | 8/2002 | Bass et al. |
| 6,444,268 | B2 | 9/2002 | Lefkowitz et al. |
| 6,446,642 | B1 | 9/2002 | Caren et al. |
| 6,446,682 | B1 | 9/2002 | Viken |
| 6,451,998 | B1 | 9/2002 | Perbost |
| 6,458,526 | B1 | 10/2002 | Schembri et al. |
| 6,458,535 | B1 | 10/2002 | Hall et al. |
| 6,458,583 | B1 | 10/2002 | Bruhn et al. |
| 6,461,812 | B2 | 10/2002 | Barth et al. |
| 6,461,816 | B1 | 10/2002 | Wolber et al. |
| 6,469,156 | B1 | 10/2002 | Schafer et al. |
| 6,472,147 | B1 | 10/2002 | Janda et al. |
| 6,492,107 | B1 | 12/2002 | Kauffman et al. |
| 6,518,056 | B2 | 2/2003 | Schembri et al. |
| 6,521,427 | B1 | 2/2003 | Evans |
| 6,521,453 | B1 | 2/2003 | Crameri et al. |
| 6,555,357 | B1 | 4/2003 | Kaiser et al. |
| 6,558,908 | B2 | 5/2003 | Wolber et al. |
| 6,562,611 | B1 | 5/2003 | Kaiser et al. |
| 6,566,495 | B1 | 5/2003 | Fodor et al. |
| 6,582,908 | B2 | 6/2003 | Fodor et al. |
| 6,582,938 | B1 | 6/2003 | Su et al. |
| 6,586,211 | B1 | 7/2003 | Staehler et al. |
| 6,587,579 | B1 | 7/2003 | Bass |
| 6,589,739 | B2 | 7/2003 | Fisher |
| 6,599,693 | B1 | 7/2003 | Webb |
| 6,602,472 | B1 | 8/2003 | Zimmermann et al. |
| 6,610,978 | B2 | 8/2003 | Yin et al. |
| 6,613,513 | B1 | 9/2003 | Parce et al. |
| 6,613,523 | B2 | 9/2003 | Fischer |
| 6,613,560 | B1 | 9/2003 | Tso et al. |
| 6,613,893 | B1 | 9/2003 | Webb |
| 6,621,076 | B1 | 9/2003 | Van De Goor et al. |
| 6,630,581 | B2 | 10/2003 | Dellinger et al. |
| 6,632,641 | B1 | 10/2003 | Brennan et al. |
| 6,635,226 | B1 | 10/2003 | Tso et al. |
| 6,642,373 | B2 | 11/2003 | Manoharan et al. |
| 6,649,348 | B2 | 11/2003 | Bass et al. |
| 6,660,338 | B1 | 12/2003 | Hargreaves |
| 6,664,112 | B2 | 12/2003 | Mulligan et al. |
| 6,670,127 | B2 | 12/2003 | Evans |
| 6,670,461 | B1 | 12/2003 | Nielsen et al. |
| 6,673,552 | B2 | 1/2004 | Frey |
| 6,682,702 | B2 | 1/2004 | Barth et al. |
| 6,689,319 | B1 | 2/2004 | Fisher et al. |
| 6,692,917 | B2 | 2/2004 | Neri et al. |
| 6,702,256 | B2 | 3/2004 | Killeen et al. |
| 6,706,471 | B1 | 3/2004 | Brow et al. |
| 6,706,875 | B1 | 3/2004 | Goldberg et al. |
| 6,709,841 | B2 | 3/2004 | Short |
| 6,709,852 | B1 | 3/2004 | Bloom et al. |
| 6,709,854 | B2 | 3/2004 | Donahue et al. |
| 6,713,262 | B2 | 3/2004 | Gellibolian et al. |
| 6,716,629 | B2 | 4/2004 | Hess et al. |
| 6,716,634 | B1 | 4/2004 | Myerson |
| 6,723,509 | B2 | 4/2004 | Ach |
| 6,728,129 | B2 | 4/2004 | Lindsey et al. |
| 6,743,585 | B2 | 6/2004 | Dellinger et al. |
| 6,753,145 | B2 | 6/2004 | Holcomb et al. |
| 6,768,005 | B2 | 7/2004 | Mellor et al. |

(56) References Cited

U.S. PATENT DOCUMENTS

| | | |
|---|---|---|
| 6,770,748 B2 | 8/2004 | Imanishi et al. |
| 6,770,892 B2 | 8/2004 | Corson et al. |
| 6,773,676 B2 | 8/2004 | Schembri |
| 6,773,888 B2 | 8/2004 | Li et al. |
| 6,780,982 B2 | 8/2004 | Lyamichev et al. |
| 6,787,308 B2 | 9/2004 | Balasubramanian et al. |
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | McGall et al. |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,846,922 B1 | 1/2005 | Manoharan et al. |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | Van De Goor et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,951,719 B1 | 10/2005 | Dupret et al. |
| 6,958,119 B1 | 10/2005 | Yin et al. |
| 6,960,464 B2 | 11/2005 | Jessee et al. |
| 6,969,449 B2 | 11/2005 | Maher et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 6,991,922 B2 | 1/2006 | Dupret et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,041,445 B2 | 5/2006 | Chenchik et al. |
| 7,045,289 B2 | 5/2006 | Allawi et al. |
| 7,051,574 B2 | 5/2006 | Peck |
| 7,052,841 B2 | 5/2006 | Delenstarr |
| 7,062,385 B2 | 6/2006 | White et al. |
| 7,064,197 B1 | 6/2006 | Rabbani et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 | 7/2006 | Bass et al. |
| 7,094,537 B2 | 8/2006 | Leproust et al. |
| 7,097,974 B1 | 8/2006 | Staehler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,122,364 B1 | 10/2006 | Lyamichev et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,150,982 B2 | 12/2006 | Allawi et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,183,406 B2 | 2/2007 | Belshaw et al. |
| 7,192,710 B2 | 3/2007 | Gellibolian et al. |
| 7,193,077 B2 | 3/2007 | Dellinger et al. |
| 7,195,872 B2 | 3/2007 | Agrawal et al. |
| 7,198,939 B2 | 4/2007 | Dorsel et al. |
| 7,202,264 B2 | 4/2007 | Ravikumar et al. |
| 7,202,358 B2 | 4/2007 | Hargreaves |
| 7,205,128 B2 | 4/2007 | Ilsley et al. |
| 7,205,399 B1 | 4/2007 | Vargeese et al. |
| 7,205,400 B2 | 4/2007 | Webb |
| 7,206,439 B2 | 4/2007 | Zhou et al. |
| 7,208,322 B2 | 4/2007 | Stolowitz et al. |
| 7,217,522 B2 | 5/2007 | Brenner |
| 7,220,573 B2 | 5/2007 | Shea et al. |
| 7,221,785 B2 | 5/2007 | Curry et al. |
| 7,226,862 B2 | 6/2007 | Staehler et al. |
| 7,227,017 B2 | 6/2007 | Mellor et al. |
| 7,229,497 B2 | 6/2007 | Stott et al. |
| 7,247,337 B1 | 7/2007 | Leproust et al. |
| 7,247,497 B2 | 7/2007 | Dahm et al. |
| 7,252,938 B2 | 8/2007 | Leproust et al. |
| 7,269,518 B2 | 9/2007 | Corson |
| 7,271,258 B2 | 9/2007 | Dellinger et al. |
| 7,276,336 B1 | 10/2007 | Webb et al. |
| 7,276,378 B2 | 10/2007 | Myerson |
| 7,276,599 B2 | 10/2007 | Moore et al. |
| 7,282,183 B2 | 10/2007 | Peck |
| 7,282,332 B2 | 10/2007 | Caren et al. |
| 7,282,705 B2 | 10/2007 | Brennen |
| 7,291,471 B2 | 11/2007 | Sampson et al. |
| 7,302,348 B2 | 11/2007 | Ghosh et al. |
| 7,306,917 B2 | 12/2007 | Prudent et al. |
| 7,314,599 B2 | 1/2008 | Roitman et al. |
| 7,323,320 B2 | 1/2008 | Oleinikov |
| 7,344,831 B2 | 3/2008 | Wolber et al. |
| 7,348,144 B2 | 3/2008 | Minor |
| 7,351,379 B2 | 4/2008 | Schleifer |
| 7,353,116 B2 | 4/2008 | Webb et al. |
| 7,361,906 B2 | 4/2008 | Ghosh et al. |
| 7,364,896 B2 | 4/2008 | Schembri |
| 7,368,550 B2 | 5/2008 | Dellinger et al. |
| 7,371,348 B2 | 5/2008 | Schleifer et al. |
| 7,371,519 B2 | 5/2008 | Wolber et al. |
| 7,371,580 B2 | 5/2008 | Yakhini et al. |
| 7,372,982 B2 | 5/2008 | Le Cocq |
| 7,384,746 B2 | 6/2008 | Lyamichev et al. |
| 7,385,050 B2 | 6/2008 | Dellinger et al. |
| 7,390,457 B2 | 6/2008 | Schembri |
| 7,393,665 B2 | 7/2008 | Brenner |
| 7,396,676 B2 | 7/2008 | Robotti et al. |
| 7,399,844 B2 | 7/2008 | Sampson et al. |
| 7,402,279 B2 | 7/2008 | Schembri |
| 7,411,061 B2 | 8/2008 | Myerson et al. |
| 7,413,709 B2 | 8/2008 | Roitman et al. |
| 7,417,139 B2 | 8/2008 | Dellinger et al. |
| 7,422,911 B2 | 9/2008 | Schembri |
| 7,427,679 B2 | 9/2008 | Dellinger et al. |

(56) References Cited

U.S. PATENT DOCUMENTS

| | | |
|---|---|---|
| 7,432,048 B2 | 10/2008 | Neri et al. |
| 7,435,810 B2 | 10/2008 | Myerson et al. |
| 7,439,272 B2 | 10/2008 | Xu |
| 7,476,709 B2 | 1/2009 | Moody et al. |
| 7,482,118 B2 | 1/2009 | Allawi et al. |
| 7,488,607 B2 | 2/2009 | Tom-Moy et al. |
| 7,504,213 B2 | 3/2009 | Sana et al. |
| 7,514,369 B2 | 4/2009 | Li et al. |
| 7,517,979 B2 | 4/2009 | Wolber |
| 7,524,942 B2 | 4/2009 | Wang et al. |
| 7,524,950 B2 | 4/2009 | Dellinger |
| 7,527,928 B2 | 5/2009 | Neri et al. |
| 7,531,303 B2 | 5/2009 | Dorsel et al. |
| 7,534,561 B2 | 5/2009 | Sana et al. |
| 7,534,563 B2 | 5/2009 | Hargreaves |
| 7,537,936 B2 | 5/2009 | Dahm et al. |
| 7,541,145 B2 | 6/2009 | Prudent et al. |
| 7,544,473 B2 | 6/2009 | Brenner |
| 7,556,919 B2 | 7/2009 | Chenchik et al. |
| 7,563,600 B2 | 7/2009 | Oleinikov |
| 7,572,585 B2 | 8/2009 | Wang |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,588,889 B2 | 9/2009 | Wolber et al. |
| 7,595,350 B2 | 9/2009 | Xu |
| 7,604,941 B2 | 10/2009 | Jacobson |
| 7,604,996 B1 | 10/2009 | Stuelpnagel et al. |
| 7,608,396 B2 | 10/2009 | Delenstarr |
| 7,618,777 B2 | 11/2009 | Myerson et al. |
| 7,629,120 B2 | 12/2009 | Bennett et al. |
| 7,635,772 B2 | 12/2009 | McCormac |
| 7,648,832 B2 | 1/2010 | Jessee et al. |
| 7,651,762 B2 | 1/2010 | Xu et al. |
| 7,659,069 B2 | 2/2010 | Belyaev et al. |
| 7,678,542 B2 | 3/2010 | Lyamichev et al. |
| 7,682,809 B2 | 3/2010 | Sampson |
| 7,709,197 B2 | 5/2010 | Drmanac |
| 7,718,365 B2 | 5/2010 | Wang |
| 7,718,786 B2 | 5/2010 | Dupret et al. |
| 7,723,077 B2 | 5/2010 | Young et al. |
| 7,737,088 B1 | 6/2010 | Staehler et al. |
| 7,737,089 B2 | 6/2010 | Guimil et al. |
| 7,741,463 B2 | 6/2010 | Gormley et al. |
| 7,749,701 B2 | 7/2010 | Leproust et al. |
| 7,759,471 B2 | 7/2010 | Dellinger et al. |
| 7,776,021 B2 | 8/2010 | Borenstein et al. |
| 7,776,532 B2 | 8/2010 | Gibson et al. |
| 7,790,369 B2 | 9/2010 | Stahler et al. |
| 7,790,387 B2 | 9/2010 | Dellinger et al. |
| 7,807,356 B2 | 10/2010 | Sampson et al. |
| 7,807,806 B2 | 10/2010 | Allawi et al. |
| 7,811,753 B2 | 10/2010 | Eshoo |
| 7,816,079 B2 | 10/2010 | Fischer |
| 7,820,387 B2 | 10/2010 | Neri et al. |
| 7,829,314 B2 | 11/2010 | Prudent et al. |
| 7,855,281 B2 | 12/2010 | Dellinger et al. |
| 7,862,999 B2 | 1/2011 | Zheng et al. |
| 7,867,782 B2 | 1/2011 | Barth |
| 7,875,463 B2 | 1/2011 | Adaskin et al. |
| 7,879,541 B2 | 2/2011 | Kincaid |
| 7,879,580 B2 | 2/2011 | Carr et al. |
| 7,894,998 B2 | 2/2011 | Kincaid |
| 7,919,239 B2 | 4/2011 | Wang |
| 7,919,308 B2 | 4/2011 | Schleifer |
| 7,927,797 B2 | 4/2011 | Nobile et al. |
| 7,927,838 B2 | 4/2011 | Shannon |
| 7,932,025 B2 | 4/2011 | Carr et al. |
| 7,932,070 B2 | 4/2011 | Hogrefe et al. |
| 7,935,800 B2 | 5/2011 | Allawi et al. |
| 7,939,645 B2 | 5/2011 | Borns |
| 7,943,046 B2 | 5/2011 | Martosella et al. |
| 7,943,358 B2 | 5/2011 | Hogrefe et al. |
| 7,960,157 B2 | 6/2011 | Borns |
| 7,977,119 B2 | 7/2011 | Kronick et al. |
| 7,979,215 B2 | 7/2011 | Sampas |
| 7,998,437 B2 | 8/2011 | Berndt et al. |
| 7,999,087 B2 | 8/2011 | Dellinger et al. |
| 8,021,842 B2 | 9/2011 | Brenner |
| 8,021,844 B2 | 9/2011 | Wang |
| 8,034,917 B2 | 10/2011 | Yamada |
| 8,036,835 B2 | 10/2011 | Sampas et al. |
| 8,048,664 B2 | 11/2011 | Guan et al. |
| 8,053,191 B2 | 11/2011 | Blake |
| 8,058,001 B2 | 11/2011 | Crameri et al. |
| 8,058,004 B2 | 11/2011 | Oleinikov |
| 8,058,055 B2 | 11/2011 | Barrett et al. |
| 8,063,184 B2 | 11/2011 | Allawi et al. |
| 8,067,556 B2 | 11/2011 | Hogrefe et al. |
| 8,073,626 B2 | 12/2011 | Troup et al. |
| 8,076,064 B2 | 12/2011 | Wang |
| 8,076,152 B2 | 12/2011 | Robotti |
| 8,097,711 B2 | 1/2012 | Timar et al. |
| 8,137,936 B2 | 3/2012 | MacEvicz |
| 8,148,068 B2 | 4/2012 | Brenner |
| 8,154,729 B2 | 4/2012 | Baldo et al. |
| 8,168,385 B2 | 5/2012 | Brenner |
| 8,168,388 B2 | 5/2012 | Gormley et al. |
| 8,173,368 B2 | 5/2012 | Staehler et al. |
| 8,182,991 B1 | 5/2012 | Kaiser et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett |
| 8,263,335 B2 | 9/2012 | Carr et al. |
| 8,268,605 B2 | 9/2012 | Sorge et al. |
| 8,283,148 B2 | 10/2012 | Sorge et al. |
| 8,288,093 B2 | 10/2012 | Hall et al. |
| 8,298,767 B2 | 10/2012 | Brenner et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,433 B2 | 11/2012 | Brenner |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,383,338 B2 | 2/2013 | Kitzman et al. |
| 8,415,138 B2 | 4/2013 | Leproust |
| 8,435,736 B2 | 5/2013 | Gibson et al. |
| 8,445,205 B2 | 5/2013 | Brenner |
| 8,445,206 B2 | 5/2013 | Bergmann et al. |
| 8,470,996 B2 | 6/2013 | Brenner |
| 8,476,018 B2 | 7/2013 | Brenner |
| 8,476,598 B1 | 7/2013 | Pralle et al. |
| 8,481,292 B2 | 7/2013 | Casbon et al. |
| 8,481,309 B2 | 7/2013 | Zhang et al. |
| 8,491,561 B2 | 7/2013 | Borenstein et al. |
| 8,497,069 B2 | 7/2013 | Hutchison, III et al. |
| 8,500,979 B2 | 8/2013 | Elibol et al. |
| 8,501,454 B2 | 8/2013 | Liu et al. |
| 8,507,226 B2 | 8/2013 | Carr et al. |
| 8,507,239 B2 | 8/2013 | Lubys et al. |
| 8,507,272 B2 | 8/2013 | Zhang et al. |
| 8,530,197 B2 | 9/2013 | Li et al. |
| 8,552,174 B2 | 10/2013 | Dellinger et al. |
| 8,563,478 B2 | 10/2013 | Gormley et al. |
| 8,569,046 B2 | 10/2013 | Love et al. |
| 8,577,621 B2 | 11/2013 | Troup et al. |
| 8,586,310 B2 | 11/2013 | Mitra et al. |
| 8,614,092 B2 | 12/2013 | Zhang et al. |
| 8,642,755 B2 | 2/2014 | Sierzchala et al. |
| 8,664,164 B2 | 3/2014 | Ericsson et al. |
| 8,669,053 B2 | 3/2014 | Stuelpnagel et al. |
| 8,679,756 B1 | 3/2014 | Brenner et al. |
| 8,685,642 B2 | 4/2014 | Sampas |

(56) References Cited

U.S. PATENT DOCUMENTS

| | | |
|---|---|---|
| 8,685,676 B2 | 4/2014 | Hogrefe et al. |
| 8,685,678 B2 | 4/2014 | Casbon et al. |
| 8,715,933 B2 | 5/2014 | Oliver |
| 8,715,967 B2 | 5/2014 | Casbon et al. |
| 8,716,467 B2 | 5/2014 | Jacobson |
| 8,722,368 B2 | 5/2014 | Casbon et al. |
| 8,722,585 B2 | 5/2014 | Wang |
| 8,728,766 B2 | 5/2014 | Casbon et al. |
| 8,741,606 B2 | 6/2014 | Casbon et al. |
| 8,808,896 B2 | 8/2014 | Choo et al. |
| 8,808,986 B2 | 8/2014 | Jacobson et al. |
| 8,815,600 B2 | 8/2014 | Liu et al. |
| 8,889,851 B2 | 11/2014 | Leproust et al. |
| 8,932,994 B2 | 1/2015 | Gormley et al. |
| 8,962,532 B2 | 2/2015 | Shapiro et al. |
| 8,968,999 B2 | 3/2015 | Gibson et al. |
| 8,980,563 B2 | 3/2015 | Zheng et al. |
| 9,018,365 B2 | 4/2015 | Brenner |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,102,731 B2 | 8/2015 | Boone et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,194,001 B2 | 11/2015 | Brenner |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,328,378 B2 | 5/2016 | Earnshaw et al. |
| 9,347,091 B2 | 5/2016 | Bergmann et al. |
| 9,375,748 B2 | 6/2016 | Harumoto et al. |
| 9,376,677 B2 | 6/2016 | Mir |
| 9,376,678 B2 | 6/2016 | Gormley et al. |
| 9,384,320 B2 | 7/2016 | Church |
| 9,384,920 B1 | 7/2016 | Bakulich |
| 9,388,407 B2 | 7/2016 | Jacobson |
| 9,394,333 B2 | 7/2016 | Wada et al. |
| 9,403,141 B2 | 8/2016 | Banyai et al. |
| 9,409,139 B2 | 8/2016 | Banyai et al. |
| 9,410,149 B2 | 8/2016 | Brenner et al. |
| 9,410,173 B2 | 8/2016 | Betts et al. |
| 9,416,411 B2 | 8/2016 | Stuelpnagel et al. |
| 9,422,600 B2 | 8/2016 | Ramu et al. |
| 9,487,824 B2 | 11/2016 | Kutyavin et al. |
| 9,499,848 B2 | 11/2016 | Carr et al. |
| 9,523,122 B2 | 12/2016 | Zheng et al. |
| 9,528,148 B2 | 12/2016 | Zheng et al. |
| 9,534,251 B2 | 1/2017 | Young et al. |
| 9,555,388 B2 | 1/2017 | Banyai et al. |
| 9,568,839 B2 | 2/2017 | Stahler et al. |
| 9,580,746 B2 | 2/2017 | Leproust et al. |
| 9,670,529 B2 | 6/2017 | Osborne et al. |
| 9,670,536 B2 | 6/2017 | Casbon et al. |
| 9,677,067 B2 | 6/2017 | Toro et al. |
| 9,695,211 B2 | 7/2017 | Wada et al. |
| 9,718,060 B2 | 8/2017 | Venter et al. |
| 9,745,573 B2 | 8/2017 | Stuelpnagel et al. |
| 9,745,619 B2 | 8/2017 | Rabbani et al. |
| 9,765,387 B2 | 9/2017 | Rabbani et al. |
| 9,771,576 B2 | 9/2017 | Gibson et al. |
| 9,833,761 B2 | 12/2017 | Banyai et al. |
| 9,834,774 B2 | 12/2017 | Carstens |
| 9,839,894 B2 | 12/2017 | Banyai et al. |
| 9,879,283 B2 | 1/2018 | Ravinder et al. |
| 9,889,423 B2 | 2/2018 | Banyai et al. |
| 9,895,673 B2 | 2/2018 | Peck et al. |
| 9,925,510 B2 | 3/2018 | Jacobson et al. |
| 9,932,576 B2 | 4/2018 | Raymond et al. |
| 9,981,239 B2 | 5/2018 | Banyai et al. |
| 10,053,688 B2 | 8/2018 | Cox |
| 10,272,410 B2 | 4/2019 | Banyai |
| 10,384,188 B2 | 8/2019 | Banyai et al. |
| 10,583,415 B2 | 3/2020 | Banyai et al. |
| 10,618,024 B2 | 4/2020 | Banyai et al. |
| 10,632,445 B2 | 4/2020 | Banyai et al. |
| 10,669,304 B2 | 6/2020 | Indermuhle et al. |
| 10,754,994 B2 | 8/2020 | Peck |
| 10,773,232 B2 | 9/2020 | Banyai et al. |
| 10,844,373 B2 | 11/2020 | Cox et al. |
| 10,936,953 B2 | 3/2021 | Bramlett et al. |
| 10,963,953 B2 | 3/2021 | Sweeder et al. |
| 10,975,372 B2 | 4/2021 | Cox et al. |
| 11,214,798 B2 | 1/2022 | Brown |
| 11,236,393 B2 | 2/2022 | Dubinsky et al. |
| 11,268,149 B2 | 3/2022 | Targan et al. |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0025561 A1 | 2/2002 | Hodgson |
| 2002/0058802 A1 | 5/2002 | Dellinger et al. |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |
| 2002/0119459 A1 | 8/2002 | Griffiths et al. |
| 2002/0132308 A1 | 9/2002 | Liu et al. |
| 2002/0155439 A1 | 10/2002 | Rodriguez et al. |
| 2002/0160536 A1 | 10/2002 | Regnier et al. |
| 2002/0164824 A1 | 11/2002 | Xiao et al. |
| 2003/0008411 A1 | 1/2003 | Van Dam et al. |
| 2003/0022207 A1 | 1/2003 | Balasubramanian et al. |
| 2003/0022240 A1 | 1/2003 | Luo et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0082719 A1 | 5/2003 | Schumacher et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0130827 A1 | 7/2003 | Bentzien et al. |
| 2003/0138782 A1 | 7/2003 | Evans |
| 2003/0143605 A1 | 7/2003 | Lok et al. |
| 2003/0148291 A1 | 8/2003 | Robotti |
| 2003/0148344 A1 | 8/2003 | Rothberg et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du Breuil Lastrucci |
| 2004/0009498 A1 | 1/2004 | Short |
| 2004/0043509 A1 | 3/2004 | Stahler et al. |
| 2004/0053362 A1 | 3/2004 | De Luca et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 | 6/2004 | McGall et al. |
| 2004/0110133 A1 | 8/2004 | Xu et al. |
| 2004/0175710 A1 | 9/2004 | Haushalter |
| 2004/0175734 A1 | 9/2004 | Stahler et al. |
| 2004/0191810 A1 | 9/2004 | Yamamoto |
| 2004/0213795 A1 | 10/2004 | Collins et al. |
| 2004/0219663 A1 | 11/2004 | Page |
| 2004/0236027 A1 | 11/2004 | Maeji et al. |
| 2004/0248161 A1 | 12/2004 | Rothberg et al. |
| 2004/0253242 A1 | 12/2004 | Bowdish et al. |
| 2004/0259146 A1 | 12/2004 | Friend et al. |
| 2005/0022895 A1 | 2/2005 | Barth et al. |
| 2005/0049402 A1 | 3/2005 | Babcook et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0112636 A1 | 5/2005 | Hurt et al. |
| 2005/0112679 A1 | 5/2005 | Myerson et al. |

(56) References Cited

U.S. PATENT DOCUMENTS

| | | |
|---|---|---|
| 2005/0118706 A1 | 6/2005 | Pirrung et al. |
| 2005/0124022 A1 | 6/2005 | Srinivasan et al. |
| 2005/0137805 A1 | 6/2005 | Lewin |
| 2005/0208513 A1 | 9/2005 | Agbo et al. |
| 2005/0214778 A1 | 9/2005 | Peck et al. |
| 2005/0214779 A1 | 9/2005 | Peck et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2005/0287585 A1 | 12/2005 | Oleinikov |
| 2006/0003381 A1 | 1/2006 | Gilmore et al. |
| 2006/0003958 A1 | 1/2006 | Melville et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |
| 2006/0078927 A1 | 4/2006 | Peck et al. |
| 2006/0078937 A1 | 4/2006 | Korlach et al. |
| 2006/0127920 A1 | 5/2006 | Church et al. |
| 2006/0134638 A1 | 6/2006 | Mulligan et al. |
| 2006/0160138 A1 | 7/2006 | Church |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2007/0031857 A1 | 2/2007 | Makarov et al. |
| 2007/0031877 A1 | 2/2007 | Stahler et al. |
| 2007/0043516 A1 | 2/2007 | Gustafsson |
| 2007/0054127 A1 | 3/2007 | Hergenrother et al. |
| 2007/0059692 A1 | 3/2007 | Gao et al. |
| 2007/0087349 A1 | 4/2007 | Staehler et al. |
| 2007/0099196 A1 | 5/2007 | Kauppinen et al. |
| 2007/0099208 A1 | 5/2007 | Drmanac et al. |
| 2007/0122817 A1 | 5/2007 | Church et al. |
| 2007/0128635 A1 | 6/2007 | Macevicz |
| 2007/0141557 A1 | 6/2007 | Raab et al. |
| 2007/0196834 A1 | 8/2007 | Cerrina et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085511 A1 | 4/2008 | Peck et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0300842 A1 | 12/2008 | Govindarajan et al. |
| 2008/0308884 A1 | 12/2008 | Kalvesten |
| 2008/0311628 A1 | 12/2008 | Shoemaker |
| 2009/0036664 A1 | 2/2009 | Peter |
| 2009/0053704 A1 | 2/2009 | Novoradovskaya et al. |
| 2009/0062129 A1 | 3/2009 | McKernan et al. |
| 2009/0074771 A1 | 3/2009 | Koenig et al. |
| 2009/0087840 A1 | 4/2009 | Baynes et al. |
| 2009/0088679 A1 | 4/2009 | Wood et al. |
| 2009/0105094 A1 | 4/2009 | Heiner et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0246788 A1 | 10/2009 | Albert et al. |
| 2009/0263802 A1 | 10/2009 | Drmanac |
| 2009/0285825 A1 | 11/2009 | Kini et al. |
| 2009/0324546 A1 | 12/2009 | Notka et al. |
| 2010/0004143 A1 | 1/2010 | Shibahara |
| 2010/0008851 A1 | 1/2010 | Nicolaides et al. |
| 2010/0009872 A1 | 1/2010 | Eid et al. |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0099103 A1 | 4/2010 | Hsieh et al. |
| 2010/0111768 A1 | 5/2010 | Banerjee et al. |
| 2010/0160463 A1 | 6/2010 | Wang et al. |
| 2010/0167950 A1 | 7/2010 | Juang et al. |
| 2010/0173364 A1 | 7/2010 | Evans, Jr. et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0272711 A1 | 10/2010 | Feldman et al. |
| 2010/0286290 A1 | 11/2010 | Lohmann et al. |
| 2010/0292102 A1 | 11/2010 | Nouri |
| 2010/0300882 A1 | 12/2010 | Zhang |
| 2010/0311960 A1 | 12/2010 | Dellinger |
| 2010/0323404 A1 | 12/2010 | Lathrop |
| 2011/0009607 A1 | 1/2011 | Komiyama et al. |
| 2011/0082055 A1 | 4/2011 | Fox et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0201528 A1 | 8/2011 | Baek et al. |
| 2011/0217738 A1 | 9/2011 | Jacobson |
| 2011/0229975 A1 | 9/2011 | Matthiesen et al. |
| 2011/0230653 A1 | 9/2011 | Novoradovskaya et al. |
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0032366 A1 | 2/2012 | Ivniski et al. |
| 2012/0046175 A1 | 2/2012 | Rodesch et al. |
| 2012/0050411 A1 | 3/2012 | Mabritto et al. |
| 2012/0094847 A1 | 4/2012 | Warthmann et al. |
| 2012/0128548 A1 | 5/2012 | West et al. |
| 2012/0129704 A1 | 5/2012 | Gunderson et al. |
| 2012/0149602 A1 | 6/2012 | Friend et al. |
| 2012/0164127 A1 | 6/2012 | Short et al. |
| 2012/0164633 A1 | 6/2012 | Laffler |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |
| 2012/0315670 A1 | 12/2012 | Jacobson et al. |
| 2012/0322681 A1 | 12/2012 | Kung et al. |
| 2013/0005585 A1 | 1/2013 | Anderson et al. |
| 2013/0005612 A1 | 1/2013 | Carr et al. |
| 2013/0017642 A1 | 1/2013 | Milgrew et al. |

(56) References Cited

U.S. PATENT DOCUMENTS

| | | |
|---|---|---|
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0040836 A1 | 2/2013 | Himmler et al. |
| 2013/0045483 A1 | 2/2013 | Treusch et al. |
| 2013/0053252 A1 | 2/2013 | Xie et al. |
| 2013/0059296 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |
| 2013/0137861 A1 | 5/2013 | Leproust et al. |
| 2013/0164308 A1 | 6/2013 | Foletti et al. |
| 2013/0165328 A1 | 6/2013 | Previte et al. |
| 2013/0196864 A1 | 8/2013 | Govindarajan et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0261027 A1 | 10/2013 | Li et al. |
| 2013/0281308 A1 | 10/2013 | Kung et al. |
| 2013/0289246 A1 | 10/2013 | Crowe et al. |
| 2013/0296192 A1 | 11/2013 | Jacobson et al. |
| 2013/0296194 A1 | 11/2013 | Jacobson et al. |
| 2013/0298265 A1 | 11/2013 | Cunnac et al. |
| 2013/0309725 A1 | 11/2013 | Jacobson et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0031240 A1 | 1/2014 | Behlke et al. |
| 2014/0038240 A1 | 2/2014 | Temme et al. |
| 2014/0106394 A1 | 4/2014 | Ko et al. |
| 2014/0141982 A1 | 5/2014 | Jacobson et al. |
| 2014/0170665 A1 | 6/2014 | Hiddessen et al. |
| 2014/0178992 A1 | 6/2014 | Nakashima et al. |
| 2014/0221250 A1 | 8/2014 | Vasquez et al. |
| 2014/0274729 A1 | 9/2014 | Kurn et al. |
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0056609 A1 | 2/2015 | Daum et al. |
| 2015/0057625 A1 | 2/2015 | Coulthard |
| 2015/0065357 A1 | 3/2015 | Fox |
| 2015/0065393 A1 | 3/2015 | Jacobson |
| 2015/0099870 A1 | 4/2015 | Bennett et al. |
| 2015/0119293 A1 | 4/2015 | Short |
| 2015/0120265 A1 | 4/2015 | Amirav-Drory et al. |
| 2015/0159152 A1 | 6/2015 | Allen et al. |
| 2015/0183853 A1 | 7/2015 | Sharma et al. |
| 2015/0191524 A1 | 7/2015 | Smith et al. |
| 2015/0191624 A1 | 7/2015 | Scheibel et al. |
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0240280 A1 | 8/2015 | Gibson et al. |
| 2015/0261664 A1 | 9/2015 | Goldman et al. |
| 2015/0269313 A1 | 9/2015 | Church |
| 2015/0293102 A1 | 10/2015 | Shim |
| 2015/0307875 A1 | 10/2015 | Happe et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0019341 A1 | 1/2016 | Harris et al. |
| 2016/0024138 A1 | 1/2016 | Gebeyehu et al. |
| 2016/0024576 A1 | 1/2016 | Chee et al. |
| 2016/0026753 A1 | 1/2016 | Krishnaswami et al. |
| 2016/0026758 A1 | 1/2016 | Jabara et al. |
| 2016/0032396 A1 | 2/2016 | Diehn et al. |
| 2016/0046973 A1 | 2/2016 | Efcavitch et al. |
| 2016/0046974 A1 | 2/2016 | Efcavitch et al. |
| 2016/0082472 A1 | 3/2016 | Perego et al. |
| 2016/0089651 A1 | 3/2016 | Banyai |
| 2016/0090422 A1 | 3/2016 | Reif et al. |
| 2016/0090592 A1 | 3/2016 | Banyai et al. |
| 2016/0096160 A1 | 4/2016 | Banyai et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0122800 A1 | 5/2016 | Bernick et al. |
| 2016/0152972 A1 | 6/2016 | Stapleton et al. |
| 2016/0168611 A1 | 6/2016 | Efcavitch et al. |
| 2016/0184788 A1 | 6/2016 | Hall et al. |
| 2016/0200759 A1 | 7/2016 | Srivastava et al. |
| 2016/0215283 A1 | 7/2016 | Braman et al. |
| 2016/0229884 A1 | 8/2016 | Indermuhle et al. |
| 2016/0230175 A1 | 8/2016 | Carstens |
| 2016/0230221 A1 | 8/2016 | Bergmann et al. |
| 2016/0251651 A1 | 9/2016 | Banyai et al. |
| 2016/0256846 A1 | 9/2016 | Smith et al. |
| 2016/0264958 A1 | 9/2016 | Toro et al. |
| 2016/0289758 A1 | 10/2016 | Akeson et al. |
| 2016/0289839 A1 | 10/2016 | Harumoto et al. |
| 2016/0303535 A1 | 10/2016 | Banyai et al. |
| 2016/0304862 A1 | 10/2016 | Igawa et al. |
| 2016/0304946 A1 | 10/2016 | Betts et al. |
| 2016/0310426 A1 | 10/2016 | Wu |
| 2016/0310927 A1 | 10/2016 | Banyai et al. |
| 2016/0318016 A1 | 11/2016 | Hou et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0348098 A1 | 12/2016 | Stuelpnagel et al. |
| 2016/0354752 A1 | 12/2016 | Banyai et al. |
| 2016/0355880 A1 | 12/2016 | Gormley et al. |
| 2017/0017436 A1 | 1/2017 | Church |
| 2017/0066844 A1 | 3/2017 | Glanville |
| 2017/0067047 A1 | 3/2017 | Link et al. |
| 2017/0067099 A1 | 3/2017 | Zheng et al. |
| 2017/0073664 A1 | 3/2017 | McCafferty et al. |
| 2017/0073731 A1 | 3/2017 | Zheng et al. |
| 2017/0081660 A1 | 3/2017 | Cox et al. |
| 2017/0081716 A1 | 3/2017 | Peck |
| 2017/0088887 A1 | 3/2017 | Makarov et al. |
| 2017/0095785 A1 | 4/2017 | Banyai et al. |
| 2017/0096706 A1 | 4/2017 | Behlke et al. |
| 2017/0114404 A1 | 4/2017 | Behlke et al. |
| 2017/0141793 A1 | 5/2017 | Strauss et al. |
| 2017/0147748 A1 | 5/2017 | Staehler et al. |
| 2017/0151546 A1 | 6/2017 | Peck et al. |
| 2017/0159044 A1 | 6/2017 | Toro et al. |
| 2017/0175110 A1 | 6/2017 | Jacobson et al. |
| 2017/0218537 A1 | 8/2017 | Olivares |
| 2017/0233764 A1 | 8/2017 | Young et al. |
| 2017/0247473 A1 | 8/2017 | Short |
| 2017/0249345 A1 | 8/2017 | Malik et al. |
| 2017/0253644 A1 | 9/2017 | Steyaert et al. |
| 2017/0298432 A1 | 10/2017 | Holt |
| 2017/0320061 A1 | 11/2017 | Venter et al. |

(56) References Cited

U.S. PATENT DOCUMENTS

| | | |
|---|---|---|
| 2017/0327819 A1 | 11/2017 | Banyai et al. |
| 2017/0355984 A1 | 12/2017 | Evans et al. |
| 2017/0357752 A1 | 12/2017 | Diggans |
| 2017/0362589 A1 | 12/2017 | Banyai et al. |
| 2018/0029001 A1 | 2/2018 | Banyai et al. |
| 2018/0051278 A1 | 2/2018 | Cox et al. |
| 2018/0051280 A1 | 2/2018 | Gibson et al. |
| 2018/0068060 A1 | 3/2018 | Ceze et al. |
| 2018/0101487 A1 | 4/2018 | Peck |
| 2018/0104664 A1 | 4/2018 | Fernandez |
| 2018/0126355 A1 | 5/2018 | Peck et al. |
| 2018/0142289 A1 | 5/2018 | Zeitoun et al. |
| 2018/0171509 A1 | 6/2018 | Cox et al. |
| 2018/0236425 A1 | 8/2018 | Banyai et al. |
| 2018/0264428 A1 | 9/2018 | Banyai et al. |
| 2018/0273936 A1 | 9/2018 | Cox et al. |
| 2018/0282721 A1 | 10/2018 | Cox et al. |
| 2018/0291445 A1 | 10/2018 | Betts et al. |
| 2018/0312834 A1 | 11/2018 | Cox et al. |
| 2018/0326388 A1 | 11/2018 | Banyai et al. |
| 2018/0334712 A1 | 11/2018 | Singer et al. |
| 2018/0346585 A1 | 12/2018 | Zhang et al. |
| 2018/0355351 A1 | 12/2018 | Nugent et al. |
| 2019/0060345 A1 | 2/2019 | Harrison et al. |
| 2019/0083596 A1 | 3/2019 | Orentas et al. |
| 2019/0118154 A1 | 4/2019 | Marsh et al. |
| 2019/0135926 A1 | 5/2019 | Glanville |
| 2019/0224711 A1 | 7/2019 | Demeris, Jr. |
| 2019/0240636 A1 | 8/2019 | Peck et al. |
| 2019/0314783 A1 | 10/2019 | Banyai et al. |
| 2019/0352635 A1 | 11/2019 | Toro et al. |
| 2019/0366293 A1 | 12/2019 | Banyai et al. |
| 2019/0366294 A1 | 12/2019 | Banyai et al. |
| 2020/0017907 A1 | 1/2020 | Zeitoun et al. |
| 2020/0056229 A1 | 2/2020 | Mir |
| 2020/0102611 A1 | 4/2020 | Zeitoun et al. |
| 2020/0156037 A1 | 5/2020 | Banyai et al. |
| 2020/0181667 A1 | 6/2020 | Wu et al. |
| 2020/0222875 A1 | 7/2020 | Peck et al. |
| 2020/0283760 A1 | 9/2020 | Nugent et al. |
| 2020/0299322 A1 | 9/2020 | Indermuhle et al. |
| 2020/0299684 A1 | 9/2020 | Toro et al. |
| 2020/0308575 A1 | 10/2020 | Sato |
| 2020/0325235 A1 | 10/2020 | Tabibiazar et al. |
| 2020/0342143 A1 | 10/2020 | Peck |
| 2021/0002710 A1 | 1/2021 | Gantt et al. |
| 2021/0040476 A1 | 2/2021 | Cox et al. |
| 2021/0071168 A1 | 3/2021 | Nugent et al. |
| 2021/0102192 A1 | 4/2021 | Tabibiazar et al. |
| 2021/0102195 A1 | 4/2021 | Sato et al. |
| 2021/0102198 A1 | 4/2021 | Cox et al. |
| 2021/0115594 A1 | 4/2021 | Cox et al. |
| 2021/0129108 A1 | 5/2021 | Marsh et al. |
| 2021/0142182 A1 | 5/2021 | Bramlett et al. |
| 2021/0147830 A1 | 5/2021 | Liss |
| 2021/0170356 A1 | 6/2021 | Peck et al. |
| 2021/0179724 A1 | 6/2021 | Sato et al. |
| 2021/0207197 A1 | 7/2021 | Gantt et al. |
| 2021/0332078 A1 | 10/2021 | Wu |
| 2021/0348220 A1 | 11/2021 | Zeitoun et al. |
| 2021/0355194 A1 | 11/2021 | Sato et al. |
| 2021/0395344 A1 | 12/2021 | Sato et al. |
| 2022/0032256 A1 | 2/2022 | Lackey et al. |
| 2022/0064206 A1 | 3/2022 | Fernandez et al. |
| 2022/0064313 A1 | 3/2022 | Sato et al. |
| 2022/0064628 A1 | 3/2022 | Toro et al. |
| 2022/0106586 A1 | 4/2022 | Nugent et al. |
| 2022/0106590 A1 | 4/2022 | Arbiza et al. |
| 2022/0135690 A1 | 5/2022 | Sato et al. |
| 2022/0135965 A1 | 5/2022 | Gantt et al. |
| 2022/0138354 A1 | 5/2022 | Peck |
| 2022/0145289 A1 | 5/2022 | Lackey et al. |
| 2022/0206001 A1 | 6/2022 | Sato |
| 2022/0243195 A1 | 8/2022 | Nugent et al. |
| 2022/0246236 A1 | 8/2022 | Amirav-Drory |
| 2022/0259319 A1 | 8/2022 | Sato et al. |
| 2022/0259638 A1 | 8/2022 | Brown |
| 2022/0277808 A1 | 9/2022 | Arbiza et al. |
| 2022/0281989 A1 | 9/2022 | Glanville |
| 2022/0307010 A1 | 9/2022 | Sato et al. |
| 2022/0315971 A1 | 10/2022 | Wu et al. |

FOREIGN PATENT DOCUMENTS

| | | |
|---|---|---|
| CN | 1771336 A | 5/2006 |
| CN | 10127758 A | 10/2008 |
| CN | 102159726 A | 8/2011 |
| CN | 103003431 A | 3/2013 |
| CN | 103907117 A | 7/2014 |
| CN | 104520864 A | 4/2015 |
| CN | 104562213 A | 4/2015 |
| CN | 104734848 A | 6/2015 |
| CN | 104974929 A | 10/2015 |
| CN | 204714802 U | 10/2015 |
| CN | 105637097 A | 6/2016 |
| DE | 10260805 A1 | 7/2004 |
| DO | WO-03066212 A2 | 8/2003 |
| EA | 201890763 A1 | 8/2018 |
| EP | 0090789 A1 | 10/1983 |
| EP | 0126621 B1 | 8/1990 |
| EP | 0753057 A1 | 1/1997 |
| EP | 1153127 A1 | 11/2001 |
| EP | 1314783 A1 | 5/2003 |
| EP | 1363125 A2 | 11/2003 |
| EP | 1546387 A2 | 6/2005 |
| EP | 1153127 B1 | 7/2006 |
| EP | 1728860 A1 | 12/2006 |
| EP | 1072010 B1 | 4/2010 |
| EP | 2175021 A2 | 4/2010 |
| EP | 2330216 A1 | 6/2011 |
| EP | 1343802 B1 | 5/2012 |
| EP | 2504449 A1 | 10/2012 |
| EP | 2751729 A1 | 7/2014 |
| EP | 2872629 A1 | 5/2015 |
| EP | 2928500 A1 | 10/2015 |
| EP | 2971034 A1 | 1/2016 |
| EP | 3030682 A2 | 6/2016 |
| EP | 3044228 A4 | 4/2017 |
| EP | 2994509 B1 | 6/2017 |
| EP | 3204518 A1 | 8/2017 |
| JP | H07505530 A | 6/1995 |
| JP | 2001518086 A | 10/2001 |
| JP | 2002511276 A | 4/2002 |
| JP | 2002536977 A | 11/2002 |
| JP | 2002538790 A | 11/2002 |
| JP | 2003522119 A | 7/2003 |
| JP | 2004521628 A | 7/2004 |
| JP | 2006503586 A | 2/2006 |
| JP | 2006238724 A | 9/2006 |
| JP | 2008505642 A | 2/2008 |
| JP | 2008097189 A | 4/2008 |
| JP | 2008523786 A | 7/2008 |
| JP | 2008214343 A | 9/2008 |
| JP | 2009294195 A | 12/2009 |
| JP | 2016527313 A | 9/2016 |
| WO | WO-9015070 A1 | 12/1990 |
| WO | WO-9210092 A1 | 6/1992 |
| WO | WO-9210588 A1 | 6/1992 |
| WO | WO-9309668 A1 | 5/1993 |
| WO | WO-9320242 A1 | 10/1993 |
| WO | WO-9525116 A1 | 9/1995 |
| WO | WO-9526397 A1 | 10/1995 |
| WO | WO-9615861 A1 | 5/1996 |
| WO | WO-9710365 A1 | 3/1997 |
| WO | WO-9822541 A2 | 5/1998 |
| WO | WO-9841531 A2 | 9/1998 |
| WO | WO-9942813 A1 | 8/1999 |
| WO | WO-9953101 A1 | 10/1999 |
| WO | WO-0013017 A2 | 3/2000 |
| WO | WO-0018957 A1 | 4/2000 |
| WO | WO-0042559 A1 | 7/2000 |
| WO | WO-0042560 A2 | 7/2000 |
| WO | WO-0042561 A2 | 7/2000 |
| WO | WO-0049142 A1 | 8/2000 |

(56) References Cited

FOREIGN PATENT DOCUMENTS

| | | |
|---|---|---|
| WO | WO-0053617 A1 | 9/2000 |
| WO | WO-0156216 A2 | 8/2001 |
| WO | WO-0210443 A1 | 2/2002 |
| WO | WO-0156216 A3 | 3/2002 |
| WO | WO-0220537 A2 | 3/2002 |
| WO | WO-0224597 A2 | 3/2002 |
| WO | WO-0227638 A1 | 4/2002 |
| WO | WO-0233669 A1 | 4/2002 |
| WO | WO-02072791 A2 | 9/2002 |
| WO | WO-02072864 A2 | 9/2002 |
| WO | WO-03040410 A1 | 5/2003 |
| WO | WO-03046223 A1 | 6/2003 |
| WO | WO-03054232 A2 | 7/2003 |
| WO | WO-03060084 A2 | 7/2003 |
| WO | WO-03064026 A1 | 8/2003 |
| WO | WO-03064027 A2 | 8/2003 |
| WO | WO-03064699 A2 | 8/2003 |
| WO | WO-03065038 A2 | 8/2003 |
| WO | WO-03089605 A2 | 10/2003 |
| WO | WO-03093504 A1 | 11/2003 |
| WO | WO-03100012 A2 | 12/2003 |
| WO | WO-2004024886 A2 | 3/2004 |
| WO | WO-2004029220 A2 | 4/2004 |
| WO | WO-2004029586 A1 | 4/2004 |
| WO | WO-2004031351 A2 | 4/2004 |
| WO | WO-2004031399 A2 | 4/2004 |
| WO | WO-2004059556 A2 | 7/2004 |
| WO | WO-03060084 A3 | 8/2004 |
| WO | WO-2005014850 A2 | 2/2005 |
| WO | WO 2005051970 A2 | 6/2005 |
| WO | WO-2005059096 A2 | 6/2005 |
| WO | WO-2005059097 A2 | 6/2005 |
| WO | WO-2005093092 A2 | 10/2005 |
| WO | WO-2006023144 | 3/2006 |
| WO | WO-2006044956 A1 | 4/2006 |
| WO | WO-2006076679 A1 | 7/2006 |
| WO | WO-2006116476 A1 | 11/2006 |
| WO | WO-2007073171 A2 | 6/2007 |
| WO | WO-2007109221 A2 | 9/2007 |
| WO | WO-2007118214 A2 | 10/2007 |
| WO | WO-2007120627 A2 | 10/2007 |
| WO | WO-2007137242 A2 | 11/2007 |
| WO | WO-2008003116 A2 | 1/2008 |
| WO | WO-2008006078 A2 | 1/2008 |
| WO | WO-2008027558 A2 | 3/2008 |
| WO | WO-2008045380 | 4/2008 |
| WO | WO-2008054543 A2 | 5/2008 |
| WO | WO-2008063134 A1 | 5/2008 |
| WO | WO-2008063135 A1 | 5/2008 |
| WO | WO-2008068280 A1 | 6/2008 |
| WO | WO-2008103474 A1 | 8/2008 |
| WO | WO-2008109176 A2 | 9/2008 |
| WO | WO-2009132876 A1 | 11/2009 |
| WO | WO-2010001251 A2 | 1/2010 |
| WO | WO-2010025310 A2 | 3/2010 |
| WO | WO-2010025566 A1 | 3/2010 |
| WO | WO-2010027512 A2 | 3/2010 |
| WO | WO-2010089412 A1 | 8/2010 |
| WO | WO-2010141249 A2 | 12/2010 |
| WO | WO-2010141433 A2 | 12/2010 |
| WO | WO-2011020529 A2 | 2/2011 |
| WO | WO-2010141433 A3 | 4/2011 |
| WO | WO-2011053957 A2 | 5/2011 |
| WO | WO-2011056644 A2 | 5/2011 |
| WO | WO-2011056872 A2 | 5/2011 |
| WO | WO-2011066185 A1 | 6/2011 |
| WO | WO-2011068186 A1 | 6/2011 |
| WO | WO-2011085075 A2 | 7/2011 |
| WO | WO-2011103468 A2 | 8/2011 |
| WO | WO-2011109031 A1 | 9/2011 |
| WO | WO-2011143556 A1 | 11/2011 |
| WO | WO-2011150168 A1 | 12/2011 |
| WO | WO-2011161413 A2 | 12/2011 |
| WO | WO-2012013913 A1 | 2/2012 |
| WO | WO-2012061832 A1 | 5/2012 |
| WO | WO-2012078312 A2 | 6/2012 |
| WO | WO-2012149171 A1 | 11/2012 |
| WO | WO-2012154201 A1 | 11/2012 |
| WO | WO-2013010062 A2 | 1/2013 |
| WO | WO-2013030827 A1 | 3/2013 |
| WO | WO-2013032850 A2 | 3/2013 |
| WO | WO-2013036668 A1 | 3/2013 |
| WO | WO-2013049227 A2 | 4/2013 |
| WO | WO-2013101896 A1 | 7/2013 |
| WO | WO-2013134881 A1 | 9/2013 |
| WO | WO-2013154770 A1 | 10/2013 |
| WO | WO-2013170168 A1 | 11/2013 |
| WO | WO-2013177220 A1 | 11/2013 |
| WO | WO-2014004393 A1 | 1/2014 |
| WO | WO-2014008447 A1 | 1/2014 |
| WO | WO-2014021938 A1 | 2/2014 |
| WO | WO-2014035693 A2 | 3/2014 |
| WO | WO-2014088693 A1 | 6/2014 |
| WO | WO-2014089160 A1 | 6/2014 |
| WO | WO-2014093330 A1 | 6/2014 |
| WO | WO-2014093694 A2 | 6/2014 |
| WO | WO-2014151117 A1 | 9/2014 |
| WO | WO-2014151696 A1 | 9/2014 |
| WO | WO-2014160004 A1 | 10/2014 |
| WO | WO-2014160059 A1 | 10/2014 |
| WO | WO-2014206304 A1 | 12/2014 |
| WO | WO-2015017527 A2 | 2/2015 |
| WO | WO-2015021080 A2 | 2/2015 |
| WO | WO-2015021280 A1 | 2/2015 |
| WO | WO-2015031689 A1 | 3/2015 |
| WO | WO-2015040075 A1 | 3/2015 |
| WO | WO-2015054292 A1 | 4/2015 |
| WO | WO-2015066174 A1 | 5/2015 |
| WO | WO-2015081114 A2 | 6/2015 |
| WO | WO-2015081142 A1 | 6/2015 |
| WO | WO-2015081440 A1 | 6/2015 |
| WO | WO-2015090879 A1 | 6/2015 |
| WO | WO-2015095404 A2 | 6/2015 |
| WO | WO-2015120403 A1 | 8/2015 |
| WO | WO-2015136072 A1 | 9/2015 |
| WO | WO-2016162127 A1 | 9/2015 |
| WO | WO-2015160004 A1 | 10/2015 |
| WO | WO-2015175832 A1 | 11/2015 |
| WO | WO-2016007604 A1 | 1/2016 |
| WO | WO-2016011080 A2 | 1/2016 |
| WO | WO-2016022557 A1 | 2/2016 |
| WO | WO-2016053883 A1 | 4/2016 |
| WO | WO-2016055956 A1 | 4/2016 |
| WO | WO-2016065056 A1 | 4/2016 |
| WO | WO-2016126882 A1 | 8/2016 |
| WO | WO-2016126987 A1 | 8/2016 |
| WO | WO-2016130868 A2 | 8/2016 |
| WO | WO-2016161244 A2 | 10/2016 |
| WO | WO-2016164779 A1 | 10/2016 |
| WO | WO-2016172377 A1 | 10/2016 |
| WO | WO-2016173719 A1 | 11/2016 |
| WO | WO-2016183100 A1 | 11/2016 |
| WO | WO-2017049231 A1 | 3/2017 |
| WO | WO-2017053450 A1 | 3/2017 |
| WO | WO-2017059399 A1 | 4/2017 |
| WO | WO-2017095958 A1 | 6/2017 |
| WO | WO-2017100441 A1 | 6/2017 |
| WO | WO-2017118761 A1 | 7/2017 |
| WO | WO-2017158103 A1 | 9/2017 |
| WO | WO-2017214574 A1 | 12/2017 |
| WO | WO-2018026920 A1 | 2/2018 |
| WO | WO-2018038772 A1 | 3/2018 |
| WO | WO-2018057526 A2 | 3/2018 |
| WO | WO-2018094263 A1 | 5/2018 |
| WO | WO-2018112426 A1 | 6/2018 |
| WO | WO-2018119246 A1 | 6/2018 |
| WO | WO-2018156792 A1 | 8/2018 |
| WO | WO-2018170164 A1 | 9/2018 |
| WO | WO-2018170169 A1 | 9/2018 |
| WO | WO-2018170559 A1 | 9/2018 |
| WO | WO-2018200380 A1 | 11/2018 |
| WO | WO-2018231872 A1 | 12/2018 |
| WO | WO-2019014781 A1 | 1/2019 |
| WO | WO-2019051501 A1 | 3/2019 |

(56) References Cited

FOREIGN PATENT DOCUMENTS

| WO | WO-2019079769 A1 | 4/2019 |
|----|------------------|--------|
| WO | WO-2019084500 A1 | 5/2019 |
| WO | WO-2019136175 A1 | 7/2019 |
| WO | WO-2019222706 A1 | 11/2019 |
| WO | WO-2020139871 A1 | 7/2020 |
| WO | WO-2020176362 A1 | 9/2020 |
| WO | WO-2020176678 A1 | 9/2020 |
| WO | WO-2020176680 A1 | 9/2020 |
| WO | WO-2020257612 A1 | 12/2020 |
| WO | WO-2021046655 A1 | 3/2021 |
| WO | WO-2021119193 A2 | 6/2021 |
| WO | WO-2022010934 A2 | 1/2022 |
| WO | WO-2022046797 A1 | 3/2022 |
| WO | WO-2022046944 A2 | 3/2022 |
| WO | WO-2022047076 A1 | 3/2022 |
| WO | WO-2022076326 A1 | 4/2022 |
| WO | WO-2022086866 A1 | 4/2022 |
| WO | WO-2022087293 A1 | 4/2022 |
| WO | WO-2022098662 A2 | 5/2022 |
| WO | WO-2022159620 A1 | 7/2022 |
| WO | WO-2022178137 A1 | 8/2022 |

OTHER PUBLICATIONS

Borda et al.: Secret writing by DNA hybridization. Acta Technica Napocensis Electronics and Telecommunications. 50(2):21-24 (2008).
Chervin et al.: Design of T-cell receptor libraries with diverse binding properties to examine adoptive T-cell responses. Gene Therapy. 20(6):634-644 (2012).
Cleary et al.: Production of complex nucleic acid libraries using highly parallel in situ oligonucleotide synthesis. Nat Methods. 1(3):241-248 (2004).
Cui et al.: Information Security Technology Based on DNA Computing. International Workshop on Anti-Counterfeiting, Security and Identification (ASID); IEEE Xplore 4 pages (2007).
Fernández-Quintero et al.: Characterizing the Diversity of the CDR-H3 Loop Conformational Ensembles in Relationship to Antibody Binding Properties. Front. Immunol. 9:1-11 (2019).
GE Healthcare. AKTA oligopilot plus. Data File 18-114-66 AD ©. 8 pages (2006).
GE Healthcare. Robust and cost-efficient oligonucleotide synthesis. Application Note 28-4058-08 AA. 4 pages (2005).
Geetha et al.: Survey on Security Mechanisms for Public Cloud Data. 2016 International Conference on Emerging Trends in Engineering, Technology and Science (ICETETS). 8 pages (2016).
Goodwin et al.: Immunoglobulin heavy chain variable region, partial [*Homo sapiens*]. Genbank entry (online). National Institute of Biotechnology Information. (2018) https://www.ncbi.nim.nih.gov/protein/AXA12486.1.
Hauser et al.: Trends in GPCR drug discovery: new agents, targets and indications. Nature Reviews Drug Discovery, 16, 829-842 (2017). doi:10.1038/nrd.2017.178 https://www.nature.com/articles/nrd.2017.178.
Hopcroft et al.: What is the Young's Modulus of Silicon?. Journal of Microelectromechanical Systems. 19(2):229-238 (2010).
Hötzel et al.: A strategy for risk mitigation of antibodies with fast clearance. mAbs, 4(6), 753-760 (2012). doi:10.4161/mabs.22189 https://www.ncbi.nlm.nih.gov/pubmed/23778268.
Hudson: Matrix Assisted Synthetic Transformations: A Mosaic of Diverse Contributions. Journal of Combinatorial Chemistry. 1(6):403-457 (1999).
Jaiswal et al.: An architecture for creating collaborative semantically capable scientific data sharing infrastructures. Proceeding WIDM '06 Proceedings of the 8th annual ACM international workshop on Web information and data management. ACM Digital Library pp. 75-82 (2006).
Jang et al.: Characterization of T cell repertoire of blood, tumor, and ascites in ovarian cancer patients using next generation sequencing. Oncoimmunology, 4(11):e1030561:1-10 (2015).
Kalva et al.: Gibson Deletion: a novel application of isothermal in vitro recombination. Biological Procedures Online. 20(1):1-10 (2018).
Kosuri et al.: A scalable gene synthesis platform using high-fidelity DNA microchips Nat.Biotechnol. 28(12):1295-1299 (2010).
Lebl et al.: Economical Parallel Oligonucleotide and Peptide Synthesizer—Pet Oligator. Int. J. Peptide Res. Ther. 13(1-2):367-376 (2007).
Lee: Covalent End-Immobilization of Oligonucleotides onto Solid Surfaces; Thesis, Massachusetts Institute of Technology, Aug. 2001 (315 pages).
Leproust et al.: Synthesis of high-quality libraries of long (150mer) oligonucleotides by a novel depurination controlled process. Nucleic Acids Research. 38(8):2522-2540 (2010).
Malecek et al.: Engineering improved T cell receptors using an alanine-scan guided T cell display selection system. Journal of Immunological Methods. Elsevier Science Publishers. 392(1):1-11 (2013).
MLAB 2321 Molecular Diagnostics for Clinical Laboratory Science. Mar. 6, 2015.
Momentiv. Technical Data Sheet. Silquest A-1100. Momentiv. 1-6 (2020).
(Novartis Institutes for Biomedical Research) Immunoglobulin Heavy Chain [*Homo sapiens*]. National Center for Biotechnology Information. Genbank Entry. pp. 1-2 (2018) https://www.ncbi.nlm.nih.gov/nuccore/MH975524.1ttps://https://www.ncbi.nlm.nih.gov/nuccore/MH975524.1.
(Novartes Institutes for Biomedical Research) Immunoglobulin Lambda Chain [*Homo sapiens*]. National Center for Biotechnology Information. Genbank Entry. pp. 1-2 (2018) https://www.ncbi.nlm.nih.gov/nuccore/MH197552.4.1.
Nucleic acid thermodynamics. Wikipedia. Feb. 4, 2021.
O'Driscoll et al.: Synthetic DNA: The next generation of big data storage. Bioengineered. 4(3):123-125 (2013).
Opposition to European Patent No. 3030682 filed Mar. 3, 2021.
PCT/US2019/068435 International Search Report and Written Opinion dated Apr. 23, 2020.
PCT/US2020/019371 International Search Report and Written Opinion dated Jun. 25, 2020.
PCT/US2020/019986 International Search Report and Written Opinion dated Jul. 29, 2020.
PCT/US2020/019986 Invitation to Pay Additional Fees dated Jun. 5, 2020.
PCT/US2020/019988 International Search Report and Written Opinion dated Jul. 29, 2020.
PCT/US2020/019988 Invitation to Pay Additional Fees dated Jun. 8, 2020.
PCT/US2020/038679 International Search Report and Written Opinion dated Oct. 28, 2020.
PCT/US2020/052291 International Search Report and Written Opinion dated Mar. 10, 2021.
PCT/US2020/052291 Invitation to Pay Additional Fees dated Dec. 31, 2020.
PCT/US2020/052306 International Search Report and Written Opinion dated Mar. 2, 2021.
PCT/US2020/052306 Invitation to Pay Additional Fees dated Dec. 18, 2020.
PCT/US2020/064106 International Search Report and Written Opinion dated Jun. 3, 2021.
PCT/US2020/064106 Invitation to Pay Additional Fees dated Apr. 9, 2021.
Pigott et al.: The Use of a Novel Discovery Platform to Identify Peptide-Grafted Antibodies that Activate GLP-1 Receptor Signaling. Innovative Targeting Solutions Inc. (2013) XP055327428 retrieved from the internet: http://www.innovativetargeting.com/wo-content/uploads/2013/12/Pigott-et-al-Antibody-Engineering-2013.pdf.
Ponsel. High Affinity, Developability and Functional Size: The Holy Grail of Combinatorial Antibody Library Generation. Molecules. 16:3675-3700 (2011).
PubChem Data Sheet Dichloromethane. Printed from website https://pubchem.ncbi.nlm.nih.gov/compound/Dichloromethane (2020).
Quan et al.: Parallel on-chip gene synthesis and application to optimization of protein expression. Nature Biotechnology. 29:449-452 (2011).
Regep et al.: The H3 loop of antibodies shows unique structural characteristics. Proteins. 85(7):1311-1318 (2017).

(56) References Cited

OTHER PUBLICATIONS

Shipman et al.: Molecular recordings by directed CRISPR spacer acquisition. Science. 353(6298):1-16 (2016).
US. Appl. No. 14/452,429 Office Action dated Oct. 21, 2015.
U.S. Appl. No. 15/151,316 Final Office Action dated Jul. 9, 2020.
U.S. Appl. No. 15/156,134 Final Office Action dated Aug. 18, 2021.
U.S. Appl. No. 15/156,134 Office Action dated Nov. 25, 2020.
U.S. Appl. No. 15/245,054 Notice of Allowance dated Dec. 14, 2017.
U.S. Appl. No. 15/272,004 Final Office Action dated Mar. 18, 2021.
U.S. Appl. No. 15/272,004 Office Action dated Jun. 12, 2020.
U.S. Appl. No. 15/619,322 Final Office Action dated Jul. 9, 2021.
U.S. Appl. No. 15/619,322 Office Action dated Nov. 4, 2020.
U.S. Appl. No. 15/816,995 Office Action dated May 19, 2020.
U.S. Appl. No. 15/835,342 Final Office Action dated Sep. 8, 2020.
U.S. Appl. No. 15/835,342 Office Action dated Apr. 16, 2021.
U.S. Appl. No. 15/921,479 Final Office Action dated Jun. 15, 2020.
U.S. Appl. No. 15/921,479 Office Action dated Apr. 27, 2021.
U.S. Appl. No. 15/991,992 Office Action dated May 21, 2020.
U.S. Appl. No. 16/031,784 Office Action dated May 12, 2020.
U.S. Appl. No. 16/039,256 Final Office Action dated Mar. 30, 2021.
U.S. Appl. No. 16/039,256 Office Action dated Aug. 20, 2020.
U.S. Appl. No. 16/039,256 Restriction Requirement dated May 18, 2020.
U.S. Appl. No. 16/128,372 Final Office Action dated Mar. 18, 2021.
U.S. Appl. No. 16/128,372 Office Action dated Oct. 8, 2020.
U.S. Appl. No. 16/128,372 Restriction Requirement dated May 18, 2020.
U.S. Appl. No. 16/239,453 Office Action dated May 11, 2020.
U.S. Appl. No. 16/384,678 Final Office Action dated Oct. 15, 2020.
U.S. Appl. No. 16/530,717 Final Office Action dated Apr. 15, 2020.
U.S. Appl. No. 16/535,777 Final Office Action dated Oct. 20, 2020.
U.S. Appl. No. 16/535,777 Office Action dated Feb. 8, 2021.
U.S. Appl. No. 16/712,678 Restriction Requirement dated Aug. 25, 2021.
U.S. Appl. No. 16/798,275 Office Action dated Feb. 10, 2021.
U.S. Appl. No. 16/854,719 Restriction Requirement dated Jul. 28, 2021.
U.S. Appl. No. 16/879,705 Office Action dated Sep. 9, 2021.
U.S. Appl. No. 16/906,555 Office Action dated Aug. 17, 2021.
U.S. Appl. No. 17/154,906 Restriction Requirement dated Jul. 26, 2021.
U.S. Appl. No. 16/798,275 Roar Office Action dated Aug. 30, 2021.
Van der Velde: Thesis. Finding the Strength of Glass. Delft University of Technology. 1-16, (2015).
Xu et al.: Coordination between the Polymerase and 5'-Nuclease Components of DNA Porymerase I of *Escherichia coli*. The Journal of Biological Chemistry. 275(27):20949-20955 (2000).
Yazdi et al.: DNA-Based Storage: Trends and Methods, IEEE Transactions on Molecular, Biological and Multi-Scale Communications. IEEE. 1(3):230-246, (2016).
Abudayyeh et al., C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf , 17 pages.
Adessi, et al. Solid phase DNA amplification: characterisation of primer attachment and amplification mechanisms. Nucleic Acids Res. 28(20):E87, 2000.
Alexeyev, Mikhail F. et al., "Gene synthesis, bacterial expression and purification of the Rickettsia prowazekii ATP/ADP translocase", Biochimica et Biophysics Acta, 1419:299-306, 1999.
Al-Housseiny et al., Control of interfacial instabilities using flow geometry Nature Physics, 8:747-750, 2012.
Amblard, Francois et al., "A magnetic manipulator for studying local rheology and micromechanical properties of biological systems", Rev. Sci. Instrum., 67(3):18-827, 1996.
Andoni and Indyk, Near-Optimal Hashing Algorithms for Approximate Nearest Neighbor in High Dimensions, Communications of the ACM, 51(1):117-122, 2008.
Arkles, et al. The Role of Polarity in the Structure of Silanes Employed in Surface Modification. Silanes and Other Coupling Agents. 5:51-64, 2009.
Arkles, Hydrophobicity, Hydrophilicity Reprinted with permission from the Oct. 2006 issue of Paint & Coatings Industry magazine, Retrieved on Mar. 19, 2016, 10 pages.
Assi, Fabiano et al., "Massive-parallel adhesion and reactivity-measurements using simple and inexpensive magnetic tweezers", J. Appl. Phys., 92(9):5584-5586, 2002.
ATDBio, "Nucleic Acid Structure," Nucleic Acids Book, 9 pages, published on Jan. 22, 2005. from: http://www.atdbio.com/content/5/Nucleic-acid-structure.
ATDBio, "Solid-Phase Oligonucleotide Synthesis," Nucleic Acids Book, 20 pages, Published on Jul. 31, 2011. from: http://www.atdbio.com/content/17/Solid-phase-oligonucleotide-synthesis.
Au, Lo-Chun et al. "Gene synthesis by a LCR-based approach: high level production of Leptin-L54 using synthetic gene in *Escherichia coli*", Biochemical and Biophysical Research Communications, 248:200-203, 1998.
Baedeker, Mathias et al., Overexpression of a designed 2.2kb gene of eukaryotic phenylalanine ammonialyase in *Escherichia coli*•. FEBS Letters, 457:57-60, 1999.
Barbee, et al. Magnetic Assembly of High-Density DNA Arrays for Genomic Analyses. Anal Chem. 80(6):2149-2154, 2008.
Barton et al., A desk electrohydrodynamicjet printing system. Mechatronics, 20:611-616, 2010.
Beaucage, et al. Advances in the synthesis of oligonucleotides by the phosphoramidite approach. Tetrahedron. 48:2223-2311, 1992.
Beaucage, et al. Deoxynucleoside phosphoramidites—A new class of key intermediates for deoxypolynucleotide synthesis. Tetrahedron Lett. 22(20):1859-1862, 1981.
Beaucage, Serge L. et al., "The Chemical synthesis of DNA/RNA" Chapter 2 in: Encyclopedia of Cell Biology, 1:36-53, 2016.
Beaulieu, Martin et al., "PCR candidate region mismatch scanning adaptation to quantitative, high-throughput genotyping", Nucleic Acids Research, 29(5):1114-1124, 2001.
Beigelman, et al. Base-modified phosphoramidite analogs of pyrimidine ribonucleosides for RNA structure-activity studies. Methods Enzymol. 317:39-65, 2000.
Bethge et al., "Reverse synthesis and 3'-modification of RNA." Jan. 1, 2011, pages 64-64, XP055353420. Retrieved from the Internet: URL:http://www.is3na.org/assets/events/Category%202-Medicinal%20Chemistry%200f%2001igonucleotides%20%2864-108%29.pdf.
Binkowski et al., Correcting errors in synthetic DNA through consensus shuffling. Nucleic Acids Research, 33(6):e55, 8 pages, 2005.
Biswas, Indranil et al., "Identification and characterization of a thermostable MutS homolog from Thennus aquaticus", The Journal of Biological Chemistry, 271(9):5040-5048, 1996.
Biswas, Indranil et al., "Interaction of MutS protein with the major and minor grooves of a heteroduplex DNA", The Journal of Biological Chemistry, 272(20):13355-13364, 1997.
Bjornson, Keith P. et al., "Differential and simultaneous adenosine Di- and Tri~hosphate binding by MutS", The Journal of Biological Chemistry, 278(20):18557-18562, 2003.
Blanchard, et al., "High-Density Oligonucleotide Arrays," Biosensors & Bioelectronics, 11(6/7):687-690, 1996.
Blanchard, in: Genetic Engineering, Principles and Methods, vol. 20, Ed. J. Sedlow, New York: Plenum Press, p. 111-124, 1979.
Blawat et al., Forward error correction for DNA data storage. Procedia Computer Science, 80:1011-1022, 2016.
Bonini and Mondino, Adoptive T-cell therapy for cancer: The era of engineered T cells. European Journal of Immunology, 45:2457-2469, 2015.
Bornholt et al., A DNA-Based Archival Storage System, in International Conference on Architectural Support for Programming Languages and Operating Systems (ASPLOS), Apr. 2-6, 2016, Atlanta, GA, 2016, 637-649.
Borovkov et al., High-quality gene assembly directly from unpurified mixtures of microassay synthesized oligonucleotides. Nucleic Acid Research, 38(19):e180, 10 pages, 2010.

(56) References Cited

OTHER PUBLICATIONS

Brunet, Aims and methods of biosteganography. Journal of Biotechnology, 226:56-64, 2016.

Buermans et al., "Next Generation sequencing technology: Advances and applications," Biochimica et Biophysica Acta (BBA)—Molecular Basis of Disease, 1842:1931-1941, 2014.

Butler, et al. In situ synthesis of oligonucleotide arrays by using surface tension. J Am Chem Soc. 123(37):8887-94, 2001.

Calvert, Lithographically patterned self-assembled films. In: Organic Thin Films and Surfaces: Directions for The Nineties, Vvol. 20, p. 109, ed. by Abraham Ulman, San Diego: Academic Press, 1995.

Cardelli, Two-Domain DNA Strand Displacement, Electron. Proc. Theor. Comput. Sci., 26:47-61, 2010.

Carlson, "Time for New DNA Synthesis and Sequencing Cost Curves," 2014. [Online]. Available: http://www.synthesis.cc/synthesis/2014/02/time_for_new_cost_curves_2014. 10 pages.

Carr, et al. Protein-mediated error correction for de novo DNA synthesis. Nucleic Acids Res. 32(20):e162, 9 pages, 2004.

Caruthers, Chemical synthesis of deoxyoligonucleotides by the phosphoramidite method. In Methods in Enzymology, Chapter 15, 154:287-313, 1987.

Caruthers. Gene synthesis machines: DNA chemistry and its uses. Science. 230(4723):281-5, 1985.

Caruthers, The Chemical Synthesis of DNA/RNA: Our Gift to Science. J. Biol. Chem., 288(2):1420-1427, 2013.

Casmiro, Danilo R. et al., "PCR-based gene synthesis and protein NMR spectroscopy", Structure, 5(11):1407-1412, 1997.

Cello, et al. Chemical synthesis of poliovirus cDNA: generation of infectious virus in the absence of natural template. Science. 297(5583):1016-8, 2000.

Chalmers, et al. Scaling up the ligase chain reaction-based approach to gene synthesis. Biotechniques. 30(2):249-52, 2001.

Chan, et al. Natural and engineered nicking endonucleases—from cleavage mechanism to engineering of strand-specificity. Nucleic Acids Res. 39(1):1-18, 2011.

Chen, et al. Chemical modification of gene silencing oligonucleotides for drug discovery and development. Drug Discov Today. 10(8):587-93 2005.

Chen et al., Programmable chemical controllers made from DNA, Nat. Nanotechnol., 8(10):755-762, 2013.

Cheng, et al. High throughput parallel synthesis of oligonucleotides with 1536 channel synthesizer. Nucleic Acids Res. 30(18):e93, 2002.

Cho, et al. Capillary passive valve in microfluidic systems. NSTI-Nanotech. 2004; 1:263-266.

Chrisey et al., Fabrication of patterned DNA surfaces Nucleic Acids Research, 24(15):3040-3047 (1996).

Chung et al., One-step preparation of competent*Escherichia coli*:Transformation and storage of bacterial cells in the same solution. Proc Natl Acad Sci U S A. Apr. 1989;86(7):2172-2175.

Church et al., Next-generation digital information storage in DNA. Science, 337:6102, 1628-1629, 2012.

Cleary et al., "Production of complex nucleic acid libraries using highly parallel n s tu oligonucleotide synthesis," Nature Methods, 1(13):241-248, 2004.

Cohen et al., Human population: The next half century. Science, 302:1172-1175, 2003.

Crick. On protein synthesis. Symp Soc Exp Biol12:138-163,1958.

Cutler, David J. et al., "High-throughput variation detection and genotyping using microarrays", Genome Research, vol. 11, 1913-19 (2001).

Dahl, et al. Circle-to-circle amplification for precise and sensitive DNA analysis. Proc Natl Acad Sci U S A. Mar. 30, 2004;101(13):4548-53. Epub Mar. 15, 2004.

De Mesmaeker, et al. Backbone modifications in oligonucleotides and peptide nucleic acid systems. Curr Opin Struct Biol. Jun. 1995;5(3):343-55.

Deamer, David W. et al., "Characterization of nucleic acids by nanopore analysis", Acc. Cham. Res., vol. 35, No. 10, 817-825 (2002).

Deaven, The Human Genome Project: Recombinant clones for mapping and sequencing DNA. Los Alamos Science, 20:218-249, 1992.

Deng et al., Targeted bisulfite sequencing reveals changes in DNA methylation associated with nuclear reprogramming Nature Biotechnology, 27:352-360 (2009).

Dietrich, Rudiger.et al., "Gene assembly based on blunt-ended double-stranded DNA-modules", Biotechnology Techniques, vol. 12, No. 1, 49-54 (Jan. 1998).

Dormitzer et al., Synthetic generation of influenza vaccine viruses for rapid response to pandemics. Sci Translational Medicine, 5(185):185ra68, 14 pages, 2013.

Doudna et al. Genome editing. The new frontier ofgenome engineering with CRISPR-Cas9. Science 346(6213):1258096-1-1258096-9, 2014.

Dower et al., High efficiency transformation of *E. coli* by high voltage electroporation. Nucleic Acids Res. 16(13):6127-45 (1988).

Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.

Drmanac, et al. Human genome sequencing using unchained base reads on self-assembling DNA nanoarrays. Science. Jan. 1, 2010;327(5961):78-81.doi: 10.1126/science.1181498. Epub Nov. 5, 2009.

Droege and Hill, The Genome Sequencer FLXTM System-Longer reads, more applications, straight forward bioinformatics and more complete data sets Journal of Biotechnology, 136:3-10, 2008.

Duffy, et al. Rapid Prototyping of Microfluidic Systems in Poly(dimethylsiloxane). Anal Chem. Dec. 1, 1998;70(23):4974-84. doi: 10.1021/a0980656z.

Duggan, et al. Expression profiling using cDNA microarrays. Nat Genet. Jan. 1999;21(1 Suppl):10-4.

Eadie, et al. Guanine modification during chemical DNA synthesis. Nucleic Acids Res. Oct. 26, 1987;15(20):8333-49.

Eisen, Jonathan A., "A phylogenomic study of the MutS family of proteins", Nucleic Acids Research, vol. 26, No. 18, 4291-4300 (1998).

Ellis, et al. DNA assembly for synthetic biology: from parts to pathways and beyond. Integr Biol (Camb). Feb. 2011;3(2):109-18. doi: 10.1039/00ib00070a. Epub Jan. 19, 2011.

El-Sagheer, et al. Biocompatible artificial DNA linkerthat is read through by DNA polymerases and is functional in *Escherichia coli*. Proc Natl Acad Sci U S A. Jul. 12, 2011;108(28):11338-43. doi:10.1073/pnas.1101519108. Epub Jun. 27, 2011.

Elsik et al., The Genome sequence of taurine cattle: A window of ruminant biology and evolution. Science, 324:522-528, 2009.

Elsner et al., 172 nm excimer VUV-triggered photodegradation and micropatterning of aminosilane films, Thin Solid Films, 517:6772-6776 (2009).

Engler, et al. A one pot, one step, precision cloning method with high throughput capability. PLoS One. 2008;3(11):e3647. doi: 10.1371/journal.pone.0003647. Epub Nov. 5, 2008.

Engler, et al. Golden gate shuffling: a one-pot DNA shuffling method based on type IIs restriction enzymes. PLoS One. 2009;4(5):e5553. doi: 10.1371/journal.pone.0005553. Epub May 14, 2009.

Erlich and Zielinski, DNA fountain enables a robust and efficient storage architecture. Science, 355(6328):950-054, 2017.

European Patent Application No. 14834665.3 extended European Search Report dated Apr. 28, 2017.

Evans et al., DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided.

Fahy, et al. Self-sustained sequence replication (3SR): an isothermal transcription-based amplification system alternative to PCR. PCR Methods Appl. Aug. 1991;1(1):25-33.

Fedoryak, Olesya D. et al., "Brominated hydroxyquinoline as a photolabile protecting group with sensitivity to multiphoton excitation", Org. Lett., vol. 4, No. 2, 3419-3422 (2002).

Ferretti et al., Total synthesis of a gene for bovine rhodopsin. PNAS, 83:599-603 (1986).

(56) References Cited

OTHER PUBLICATIONS

Finger et al., The wonders of Flap Endonucleases: Structure, function, mechanism and regulation. Subcell Biochem., 62:301-326, 2012.
Fodor et al. "Light-Directed, Spatially Addressable Parallel Chemical Synthesis," Science, 251(4995):767-773, 1991.
Fogg et al., Structural basis for uracil recognition by archaeal family B DNA polymerases. Nature Structural Biology, 9(12):922-927, 2002.
Foldesi, et al. The synthesis of deuterionucleosides. Nucleosides Nucleotides Nucleic Acids. Oct.-Dec. 2000;19(10-12):1615-56.
Frandsen, et al. Efficient four fragment cloning forthe construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.
Frandsen. The User Friendly technology. User cloning. Oct. 7, 2010, 2 pages. http://www.rasmusfrandsen.dk/user_cloning.htm.
Fullwood et al., Next-generation DNA sequencing of paired-end tags [PET] for transcriptome and genome analysis Genome Research, 19:521-532, 2009.
Galneder. et al., Microelectrophoresis of a bilayer-coated silica bead in an optical trap: application to enzymology. Biophysical Journal, vol. 80, No. 5, 2298-2309 (May 2001).
Gao, et al. A flexible light-directed DNA chip synthesis gated by deprotection using solution photogenerated acids. Nucleic Acids Res. Nov. 15, 2001;29(22):4744-50.
Gao, et al. Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj, et al. Graphene as a subnanometre trans-electrode membrane. Nature. Sep. 9, 2010;467(7312):190-3. doi: 10.1038/nature09379.
Garbow, Norbert et al., "Optical tweezing electroghoresis of isolated, highly charged colloidal spheres", Colloids and Surfaces A: Physiochem. Eng. Aspects, vol. 195, 227-241 (2001).
GeneArt Seamless Cloning and Assembly Kits. Life Technologies Synthetic Biology. 8 pages, available online Jun. 15, 2012.
Genomics 101. An Introduction to the Genomic Workflow. 2016 edition, 64 pages. Available at: http://www.frontlinegenomics.com/magazine/6757/genomics-101/.
Geu-Flores, et al. User fusion: a rapid and efficient method for simultaneous fusion and cloning of multiple PCR products. Nucleic Acids Res. 2007;35(7):e55. Epub Mar. 27, 2007.
Gibson Assembly. Product Listing. Application Overview. 2 pages, available online Dec. 16, 2014.
Gibson, et al. Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Goldman et al., Towards practical, high-capacity, low-maintenance information storage in synthesized DNA, Nature, 494(7435):77-80, 2013.
Gosse, Charlie et al. "Magnetic tweezers: micromanipulation and force measurement at the molecular level", Biophysical Journal, vol. 8, 3314-3329 (Jun. 2002).
Grass, et al., Robust chemical preservation ofdigital information on DNA in silica with error-correcting codes, Angew. Chemie—Int. Ed., 54(8):2552-2555, 2015.
Greagg et al., A read-ahead function in archaeal DNA polymerases detects promutagenic template-strand uracil. Proc. Nat. Acad. Sci. USA, 96:9045-9050, 1999.
Grovenor. Microelectronic materials. Graduate Student Series in Materials Science and Engineering. Bristol, England: Adam Hilger, 1989; p. 113-123.
Gu et al., Depletion of abundant sequences by hybridization (DASH): using Cas9 to remove unwanted high-abundance species in sequencing libraries and molecular counting applications. Genome Biology, 17:41, 13 pages, 2016.

Haber, Charbel et al., Magnetic tweezers for DNA micromanipulation, Rev. Sci. Instrum., vol. 71, No. 12, 4561-4570 (Dec. 2000).
Hanahan and Cold Spring Harbor Laboratory, Studies on transformation of *Escherichia coli* with plasmids J. Mol. Biol. 166:557-580 (1983).
Hanahan et al., Plasmid transformation of *Escherichia coli* and other bacteria. Methods Enzymol, vol. 204, p. 63-113 (1991).
Harada, et al. Unexpected substrate specificity of T4 DNA ligase revealed by in vitro selection. Nucleic Acids Res. May 25, 1993;21(10):2287-91.
Heckers Karl H. et al., "Error analysis of chemically synthesized polynucleotides", BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al., "DNAWorks: an automated method for designing oligonucleotides for PCR-based gene synthesis", Nucleic Acids Research, vol. 30, No. 10, e43, 7 pages (2002).
Hosu, Basarab G. et al., Magnetic tweezers for intracellular applications•, Rev. Sci. Instrum., vol. 74, No. 9, 4158-4163 (Sep. 2003).
Huang, Hayden et al., "Three-dimensional cellular deformation analysis with a two-photon magnetic manipulator workstation", Biophysical Journal, vol. 82, No. 4, 2211-2223 (Apr. 2002).
Hughes, et al. Expression profiling using microarrays fabricated by an ink-jet oligonucleotide synthesizer. Nat Biotechnol. Apr. 2001;19(4):342-7.
Hughes et al. Principles of early drug discovery. Br J Pharmacol 162(2):1239-1249, 2011.
Hutchison, et al. Cell-free cloning using phi29 DNA polymerase. Proc Natl Acad Sci U S A. Nov. 29, 2005;102(48):17332-6. Epub Nov. 14, 2005.
In-Fusion Cloning: Accuracy, Not Background. Cloning & Competent Cells, ClonTech Laboratories, 3 pages, available online Jul. 6, 2014.
Jackson, Brian A. et al., "Recognition of DNA base mismatches by a rhodium intercalator", J. Am. Chem. Soc., vol. 19, 12986-12987 (1997).
Jacobs and Schar, DNA glycosylases: ln DNA repair and beyond Chromosome, 121:1-20 (2012)—http://www.ncbi.nlm.nih.gov/pmc/articles/PMC3260424/.
Jinek et al., A Programmable dual-RNA-guided DNA endonuclease in adaptive bacterial immunity. Science, 337:816-821, 2012.
Karagiannis and Ei-Osta, RNA interference and potential therapeutic applications of short interfering RNAs Cancer Gene Therapy, 12:787-795, 2005.
Ke, Song-Hua et al., "Influence of neighboring base pairs on the stability of single base bulges and base pairs in a DNA fragment", Biochemistry, Vo. 34, 4593-4600 (1995).
Kelley, Shana, et al. Single-base mismatch detection based on charge transduction through DNA, Nucleic Acids Research, vol. 27, No. 24, 4830-4837 (1999).
Kim et al., High-resolution patterns ofquantum dots formed by electrohydrodynamic jet printing for light-emitting diodes. Nano Letters, 15:969-973, 2015.
Kim, Yang-Gyun et al., "Chimeric restriction endonuclease", Proc. Natl. Acad. Sci. USA, vol. 91, 883-887 (Feb. 1994).
Kim, Yang-Gyun, "The interaction between Z-ONA and the Zab domain of double-stranded RNA adenosine deaminase characterized using fusion nucleases", The Journal of Biological Chemistry, vol. 274, No. 27, 19081-19086 (1999).
Kim, Yan~Gyun et al., "Site-specific cleavage ofDNA-RNA hybrids by zinc finger/Fok I cleavage domain fusions" Gene, vol. 203, 43-49 (1997).
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011
Kodumal, et al. Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.
Koike-Yusa et al., Genome-wide recessive genetic screening in mammalian cells with a lentiviral CRISPR-guide RNA library.

(56) References Cited

OTHER PUBLICATIONS

Nature Biotechnology, 32:267-273, 2014 (with three pages of supplemental "Online Methods").
Kong et al., Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp, Martin U. et al., "Chemical amplification: continuous-flow PCR on a chip", Science, vol. 280, 1046-1048 (May 15, 1998).
Kosuri and Church, "Large-scale de novo DNA synthesis: technologies and applications," Nature Methods, 11:499-507, 2014. Available at: http://www.nature.com/nmeth/journal/v11/n5/full/nmeth.2918.html.
Kosuri, et al. A scalable gene synthesis by selective amplification of DNA pools from high-fidelity microchips. Nature Biotechnology. 2010; 28:1295-1299.
Krayden, Inc., A Guide to Silane Solutions. Silane coupling agents. 7 pages. Published on May 31, 2005 at: http://krayden.com/pdf/xia_silane_chemistry.pdf.
Lagally, E.T. et al., "Single-molecule DNA amplification and analysis in an integrated microfluidic device" Anal. Chem., vol. 73, No. , 565-570 (Feb. 1, 2001).
Lahue, R.S. et al., "DNA mismatch correction in a defined system", Science, vol. 425; No. 4914, 160-164 (Jul. 14, 1989).
Lambrinakos, A. et al., "Reactivity of potassium permanganate and tetraethylammonium chloride with mismatched bases and a simple mutation detection protocol",Nucleic Acids Research, vol. 27, No.8, 1866-1874 (1999).
Landegren, et al. A ligase-mediated gene detection technique. Science. Aug. 26, 1988;241(4869):1077-80.
Lang, Matthew J. et al., "An automated two-dimensional optical force clamp for single molecule studies", Biophysical Journal, vol. 83, 491-501 (Jul. 2002).
Lashkari, et al. An automated multiplex oligonucleotide synthesizer: development of high-throughput, low-cost DNA synthesis. Proc Natl Acad Sci U S A. Aug. 15, 1995;92(17):7912-5.
Lausted et al., "POSaM: a fast, flexible, open-source, inkjet oligonucleotide synthesizer and microarrayer," Genome Biology, 5:R58, 17 pages, 2004. available at https://www.ncbi.nlm.nih.gov/pmc/articles/PMC507883/.
Leamon, et al. A massively parallel PicoTiterPlate based platform for discrete picoliter-scale polymerase chain reactions. Electrophoresis. Nov. 2003;24(21):3769-77.
Lee, Covalent end-immobilization of oligonucleotides onto solid surfaces. Thesis submitted to the Department of Chemical Engineering in Partial Fulfillment of the Requirements for the Degree of Doctor of Philosophy in Chemical Engineering at the Massachusetts Institute of Technology. Aug. 2001, 315 pages.
Lee, C.S. et al., "Microelectromagnets forthe control of magnetic nanoparticles", Appl. Phys. Lett., vol. 79, No. 20, 3308-3310 (Nov. 12, 2001).
Lee, et al. A microfluidic oligonucleotide synthesizer. Nucleic Acids Research 2010 vol. 38(8):2514-2521. DOI: 10.1093/nar/gkq092.
Leproust, et al. Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomic%20Services/Agilent_DNA_Microarray_Platform.ashx.
Leproust et al., "Synthesis of high-quality libraries of long (150mer) oligonucleotides by a novel depurination controlled process," Nucleic Acids Research, 35(8):2522-2540, 2010.
Lesnikowski, et al. Nucleic acids and nucleosides containing carboranes. J. Organometallic Chem. 1999; 581:156-169.
Leumann. DNA analogues: from supramolecular principles to biological properties. Bioorg Med Chem. Apr. 2002;10(4):841-54.
Levene, et al. Zero-mode waveguides for single-molecule analysis at high concentrations. Science. Jan. 31, 2003;299(5607):682-6.
Lewontin and Harti, Population genetics in forensic DNA typing. Science, 254:1745-1750, 1991.
Limbachiya et al., Natural data storage: A review on sending information from now to then via Nature. ACM Journal on Emerging Technologies in Computing Systems, V(N):Article A, May 19, 2015, 17 pages.
Link Technologies. "Product Guide 2010." Nov. 27, 2009, 136 pages. XP055353191. Retrieved from the Internet: URL:http://www.linktech.co.uk/documents/517/517.pdf.
Lipshutz, Robert J. et al., "High density synthetic oligonucleotide arrays", Nature Genetics Supplement, vol. 21, 20-24 (Jan. 1999).
Lishanski, Alia et al., "Mutation detection by mismatch binding protein, MutS, in amplified DNA: application to the cystic fibrosis gene", Proc. Natl. Acad. Sci. USA, vol. 91, 2674-2678 (Mar. 1994).
Liu et al., Comparison of Next-Generation Sequencing Systems. Journal of Biomedicine and Biotechnology, 11 pages, 2012.
Liu, et al. Enhanced Signals and Fast Nucleic Acid Hybridization by Microfluidic Chaotic Mixing. Angew. Chem. Int. Ed. 2006; 45:3618-3623.
Liu et al., Rational design of CXCR4 specific antibodies with elongated CDRs. JACS, 136:10557-10560, 2014.
Lizardi, et al. Mutation detection and single-molecule counting using isothermal rolling-circle amplification. Nat Genet. Jul. 1998;19(3):225-32.
Li, Lin et al., "Functional domains in Fok I restriction endonuclease", Proc. Natl. Acad. Sci. USA, 89:4275-4279, 1992.
Lu, A.-Lien et al., "Methyl-directed repair of DNA base-pair mismatches in vitro", Proc. Natl. Acad. Sci. USA, 80:4639-4643, 1983.
Lund, et al. A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.
Ma, et al. DNA synthesis, assembly and application in synthetic biology. Current Opinion in Chemical Biology. 16:260-267, 2012.
Ma et al., Versatile surface functionalization of cyclic olefin copolymer (COC) with sputtered Si02 thin film for potential BioMEMS applications. Journal of Materials Chemistry, 11 pages, 2009.
Mahato et al., Modulation of gene expression by antisense and antigene oligodeoxynucleotides and small interfering RNA Expert Opin. Drug Delivery, 2(1):3-28, 2005.
Margulies, et al. Genome sequencing in open microfabricated high-density picolitre reactors. Nature. 437(7057):376-80, 2005.
Matteucci, et al. Synthesis of deoxyoligonucleotides on a polymer support. J. Am. Chem. Soc. 103(11):3185-3191, 1981.
Matzas et al., Next generation gene synthesis by targeted retrieval of bead-immobilized, sequence verified DNA clones from a high throughput pyrosequencing device. Nat. Biotechnol., 28(12):1291-1294, 2010.
McBride & Caruthers, "An investigation of several deoxynucleoside phosphoramidites useful for synthesizing deoxyoligonucleotides." Tetrahedron Lett. 24: 245-248, 1983.
McGall, et al. Light-directed synthesis of high-density oligonucleotide arrays using semiconductor photoresists. Proc Natl Acad Sci U S A. 93(24):13555-60, 1996.
McGall, et al. The Efficiency of Light-Directed Synthesis of DNA Arrays on Glass Substrates. J. Am. Chem. Soc. 119(22):5081-5090, 1997.
Mei et al., Cell-free protein synthesis in microfluidic array devices Biotechnol. Prog., 23(6):1305-1311, 2007.
Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages. http://www.diva-portal.org/smash/get/diva2:161926/FULLTEXT01.pdf.
Meyers and Friedland, Knowledge-based simulation of genetic regulation in bacteriophage lambda. Nucl. Acids Research, 12(1):1-16, 1984.
Milo and Phillips, Numbers here reflect the number of protein coding genes and excludes tRNA and non-coding RNA. Cell Biology by the Numbers, p. 286, 2015.

(56) References Cited

OTHER PUBLICATIONS

Mitra, et al. In situ localized amplification and contact replication of many individual DNA molecules. Nucleic Acids Res. 27(24):e34, 1999.
Morin et al., Profiling the HeLa S3 transcriptome using randomly primed cDNA and massively parallel short-read sequencing. Biotechniques, 45:81-94, 2008.
Morris and Stauss, Optimizing T-cell receptor gene therapy for hematologic malignancies. Blood, 127(26):3305-3311, 2016.
Muller, Caroline et al. "Protection and labelling of thymidine by a fluorescent photolabile group", Helvetica Chimica Acta, vol. 84, 3735-3741 (2001).
Nakatani, Kazuhiko et al., "Recognition of a single guanine bulge by 2-Acylamino-1,8-naphthyridine", J. Am. Chem. Soc., vol. 122, 2172-2177 (2000).
Neiman M.S,. Negentropy principle in information processing systems. Radiotekhnika, 1966, No. 11, p. 2-9.
Neiman M.S., On the bases of the theory of information retrieval. Radiotekhnika, 1967, No. 5, p. 2-10.
Neiman M.S., On the molecular memory systems and the directed mutations. Radiotekhnika, 1965, No. 6, pp. 1-8.
Neiman M.S., On the relationships between the reliability, performance and degree of microminiaturization at the molecular-atomic level. Radiotekhnika, 1965, No. 1, pp. 1-9.
Neiman M.S., Some fundamental issues of microminiaturization. Radiotekhnika, 1964, No. 1, pp. 3-12.
Nishikura, A short primer on RNAi: RNA-directed RNA polymerase acts as a key catalyst Cell, 107:415-418, 2001.
Nour-Eldin, et al. User Cloning and User Fusion: The Ideal Cloning Techniques for Small and Big Laboratories. Plant Secondary Metabolism Engineering. Methods in Molecular Biology vol. 643, 2010, pp. 185-200.
Ochman, et al. Genetic applications of an inverse polymerase chain reaction. Genetics. Nov. 1988;120(3):621-3.
Organick et al., Random access in large-scale DNA data storage. Nature Biotechnology, Advance Online Publication, 8 pages, 2018.
Organick et al., Scaling up DNA data storage and random access retrieval, bioRxiv, preprint first posted online Mar. 7, 2017, 14 pages.
Pan, et al. An approach for global scanning of single nucleotide variations. Proc Natl Acad Sci U S A. Jul. 9, 2002;99(14):9346-51.
Pankiewicz. Fluorinated nucleosides. Carbohydr Res. Jul. 10, 2000;327(1-2):87-105.
PCT/US14/049834 International Preliminary Report on Patentability dated Feb. 18, 2016.
PCT/US2014/049834 International Search Report and Written Opinion dated Mar. 19, 2015.
PCT/US2014/049834, "Invitation to Pay Additional Fees and, where applicable, protest fee," dated Jan. 5, 2015.
PCT/US2015/043605 International Preliminary Report on Patentability dated Feb. 16, 2017.
PCT/US2015/043605 International Search Report and Written Opinion dated Jan. 6, 2016.
PCT/US2015/043605 Invitation to Pay Additional Fees dated Oct. 28, 2015.
PCT/US2016/016459 International Preliminary Report on Patentability dated Aug. 17, 2017.
PCT/US2016/016459 International Search Report and Written Opinion dated Apr. 18, 2016.
PCT/US2016/016636 International Preliminary Report on Patentability dated Aug. 17, 2017.
PCT/US2016/016636 International Search Report and Written Opinion dated May 2, 2016.
PCT/US2016/028699 International Preliminary Report on Patentability dated Nov. 2, 2017.
PCT/US2016/028699 International Search Report and Written Opinion dated Jul. 29, 2016.
PCT/US2016/031874 International Preliminary Report on Patentability dated Nov. 23, 2017.
PCT/US2016/031674 International Search Report and Written Opinion dated Aug. 11, 2016.
PCT/US2016/052336 International Search Report and Written Opinion dated Dec. 7, 2016.
PCT/US2016/052916 International Search Report and Written Opinion dated Dec. 30, 2016.
PCT/US2016/064270 International Search Report and Written Opinion dated Apr. 28, 2017.
PCT/US2017/026232 International Search Report and Written Opinion dated Aug. 28, 2017.
PCT/US2017/036868 International Search Report and Written Opinion dated Aug. 11, 2017.
PCT/US2017/045105 International Search Report and Written Opinion dated Oct. 20, 2017.
PCT/US2017/052305 International Search Report and Written Opinion dated Feb. 2, 2018.
Pease, et al. Light-generated oligonucleotide arrays tor rapid DNA sequence analysis. Proc Natl Acad Sci U S A. May 24, 1994;91(11):5022-6.
Peisajovich, et al. BBF RFC 28; A method for combinatorial muiti-part assembly based on the type-lis restriction enzyme aarl. Sep. 16, 2009, 7 pages.
Pellois, et al. "Individually addressable parallel peptide synthesis on microchips". Nature Biotechnology, vol. 20, 922-926 (Sep. 2002).
Petersen, et al. LNA: a versatile fool for therapeufics and genomics. Trends Biotechnol. Feb. 2003;21(2):74-81.
Pierce and Wangh, Linear-after-the-exponential polymerase chain reaction and allied technologies Real-time detection strategies for rapid, reliable diagnosis from single cells Methods Mol. Med. 132:65-85 (2007) (Abstract only).
Pirrung. How to make a DNA chip. Angew. Chem. Int. Ed., 41:1278-1289, 2002.
Plesa et al., Multiplexed gene synthesis in emulsions for exploring protein functional landscapes. Science, 10.1126/science.aa05167, 10 pages, 2018.
Pon. Solid-phase supports for oligonucleotide synthesis. Methods Mol Biol. 1993;20:465-96.
Poster. Reimagine Genome Scale Research. 2016, 1 page. Available at http://www2.twistbioscience.com/Oligo_Pools_CRISPR_poster.
Powers et al. Optimal strategies forthe chemical and enzymatic synthesis of bihelical deoxyribonucleic acids. J Am Chem Soc., 97(4):875-884, 1975.
Pray. "Discovery of DNA Structure and Function: Watson and Crick," Nature Education, 2008, 6 pages. available at: http://www.nature.com/scitable/topicpage/discovery-of-dna-structure-and-function-watson-397.
Prodromou, et al. Recursive PCR: a novel technique fortotal gene synthesis. Protein Eng. Dec. 1992;5(8):827-9.
Qian and Winfree, Scaling up digital circuit computation with DNA strand displacement cascades. Science, 332(6034):196-1201, 2011.
Qian, et al., Neural network computation with DNA strand displacement cascades, Nature, 475(7356):368-372, 2011.
Quan et al., "Parallel on-chip gene synthesis and application to optimization of protein expression," Nature Biotechnology, 29(5):449-452, 2011.
Rafalski and Morgante, Corn and humans: recombination and linkage disequilibrium in two genomes of similar size. Trends in Genetics, 20(2):103-111, 2004.
Raje and Murma, A Review of electrohydrodynamic-inkjet printing technology. International Journal of Emerging Technology and Advanced Engineering, 4(5):174-183, 2014.
Rastegari, et al., XNOR-Net: ImageNet Classification Using Binary Convolutional Neural Networks, in ECCV 2016, Part IV, LNCS 9908, p. 525-542, 2016.
Reimagine SequenceSpace, Reimagine Research, Twist Bioscience, Product Brochure, Published Apr. 6, 2016 online at: www2.twistbioscience.com/TB_Product_Brochure_04.2016, 8 pages.
RF Electric discharge type excimer lamp. Products Catalog. Excimer lamp light source "flat excimer," 16 pages dated Jan. 2016. From: http://www.hamamatsu.com/jp/en/product/category/1001/3026/index.html.

(56) References Cited

OTHER PUBLICATIONS

Richmond, et al. Amplification and assembly of chip-eluted DNA (AACED): a method for high-throughput gene synthesis. Nucleic Acids Res. Sep. 24, 2004;32(17):5011-8. Print 2004.
Roche. Restriction Enzymes from Roche Applied Science-A Tradition of Premium Quality and Scientific Support. FAQS and Ordering Guide. Roche Applied Science. Accessed Jan. 12, 2015, 37 pages.
Rogozin et al., Origin and evolution of spliceosomal introns. Biology Direct, 7:11, 2012.
Ruminy, et al., "Long-range identification of hepatocyte nuclear factor-3 (FoxA) high and low-affinity binding Sites with a chimeric nuclease", J. Mol. Bioi., vol. 310, 523-535 (2001).
Saaem et al., In situ synthesis of DNA microarray on functionalized cyclic olefin copolymer substrate ACS Applied Materials & Interfaces, 2(2):491-497, 2010.
Saboulard, et al. High-throughput site-directed mutagenesis using oligonucleotides synthesized on DNA chips. Biotechniques. Sep. 2005;39(3):363-8.
Sacconi, L. et al., Three-dimensional magneto-optic trap for microobject manipulation, Optics Letters, vol. 26, No. 17, 1359-1361 (Sep. 1, 2001).
Saiki et al. Analysis of enzymatically amplified beta-globin and HLA-DQ alpha DNA with allele-specific oligonucleotide probes. Nature 324:163-166 (1986).
Sandhu, et al. Dual asymmetric PCR: one-step construction of synthetic genes. Biotechniques. Jan. 1992;12(1):14-6.
Sargolzaei et al., Extent of linkage disequilibrium in Holstein cattle in North America. J.Dairy Science, 91:2106-2117, 2007.
Schaller, et al. Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing et al. Microchip electrophoresis: a method for highspeed SNP detection. Nucleic Acids Res 28(9):E43 (2000).
Schmitt et al., New strategies in engineering T-cell receptor genemodified T cells to more effectively target malignancies. Clinical Cancer Research, 21(23):5191-5197, 2015.
Seelig, et al., Enzyme-Free Nucleic Acid Logic Circuits, Science 314(5805):1585-1588, 2006.
Sharpe and Mount, Genetically modified T cells in cancertherapy: opportunities and challenges. Disease Models and Mechanisms, 8:337-350, 2015.
Sierzchala, Agnieszka B. et al., "Solid-phase oligodeoxynucleotide synthesis : a two-step cycle using peroxy anion eprotection", J. Am. Chem. Soc., vol. 125, No. 44, 13427-13441 (2003).
Simonyan and Zisserman, Very Deep Convolutional Networks for Large-Scale Image Recognition, Published as a conference paper at Int. Conf. Learn. Represent., pp. 1-14, 2015.
Singh-Gasson, Sangeet et al., Maskless fabrication of light-directed olxyonucleotide microarrays using a digital micromirror array, Nature Biotechnology, vol. 17, 974-978 (Oct. 1999).
Smith, et al. Generating a synthetic genome by whole genome assembly: phiX174 bacteriophage from synthetic oligonucleotides. Proc Natl Acad Sci U S A. Dec. 23, 2003;100(26):15440-5. Epub Dec. 2, 2003.
Smith, et al. Generation of cohesive ends on PCR products by UDG-mediated excision of dU, and application for cloning into restriction digest-linearized vectors. PCR Methods Appl. May 1993;2(4):328-32.
Smith, Jane et al., "Mutation detection with MutH, MutL, and MutS mismatch repair proteins", Proc. Natl. Acad. Sci. USA, vol. 93, 4374-4379 (Apr. 1996).
Smith Jane et al., "Removal of Polymerase-Produced mutant sequences from PCR products", Proc. Natl. Acad. Sci. USA, vol. 94, 6847-6850 (Jun. 1997).
Smith, Steven B. et al., "Direct mechanical measurements of the elasticity of single DNA molecules using magnetic beads", Science, vol. 258, 1122-1126 (Nov. 13, 1992).
Soni, et al. Progress toward ultrafast DNA sequencing using solidstate nanopores. Clin Chem. Nov. 2007;53(11):1996-2001.
Southern, et al. Analyzing and comparing nucleic acid sequences by hybridization to arrays of oligonucleotides: evaluation using experimental models. Genomics. Aug. 1992;13(4):1008-17.
Sproat, et al. An efficient method forthe isolation and purification of oligoribonucleotides. Nucleosides & Nucleotides. 1995; 14(1&2):255-273.
Srivannavit et al., Design and fabrication of microwell array chips for a solution-based, photogenerated acid-catalyzed parallel oligonuclotide DNA synthesis. Sensors and Actuators A, 116:150-160, 2004.
Srivastava et al., "RNA synthesis: phosphoramidites for RNA synthesis in the reverse direction. Highly efficient synthesis and application to convenient introduction of ligands, chromophores and modifications of synthetic RNA at the 3'-end", Nucleic Acids Symposium Series, 52(1):103-104, 2008.
Steel, The Flow-Thru Chip A Three-dimensional biochip platform. In: Schena, Microarray Biochip Technology, Chapter 5, Natick, MA: Eaton Publishing, 2000, 33 pages.
Stemmer, et al. Single-step assembly of a gene and entire plasmid from large numbers of oligodeoxyribonucleotides. Gene. Oct. 16, 1995;164(1):49-53.
Stryer. "DNA Probes and genes can be synthesized by automated solid-phase methods." Biochemistry, 3rd edition, New York: W.H. Freeman and Company, 1988; 123-125.
Stutz, et al. Novel fluoride-labile nucleobase-protecting groups for the synthesis of 3'(2')-O-amino-acylated RNA sequences. Helv. Chim. Acta. 2000; 83(9):2477-2503.
Takahashi, Cell-free cloning using multiply-primed rolling circle amplification with modified RNA primers. Biotechniques. Jul. 2009;47(1):609-15.
Tanase, M. et al., "Magnetic trapping of multicomponent nanowires", The Johns Hopkins University, Baltimore, Maryland, p. 1-3 (Jun. 25, 2001).
Taylor et al., Impact of surface chemistry and blocking strategies on DNA microarrays. Nucleic Acids Research, 31(16):e87, 19 pages, 2003.
The Hood Laboratory, "Beta Group." Assembly Manual forthe POSaM: The ISB Piezoelelctr Oligonucleotide Synthesizer and Microarrayer, Inkjet Microarrayer Manual Version 1.2, 50 pages, May 28, 2004.
The SLIC, Gibson, CPEC and SLiCE assembly methods (and GeneArt Seamless, In-Fusion Cloning). 5 pages, available online Sep. 2, 2010.
Tian, et al. Accurate multiplex gene synthesis from programmable DNA microchips. Nature. Dec. 23, 2004;432(7020):1050-4.
Tsal et al., Dimeric CRISPR RNA-guided FokI nucleases for highly specific genome editing Nat. Biotechnol., 32(6):569-576, 2014.
Unger, et al. Monolithic microfabricated valves and pumps by multilayer soft lithography. Science. Apr. 7, 2000;288(5463):113-6.
U.S. Appl. No. 14/241,874 Office Action dated Feb. 27, 2017.
U.S. Appl. No. 14/452,429 Notice of Allowance dated Jun. 7, 2016.
U.S. Appl. No. 14/452,429 Restriction Requirement dated Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/135,434 Notice of Allowance dated Feb. 9, 2018.

(56) References Cited

OTHER PUBLICATIONS

U.S. Appl. No. 15/135,434 Office Action dated Nov. 30, 2017.
U.S. Appl. No. 15/135,434 Restriction Requirement dated Jul. 12, 2017.
U.S. Appl. No. 15/154,879 Notice of Allowance dated Feb. 1, 2017.
U.S. Appl. No. 15/187,721 Notice of Allowance dated Dec. 7, 2018.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Office Action dated Mar. 21, 2017.
U.S. Appl. No. 15/245,054 Office Action dated Oct. 19, 2018.
U.S. Appl. No. 15/377,547 Office Action dated Mar. 24, 2017.
U.S. Appl. No. 15/377,547 Office Action dated Nov. 30, 2017.
U.S. Appl. No. 15/602,991 Notice of Allowance dated Oct. 25, 2017.
U.S. Appl. No. 15/602,991 Office Action dated Sep. 21, 2017.
U.S. Appl. No. 15/603,013 Office Action dated Jan. 30, 2018.
U.S. Appl. No. 15/603,013 Office Action dated Oct. 20, 2017.
U.S. Appl. No. 15/682,100 Office Action dated Jan. 2, 2018.
U.S. Appl. No. 15/682,100 Restriction Requirement dated Nov. 8, 2017.
U.S. Appl. No. 14/452,429 Office Actian dated Apr. 9, 2015.
Vaijayanthi, et al. Recent advances in oligonucleotide synthesis and their applications. Indian J Biochem Biophys. 40(6):377-91, 2003.
Van Den Brulle, et al. A novel solid phase technology for high-throughput gene synthesis. Biotechniques. 45(3):340-343, 2008.
Van Tassell et al., SNP discovery and allele frequency estimation by deep sequencing of reduced representation libraries. Nature Methods, 5:247-252, 2008.
Vargeese, et al. Efficient activation of nucleoside phosphoramidites with 4,5-dicyanoimidazole during oligonucleotide synthesis. Nucleic Acids Res. 26(4):1046-50, 1998.
Verma et al. Modified oligonucleotides: synthesis and strategy for users. Annu Rev Biochem 67:99-134, 1998.
Vincent, et al. Helicase-dependent isothermal DNA amplification. EMBO Rep. 5(8):795-800, 2004.
Visscher et al., "Construction of multiple-beam optical traps with nanometer-resolution position sensing", IEEE Journal of Selected Topics in Quantum Electronics, 2(4):1066-1076, 1996.
Voldmans Joel et al., "Holding forces of single-particle dielectrophoretic traps." Biophysical Journal, 80(1):531-541, 2001.
Vos, et al. AFLP: A new technique for DNA fingerprinting. Nucleic Acids Res. 23(21):4407-14, 1995.
Wagner et al., "Nucleotides, Part LXV, Synthesis of 2'-Deoxyribonucleoside 5'-Phosphoramidites: New Building Blocks for the Inverse (5'-3')-Oiigonucleotide Approach." Helvetica Chimica Acta, 83(8):2023-2035, 2000.
Wah, David A. et al., "Structure of Fok I has implications for DNA cleavage", Proc. Natl. Acad. Sci. USA, 95:10564-10569, 1998.
Wah, David A. et al., "Structure of the multimodular endonuclease Fok I bound to DNA", Nature, 388:97-100, 1997.
Walker, et al. Strand displacement amplification—an isothermal, in vitro DNA amplification technique. Nucleic Acids Res. 20(7):1691-6, 1992.
Wan et al., Deep Learning for Content-Based Image Retrieval: A comprehensive study. in Proceedings of the 22nd ACM International Conference on Multimedia—Nov. 3-7, 2014, Orlando, FL, p. 157-166, 2014.
Weber, et al. A modular cloning system for standardized assembly of multigene constructs. PLoS One. 6(2):e16765, 2011.
Welz, et al. 5-(Benzylmercapto)-1H-tetrazole as activator for 2'-O-TBDMS phosphoramidite building blocks in RNA synthesis. Tetrahedron Lett. 43(5):795-797, 2002.
Westin et al., Anchored multiplex amplification on a microelectronic chip array Nature Biotechnology, 18:199-202, 2000 (abstract only).
Whitehouse, Adrian et al. "Analysis ofthe mismatch and insertion/deletion binding properties of Thermus thermophilus, HB8, MutS", Biochemical and Biophysical Research Communications, vol. 233, 834-837, 1997.
Wiedenheft et al., RNA-guided genetic silencing systems in bacteria and archaea. Nature, 482:331-338, 2012.
Wijshoff, Herman. Structure and fluid-dynamics in Piezo inkjet printheads. Thesis. Venio, The Netherlands, published 2008, p. 1-185.
Wirtz, Denis, "Direct measurement ofthe transport properties of a single DNA molecule", Physical Review Letters, vol. 75, No. 12, 2436-2439, 1995.
Withers-Martinez, Chrislaine et al., "PCR-based gene synthesis as an efficient approach for expression of the A+ T-rich malaria genome", Protein Engineering, 12(12):1113-1120, 1999.
Wood, Richard D. et al., "Human DNA repair genes", Science 291:1284-1289, 2001.
Wosnick, et al. Rapid construction of large synthetic genes: total chemical synthesis of two different versions of the bovine prochymosin gene. Gene. 60(1):115-27, 1987.
Wright and Church, An open-source oligomicroarray standard for human and mouse. Nature Biotechnology, 20:1082-1083, 2002.
Wu, et al. RNA-mediated gene assembly from DNA arrays. Angew Chem Int Ed Engl. 51(19):4628-32, 2012.
Wu, et al. Specificity ofthe nick-closing activity of bacteriophage T4 DNA ligase. Gene. 76(2):245-54, 1989.
Wu, Xing-Zheng et al., "An improvement of the on-line electrophoretic concentration method for capillary electrophoresis of proteins an experimental factors affecting he concentration effect", Analytical Sciences, 16:329-331, 2000.
Xiong, et al. A simple, rapid, high-fidelity and cost-effective PCR-based two-step DNA synthesis method for long gene sequences. Nucleic Acids Res. 32(12):e98, 2004.
Xiong et al., Chemical gene synthesis: Strategies, softwares, error corrections, and applications. FEMS Microbiol. Rev., 32:522-540, 2008.
Xiong, et al. Non-polymerase-cycling-assembly-based chemical gene synthesis: Strategies, methods, and progress. Biotechnology Advances. 26(2):121-134, 2008.
Xu et al., Design of 240,000 orthogonal 25mer DNA barcode probes. PNAS, 106(7):2289-2294, 2009.
Yang, et al "Purification, cloning, and characterization of the CEL I nuclease", Biochemistry, 39(13):3533-35, 2000.
Yazdi, et al., A Rewritable, Random-Access DNA-Based Storage System, Scientific Reports, 5, Article No. 14138, 27 pages, 2015.
Yehezkel et al., De novo DNA synthesis using single molecule PCR Nucleic Acids Research, 36(17):e107, 2008.
Yes HMDS vapor prime process application note Prepared by UC Berkeley and University of Texas at Dallas and re-printed by Yield Engineering Systems, Inc., 6 pages (http://www.yieldengineering.com/Portals/0/HMDS%20Application%20Note.pdf (Published online Aug. 23, 2013).
Youil, Rima et al., "Detection of 81 of 81 known mouse Beta-Giobin promoter mutations with T4 Endonuclease VII• The EMC Method", Genomics, 32:431-435, 1996.
Young, et al. Two-step total gene synthesis method. Nucleic Acids Res. 32(7):e59, 2004.
Zhang and Seelig, Dynamic DNA nanotechnology using strand-displacement reactions, Nat. Chem., 3(2):103-113, 2011.
Zheleznaya, et al. Nicking endonucleases. Biochemistry (Mosc). 74(13):1457-66, 2009.
Zhirnov et al., Nucleic acid memory. Nature Materials, 15:366, 2016.
Zhou et al., Microfluidic PicoArray synthesis of oligodeoxynucleotides and simultaneous assembling of multiple DNA sequences Nucleic Acids Research, 32(18):5409-5417, 2004.
Eroshenko et al.: Gene Assembly from Chip-Synthesized Oligonucleotides; Current Protocols in Chemical biology 4: 1-17 (2012).
European Patent Application No. 16871446.7 First Official Action dated Nov. 13, 2019.
Galka et al.: QuickLib, a method for building fully synthetic plasmid libraries by seamless cloning of degenerate oligonucleotides. PLOS One, 12, e0175146:1-9 (2017).

(56) References Cited

OTHER PUBLICATIONS

Galka et al.: QuickLib, a method for building fully synthetic plasmid libraries by seamless cloning of degenerate oligonucleotides. PLOS One, 12, e0175146:S1 figure (2017).
Galka et al.: QuickLib, a method for building fully synthetic plasmid libraries by seamless cloning of degenerate oligonucleotides. PLOS One, 12, e0175146:S1 Table (2017).
Galka et al.: QuickLib, a method for building fully synthetic plasmid libraries by seamless cloning of degenerate oligonucleotides. PLOS One, 12, e0175146:S2 figure (2017).
International Application No. PCT/US2018/019268 International Preliminary Report on Patentability dated Sep. 6, 2019.
International Application No. PCT/US2019/032992 International Search Report and Written Opinion dated Oct. 28, 2019.
International Application No. PCT/US2019/032992 Invitation to Pay Additional Fees dated Sep. 6, 2019.
Paul et al.: Acid binding and detritylation during oligonucleotide synthesis. Nucleic Acids Research. 15. pp. 3048-3052 (1996).
Pierce et al.: Linear-after-the-exponential polymerase chain reaction and allied technologies. Real-time detection strategies for rapid, reliable diagnosis from single cells. Methods Mol Med. 2007;132:65-85.
PubChem Data Sheet Acetonitrile. Printed from website https://pubchem.ncbi.nlm.nig.gov/ pp. 1-124 (2020).
PubChem Data Sheet Methylene Chloride. Printed from website https://pubchem.ncbi.nlm.nih.gov/ pp. 1-140 (2020).
Rajpal et al.: A general method for greatly improving the affinity of antibodies by using combinatorial libraries. Proc. Natl. Acad. Sci. 102(24):8466-8471 (2005).
Solomon et al.: Genomics at Agilent: Driving Value in DNA Sequencing.https://www.agilent.com/labs/features/2010_genomics.html, 8 pages (Aug. 5, 2010).
U.S. Appl. No. 14/241,874 Final Office Action dated Jan. 28, 2019.
U.S. Appl. No. 15/015,059 Office Action dated Aug. 19, 2019.
U.S. Appl. No. 15/151,316 Office Action dated Oct. 4, 2019.
U.S. Appl. No. 15/156,134 Final Office Action dated Jan. 3, 2020.
U.S. Appl. No. 15/187,714 Final Office Action dated Sep. 17, 2019.
U.S. Appl. No. 15/268,422 Final Office Action dated Oct. 3, 2019.
U.S. Appl. No. 15/603,013 Final Office Action dated Nov. 6, 2019.
U.S. Appl. No. 15/619,322 Final Office Action dated Mar. 30, 2020.
U.S. Appl. No. 15/619,322 Office Action dated Aug. 14, 2019.
U.S. Appl. No. 15/816,995 Office Action dated Sep. 20, 2019.
U.S. Appl. No. 15/835,342 Office Action dated Dec. 2, 2019.
U.S. Appl. No. 15/835,342 Restriction Requirement dated Sep. 10, 2019.
U.S. Appl. No. 15/844,395 Office Action dated Jan. 24, 2020.
U.S. Appl. No. 15/921,479 Office Action dated Nov. 12, 2019.
U.S. Appl. No. 15/960,319 Office Action dated Aug. 16, 2019.
U.S. Appl. No. 15/991,992 Restriction Requirement dated Mar. 10, 2020.
U.S. Appl. No. 16/006,581 Office Action dated Sep. 25, 2019.
U.S. Appl. No. 16/165,952 Office Action dated Mar. 12, 2020.
U.S. Appl. No. 16/239,453 Office Action dated Nov. 7, 2019.
U.S. Appl. No. 16/384,678 Office Action dated Jan. 21, 2020.
U.S. Appl. No. 16/409,608 Office Action dated Sep. 9, 2019.
U.S. Appl. No. 16/530,717 Office Action dated Sep. 6, 2019.
U.S. Appl. No. 16/535,777 Office Action dated Jan. 23, 2020.
U.S. Appl. No. 16/535,779 First Action Interview dated Feb. 10, 2020.
U.S. Appl. No. 15/921,537 Office Action dated Apr. 1, 2020.
Acevedo-Rocha et al. Directed evolution of stereoselective enzymes based on genetic selection as opposed to screening systems. J. Biotechnol. 191:3-10 (2014).
Arand et al. Structure of Rhodococcus erythropolis limonene-1,2-epoxide hydrolase reveals a novel active site. EMBO J. 22:2583-2592 (2003).
Assembly manual for the POSaM: The ISB Piezoelelctric Oligonucleotide Synthesizer and Microarrayer, The Institute for Systems Biology, May 28, 2004 (50 pages).
Carter and Friedman, DNA synthesis and Biosecurity: Lessons learned and options forthe future. J. Craig Venter Institute, La Jolla, CA, 28 pages, Oct. 2015.
CeGaT. Tech Note available at https://www.cegat.de/web/wp-content/uploads/2018/06/Twist-Exome-Tech-Note.pdf (4 pgs.) (2018).
Chilamakuri et al. Performance comparison of four exome capture systems for deep sequencing. BMC Genomics 15(1):449 (2014).
Cruse et al. Atlas of Immunology, Third Edition. Boca Raton: CRC Press (pp. 282-283) (2010).
De Silva et al. New Trends of Digital Data Storage in DNA. BioMed Res Int. 2016:8072463 (2016).
Dillon et al. Exome sequencing has higher diagnostic yield compared to simulated disease-specific panels in children with suspected monogenic disorders. Eur J Hum Genet 26(5):644-651 (2018).
Dvorsky. Living Bacteria Can Now Store Data. Gizmodo internet publication. Retrieved from https://gizmodo.com/living-bacteria-can-now-store-data-1781773517 (4 pgs) (Jun. 10, 2016).
European Patent Application No. 12827479.2 Extended European Search Report dated May 18, 2015.
European Patent Application No. 12827479.2 Partial European Search Report dated Jan. 29, 2015.
European Patent Application No. 14834665.3 Further Examination Report dated Nov. 28, 2018.
European Patent Application No. 14834665.3 Office Action dated May 2, 2018.
European Patent Application No. 16847497.1 Extended European Search Report dated Jan. 9, 2019.
European Patent Application No. 16871446.7 European Search Report dated Apr. 10, 2019.
Gao et al. A method forthe generation of combinatorial antibody libraries using pIX phage display. PNAS 99(20):12612-12616 (2002).
Gibson et al. Creation ofa Bacterial Cell Controlled by A Chemically Synthesized Genome. Science 329(5989):52-56 (2010).
Goldfeder et al. Medical implications of technical accuracy in genome sequencing. Genome Med 8(1):24 (2016).
Han et al. Linking T-cell receptor sequence to functional phenotype at the single-cell level. Nat Biotechnol 32(7):684-692 (2014).
Imgur: The magic of the internet. Uploaded May 10, 2012, 2 pages, retrieved from: https://imgur.com/mEWuW.
International Application No. PCT/US2017/026232 International Preliminary Report on Patentability dated Feb. 26, 2019.
International Application No. PCT/US2017/045105 International Preliminary Report on Patentability dated Feb. 5, 2019.
International Application No. PCT/US2017/052305 International Preliminary Report on Patentability dated Apr. 30, 2019.
International Application No. PCT/US2017/062391 International Preliminary Report on Patentability dated May 21, 2019.
International Application No. PCT/US2018/050511 International Search Report and Written Opinion dated Jan. 11, 2019.
International Application No. PCT/US2018/057857 International Search Report and Written Opinion dated Mar. 18, 2019.
International Application No. PCT/US2019/012218 International Search Report and Written Opinion dated Mar. 21, 2019.
Jacobus et al. Optimal cloning of PCR fragments by homologous recombination in *Escherichia soli*. PLoS One 10(3):e0119221 (2015).
Jager et al. Simultaneous Humoral and Cellular: Immune Response against Cancer—Testis Antigen NY-ES0-1: Definition of Human Histocompatibility LeukocyteAntigen (HLA)-A2—binding Peptide Epitopes. J. Exp. Med. 187(2):265-270 (1998).
Li et al., Beating bias in the directed evolution of proteins: Combining high-fidelity on-chip solid-phase gene synthesis with efficient gene assembly for combinatorial library construction. First published Nov. 24, 2017, 2 pages. retrieved from: https://doi.org/10.1002/cbic.201700540.
Li et al. Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).
Light source unit for printable patterning VUV-Aligner / USHIO Inc., Link here: https://www.ushio.co.jp/en/products/1005.html, published Apr. 25, 2016, printed from the internet on Aug. 2, 2016, 3 pages.

(56) References Cited

OTHER PUBLICATIONS

Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).
Meynert et al. Quantifying single nucleotide variant detection sensitivity in exome sequencing. BMC Bioinformatics 14:195 (2013).
Meynert et al. Variant detection sensitivity and biases in whole genome and exome sequencing. BMC Bioinformatics 15:247 (2014).
Mulligan. Commercial Gene Synthesis Technology PowerPoint presentation. BlueHeron® Biotechnology. Apr. 5, 2006 (48 pgs).
Jo et al.: Engineering therapeutic antibodies targeting G-protein-coupled receptors; Experimental & Molecular Medicine; 48; 9 pages (2016).
Lausted et al.: POSaM: a fast, flexible, open-source, inkjet oligonucleotide synthesizer and microarrayer; Genome Biology 2004, 5:R58.
Douthwaite et al.: Affinity maturation of a novel antagonistic human monoclonal antibody with a long VH CDR3 targeting the Class A GPCR formyl-peptide receptor 1; mAbs, vol. 7, Iss. 1, pp. 152-166 (Jan. 1, 2015).
PCT/IL2012/000326 International Preliminary Report on Patentability dated Dec. 5, 2013.
PCT/IL2012/000326 International Search Report dated Jan. 29, 2013.
PCT/US2016/052336 International Preliminary Report on Patentability dated Mar. 29, 2018.
PCT/US2016/052916 International Preliminary Report on Patentability dated Apr. 5, 2018.
PCT/US2016/064270 International Preliminary Report on Patentability dated Jun. 14, 2018.
PCT/US2017/062391 International Search Report and Written Opinion dated Mar. 28, 2018.
PCT/US2017/066847 International Search Report and Written Opinion dated May 4, 2018.
PCT/US2018/022487 International Search Report and Written Opinion dated Aug. 1, 2018.
PCT/US2018/022493 International Search Report and Written Opinion dated Aug. 1, 2018.
PCT/US2018/037152 International Search Report and Written Opinion dated Aug. 28, 2018.
PCT/US2018/037161 International Search Report and Written Opinion dated Oct. 22, 2018.
PCT/US2018/037161 Invitation to Pay Additional Fees dated Aug. 27, 2018.
PCT/US2018/056783 International Search Report and Written Opinion of the International Searching Authority dated Dec. 20, 2018.
PCT/US2018/19268 International Search Report and Written Opinion dated Jun. 26, 2018.
PCT/US2018/19268 Invitation to Pay Additional Fees and, where applicable, protest fee dated May 2, 2018.
PCT/US2018/22487 Invitation to Pay Additional Fees and, where applicable, protest fee dated May 31, 2018.
PCT/US2018/22493 Invitation to Pay Additional Fees and, where applicable, protest fee dated May 31, 2018.
Puigbo. Optimizer: a web server for optimizing the codon usage of DNA sequences. Nucleic Acid Research, 35(14):126-131, 2007.
Sharan et al.: Recombineering: a homologous recombination-based method of genetic engineering. Nat Profile 4(2):1-37 (originally pp. 206-223) (2009).
Skerra. Phosphorothioate primers improve the amplification of DNA sequences by DNA polymerases with proofreading activity. Nucleic Acids Res. Jul. 25, 1992; 20(14):3551-4.
Martinez-Torrecuadradaet al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).
U.S. Appl. No. 15/187,714 Office Action dated Apr. 4, 2019.
U.S. Appl. No. 15/603,013 Office Action dated Jun. 26, 2019.
Sullivan et al.: Library construction and evaluation for site saturation mutagenesis. Enzyme Microb. Technol. 53:70-77 (2013).
Sun et al.: Structure-Guided Triple-Code Saturation Mutagenesis: Efficient Tuning ofthe Stereoselectivity of an Epoxide Hydrolase. ACS Catal. 6:1590-1597 (2016).
Twist Bioscience | White Paper. DNA-Based Digital Storage. Retrieved from the internet, Twistbioscience.com, Mar. 27, 2018, 5 pages.
U.S. Appl. No. 14/241,874 Office Action dated Jul. 14, 2016.
U.S. Appl. No. 14/241,874 Office Action dated May 4, 2018.
U.S. Appl. No. 14/885,965 Office Action dated Aug. 28, 2018.
U.S. Appl. No. 15/015,059 Final Office Action dated Jul. 17, 2019.
U.S. Appl. No. 15/015,059 Office Action dated Feb. 7, 2019.
U.S. Appl. No. 15/151,316 Office Action dated Jun. 7, 2018.
U.S. Appl. No. 15/156,134 Office Action dated Apr. 4, 2019.
U.S. Appl. No. 15/187,714 Restriction Requirement dated Sep. 17, 2018.
U.S. Appl. No. 15/268,422 Office Action dated Mar. 1, 2019.
U.S. Appl. No. 15/268,422 Restriction Requirement dated Oct. 4, 2018.
U.S. Appl. No. 15/377,547 Final Office Action dated Feb. 8, 2019.
U.S. Appl. No. 15/377,547 Office Action dated Jul. 27, 2018.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/602,991 Final Office Action dated Dec. 13, 2018.
U.S. Appl. No. 15/602,991 Office Action dated May 31, 2018.
U.S. Appl. No. 15/602,991 Office Action dated May 31, 2019.
U.S. Appl. No. 15/603,013 Office Action dated Jul. 10, 2018.
U.S. Appl. No. 15/709,274 Notice of Allowance dated Apr. 3, 2019.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/816,995 Restriction Requirement dated Apr. 4, 2019.
U.S. Appl. No. 15/844,395 Restriction Requirement dated May 17, 2019.
U.S. Appl. No. 15/860,445 Final Office Action dated Dec 13, 2018.
U.S. Appl. No. 15/860,445 Office Action dated May 30, 2018.
U.S. Appl. No. 15/921,479 Restriction Requirement dated May 24, 2019.
U.S. Appl. No. 15/151,316Final Office Action dated Feb. 21, 2019.
Van Der Werf et al.: Limonene-1,2-epoxide hydrolase from Rhodococcus erythropolis DCL14 belongs to a novel class of epoxide hydrolases. J. Bacteriol. 180:5052-5057 (1998).
Warr et al.: Exome Sequencing: current and future perspectives. G3: (Bethesda) 5(8):1543-1550 (2015).
Wu, et al.: Sequence-Specific Capture of Protein-DNA Complexes for Mass Spectrometric Protein Identification; PLoS One. Oct. 20, 2011, vol. 6, No. 10.
Zheng et al.: Manipulating the Stereoselectivity of Limonene Epoxide Hydrolase by Directed Evolution Based on Iterative Saturation Mutagenesis. J. Am. Chem. Soc. 132:15744-15751 (2010).
Zhou, et al.: Establishment and application ofa loop-mediated isothermal amplification (LAMP) system for detection of cry1Ac transgenic sugarcane Scientific Reports May 9, 2014, vol. 4, No. 4912.
Agbavwe et al.: Efficiency, Error and Yield in Light-Directed Maskless Synthesis of DNA Microarrays. Journal of Nanobiotechnology. 9(57):1-17 (2011).
De Graff et al.: Glucagon-Like Peptide-1 and its Class B G Protein-Coupled Receptors: A Long March to Therapeutic Successes. Pharmacol Rev. 68(4):954-1013 (2016).
Diehl et al.: BEAMING: single-molecule PCR on microparticles in water-in-oil emulsions. Nature Methods. 3(7):551-559 (2006).
PCT/US2020/052291 International Preliminary Report on Patentability dated Apr. 7, 2022.
PCT/US2020/052306 International Preliminary Report on Patentability dated Mar. 15, 2022.
U.S. Appl. No. 15/272,004 Office Action dated Apr. 13, 2022.
U.S. Appl. No. 15/921,479 Final Office Action dated Dec. 20, 2021.
U.S. Appl. No. 15/921,479 Office Action dated Apr. 28, 2022.

(56) References Cited

OTHER PUBLICATIONS

U.S. Appl. No. 16/128,372 Office Action dated Dec. 13, 2021.
U.S. Appl. No. 16/590,301 Restriction Requirement dated Apr. 28, 2022.
U.S. Appl. No. 16/712,678 Office Action dated Nov. 26, 2021.
U.S. Appl. No. 16/737,401 Office Action dated Jan. 5, 2022.
U.S. Appl. No. 16/737,401 Restriction Requirement dated Nov. 15, 2021.
U.S. Appl. No. 16/802,423 Restriction Requirement dated Dec. 29, 2021.
U.S. Appl. No. 16/802,439 Office Action dated Mar. 17, 2022.
U.S. Appl. No. 16/802,439 Restriction Requirement dated Oct. 1, 2021.
U.S. Appl. No. 16/854,719 Office Action dated Nov. 24, 2021.
U.S. Appl. No. 17/154,906 Office Action dated Nov. 10, 2021.
Williams et al.: Amplification of complex gene libraries by emulsion PCR. Nature Methods. 3(7):545-550(2006).
Altshuler et al.: Generation of Recombinant Antibodies and Means for Increasing Their Affinity. Biochemistry (Moscow). 75(13:1584-1605 (2010).
Damha et al.: An improved procedure forderivatization of controlled-pore glass beads for solidphase oligonucleotide synthesis. Nucleic Acids Research. 18(13):3813-3821 (1990).
PCT/US2022/023936 International Search Report and Written Opinion dated Jul. 14, 2022.
Smith et al.: Changing the peptide specificity of a human T-cell receptor by directed evolution. Nature Communications. 5:1-13 (2014).
Sommermeyer et al.: Minimal Amino Acid Exchange in Human TCR Constant Regions Fosters Improved Function of TCR Gene-Modified T Cells. Journal of Immunology. 184:6223-6231 (2010).
U.S. Appl. No. 16/737,401 Final Office Action dated Jun. 13, 2022.
U.S. Appl. No. 15/835,342 Office Action dated Jun. 17, 2022.
U.S. Appl. No. 16/039,256 Office Action dated May 10, 2022.
U.S. Appl. No. 16/417,023 Final Office Action dated Aug. 2, 2022.
U.S. Appl. No. 16/417,023 Office Action dated Feb. 22, 2022.
U.S. Appl. No. 16/590,301 Office Action dated Jul. 20, 2022.
U.S. Appl. No. 16/726,073 Office Action dated Jun. 30, 2022.
U.S. Appl. No. 16/802,423 Notice of Allowance dated Jul. 25, 2022.
U.S. Appl. No. 16/854,719 Office Action dated Jun. 2, 2022.
U.S. Appl. No. 17/154,906 Office Action dated May 17, 2022.
U.S. Appl. No. 17/180,614 Office Action dated Oct. 5, 2022.

* cited by examiner 10 um 21 um

1401

1401

1401

SEQUENCE LISTING

```
<160> NUMBER OF SEQ ID NOS: 28

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agacaatcaa ccatttgggg tggacagcct tgacctctag acttcggcat ttttttttt      60 tt                                                                    62

<210> SEQ ID NO 2
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
cgggatcctt atcgtcatcg tcgtacagat cccgacccat ttgctgtcca ccagtcatgc      60
tagccatacc atgatgatga tgatgatgag aaccccgcat tttttttttt tt             112

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
```

```
                            primer

<400> SEQUENCE: 3
atgcggggtt ctcatcatc                                                19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgggatcctt atcgtcatcg                                               20

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(6)
<223> OTHER INFORMATION: a, c, t, g, unknown or other

<400> SEQUENCE: 5
acnnnngtay c                                                        11

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(7)
<223> OTHER INFORMATION: a, c, t, g, unknown or other

<400> SEQUENCE: 6
acnnnnnctc c                                                        11

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atctatgtcg ggtgcggaga aagaggtaat                                    30

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other
```

```
<400> SEQUENCE: 8
caannnnngt gg                                                    12

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 9 cacnnnngtg                                                       10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 10 caynnnnrtg                                                       10

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, c, t, g, unknown or other

<400> SEQUENCE: 11
ccannnnnnn nntgg                                                 15

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 12
ccannnnnnt gg                                                    12

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 13 ccannnntg g                                                            11

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, c, t, g, unknown or other

<400> SEQUENCE: 14 ccnnnnnng g                                                            11

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 15
cctnnnnnag g                                                           11

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 16
cgannnnnnt gc                                                          12

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 17 gaannnnttc                                                             10
```

-continued

```
<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 18 gacnnnngtc                                                              10

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 19
gacnnnnngt c                                                            11

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 20
gacnnnnnng tc                                                           12

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 21 gatnnnnatc                                                              10

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other
```

```
<400> SEQUENCE: 22
gcannnnntg c                                                    11

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 23
gccnnnnngg c                                                    11

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, c, t, g, unknown or other

<400> SEQUENCE: 24
gcnnnnnnng c                                                    11

<210> SEQ ID NO 25
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, t, g, unknown or other

<400> SEQUENCE: 25
ggccnnnnng gcc                                                  13

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
taactataac ggtcctaagg tagcgaa                                   27

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
```
tagggataac agggtaat            18

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tggcaaacag ctattatggg tattatgggt            30

NUCLEIC ACID BASED DATA STORAGE USING ENZYMATIC BIOENCRYPTION

CROSS-REFERENCE

This application claims the benefit of U.S. Provisional Application No. 62/462,284 filed on Feb. 22, 2017, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 20, 2018, is named 44854-738_201_SL.txt and is 8,636 bytes in size.

BACKGROUND

Biomolecule based information storage systems, e.g., DNA-based, have a large storage capacity and stability over time. However, there is a need for scalable, automated, highly accurate and highly efficient systems for biomolecules for information storage. In addition, there is a need for protecting the security of such information.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

Provided herein are methods for storing information, the method comprising: (a) receiving at least one item of information in a form of at least one digital sequence; (b) receiving instructions for selection of at least one bioencryption format, wherein the bioencryption format is enzymatic, electromagnetic, chemical, or affinity based bioencryption; (c) converting the at least one digital sequence to a plurality of oligonucleotide sequences based on the selected bioencryption format; (d) synthesizing a plurality of oligonucleotides encoding for the oligonucleotide sequences; and (e) storing the plurality of oligonucleotides. Further provided herein are methods for storing information, wherein the enzymatic based bioencryption comprises CRISPR/Cas based bioencryption. Further provided herein are methods for storing information, wherein the enzymatic based bioencryption comprises instructions for synthesis of the oligonucleotides which are sensitive to an enzyme as set out in Table 1. Further provided herein are methods for storing information, wherein the electromagnetic based bioencryption comprises instructions for synthesis of the oligonucleotides which are sensitive to electromagnetic wavelengths of about 0.01 nm to about 400 nm. Further provided herein are methods for storing information, wherein the chemical based bioencryption comprises instructions for synthesis of the oligonucleotides which are sensitive to gaseous ammonia or methylamine administration. Further provided herein are methods for storing information, wherein the affinity based bioencryption comprises instructions for synthesis of the oligonucleotides which are sensitive to a sequence tag or affinity tag. Further provided herein are methods for storing information, wherein the affinity tag is biotin, digoxigenin, Ni-Nitrilotriacetic acid, desthiobiotin, histidine, polyhistidine, myc, hemagglutinin (HA), FLAG, a fluorescence tag, a tandem affinity purification (TAP) tag, glutathione S transferase (GST), a polynucleotide, an aptamer, an antigen, or an antibody. Further provided herein are methods for storing information, wherein 2, 3, 4, or 5 bioencryption formats are used. Further provided herein are methods for storing information, wherein the plurality of oligonucleotides comprises at least 100,000 oligonucleotides. Further provided herein are methods for storing information, wherein the plurality of oligonucleotides comprises at least 10 billion oligonucleotides.

Provided herein are methods for retrieving information, the method comprising: (a) releasing a plurality of oligonucleotides from a surface; (b) applying an enzymatic, electromagnetic, chemical, or affinity based decryption to the plurality of oligonucleotides; (c) enriching the plurality of oligonucleotides; (d) sequencing enriched oligonucleotides from the plurality of oligonucleotides to generate nucleic acid sequences; and (e) converting the nucleic acid sequences to at least one digital sequence, wherein the at least one digital sequence encodes for at least one item of information. Further provided herein are methods for retrieving information, wherein decryption of the plurality of oligonucleotides comprises applying a CRISPR/Cas complex to the plurality of oligonucleotides. Further provided herein are methods for retrieving information, wherein the enzymatic based decryption comprises applying an enzyme as set out in Table 1. Further provided herein are methods for retrieving information, wherein the electromagnetic based decryption comprises applying wavelengths of about 0.01 nm to about 400 nm. Further provided herein are methods for retrieving information, wherein the chemical based decryption comprises applying gaseous ammonia or methylamine administration. Further provided herein are methods for retrieving information, wherein the affinity based decryption comprises applying a sequence tag or affinity tag. Further provided herein are methods for retrieving information, wherein the affinity tag is biotin, digoxigenin, Ni-Nitrilotriacetic acid, desthiobiotin, histidine, polyhistidine, myc, hemagglutinin (HA), FLAG, a fluorescence tag, a tandem affinity purification (TAP) tag, glutathione S transferase (GST), a polynucleotide, an aptamer, an antigen, or an antibody. Further provided herein are methods for retrieving information, wherein 2, 3, 4, or 5 forms of decryption are used.

Provided herein are systems for storing information, the system comprising: (a) a receiving unit for receiving machine instructions for at least one item of information in a form of at least one digital sequence, and machine instructions for selection of at least one bioencryption format, wherein the bioencryption format is enzymatic, electromagnetic, chemical, or affinity based bioencryption; (b) a processor unit for automatically converting the at least one digital sequence to a plurality of oligonucleotide sequences based on the selected bioencryption format; (c) a synthesizer unit for receiving machine instructions from the processor unit for synthesizing a plurality of oligonucleotides encoding for the oligonucleotide sequences; and (d) a storage unit for receiving the plurality of oligonucleotides deposited from the synthesizer unit. Further provided herein are systems for storing information, wherein the enzymatic based bioencryption comprises CRISPR/Cas based bioencryption. Further provided herein are systems for storing information, wherein the enzymatic based bioencryption comprises machine instructions for synthesis of the oligonucleotides which are sensitive to an enzyme as set out in Table 1.

Further provided herein are systems for storing information, wherein the electromagnetic based bioencryption comprises machine instructions for synthesis of the oligonucleotides which are sensitive to electromagnetic wavelengths of about 0.01 nm to about 400 nm. Further provided herein are systems for storing information, wherein the chemical based bioencryption comprises machine instructions for synthesis of the oligonucleotides which are sensitive to gaseous ammonia or methylamine administration. Further provided herein are systems for storing information, wherein the affinity based bioencryption comprises instructions for synthesis of the oligonucleotides which are sensitive to a sequence tag or affinity tag. Further provided herein are systems for storing information, wherein the affinity tag is biotin, digoxigenin, Ni-Nitrilotriacetic acid, desthiobiotin, histidine, polyhistidine, myc, hemagglutinin (HA), FLAG, a fluorescence tag, a tandem affinity purification (TAP) tag, glutathione S transferase (GST), a polynucleotide, an aptamer, an antigen, or an antibody. Further provided herein are systems for storing information, wherein the plurality of oligonucleotides comprises at least 100,000 oligonucleotides. Further provided herein are systems for storing information, wherein the plurality of oligonucleotides comprises at least 10 billion oligonucleotides.

Provided herein are systems for retrieving information, the method comprising: (a) a storage unit comprising a plurality of oligonucleotides on a surface; (b) a deposition unit for applying an enzymatic, electromagnetic, chemical, or affinity based bioencryption to the plurality of oligonucleotides; (c) a sequencing unit for sequencing the plurality of oligonucleotides to obtain nucleic acid sequences; and (d) a processor unit for automatically converting the nucleic acid sequences to at least one digital sequence, wherein the at least one digital sequence encodes for at least one item of information. Further provided herein are systems for retrieving information, wherein the deposition unit applies CRISPR/Cas complex to the plurality of oligonucleotides. Further provided herein are systems for retrieving information, wherein the enzymatic based bioencryption comprises applying an enzyme as set out in Table 1. Further provided herein are systems for retrieving information, wherein the electromagnetic based bioencryption comprises applying wavelengths of about 0.01 nm to about 400 nm. Further provided herein are systems for retrieving information, wherein the chemical based bioencryption comprises applying gaseous ammonia or methylamine administration. Further provided herein are systems for retrieving information, wherein the affinity based bioencryption comprises a sequence tag or affinity tag. Further provided herein are systems for retrieving information, wherein the affinity tag is biotin, digoxigenin, Ni-Nitrilotriacetic acid, desthiobiotin, histidine, polyhistidine, myc, hemagglutinin (HA), FLAG, a fluorescence tag, a tandem affinity purification (TAP) tag, glutathione S transferase (GST), a polynucleotide, an aptamer, an antigen, or an antibody.

Provided herein are methods for storing information, the method comprising: (a) receiving at least one item of information in a form of at least one digital sequence; (b) receiving instructions for at least one form of bioencryption; (c) converting the at least one digital sequence to a plurality of bioencrypted oligonucleotide sequences; (d) synthesizing the plurality of bioencrypted oligonucleotide sequences; and (e) storing the plurality of oligonucleotides.

Provided herein are methods for storing information, the method comprising: (a) receiving at least one item of information in a form of at least one digital sequence; (b) receiving instructions for an enzymatic, electromagnetic, chemical, or affinity based bioencryption; (c) converting the at least one digital sequence to a plurality of bioencrypted oligonucleotide sequences; (d) synthesizing the plurality of bioencrypted oligonucleotide sequences; and (e) storing the plurality of oligonucleotides.

Provided herein are methods for storing information, the method comprising: (a) receiving at least one item of information in a form of at least one digital sequence; (b) converting the at least one digital sequence to a plurality of bioencrypted oligonucleotide sequences, wherein each of the bioencrypted oligonucleotide sequences comprise additional sequences encoded for removal by CRISPR/Cas complex; (c) synthesizing the plurality of bioencrypted oligonucleotide sequences; and (d) storing the plurality of oligonucleotides.

Provided herein are methods for retrieving information, the method comprising: (a) releasing a plurality of oligonucleotides from a surface; (b) applying at least one form of biodecryption to the plurality of oligonucleotides; (c) enriching the plurality of oligonucleotides, thereby selecting a plurality of enriched oligonucleotides; (d) sequencing the enriched oligonucleotides to generate nucleic acid sequences; and (e) converting the nucleic acid sequences to at least one digital sequence, wherein the at least one digital sequence encodes for at least one item of information.

Provided herein are methods for retrieving information, the method comprising: (a) releasing a plurality of oligonucleotides from a surface; (b) applying an enzymatic, electromagnetic, chemical, or affinity based decryption to the plurality of oligonucleotides; (c) enriching the plurality of oligonucleotides, thereby selecting a plurality of enriched oligonucleotides; (d) sequencing the enriched oligonucleotides to generate nucleic acid sequences; and (e) converting the nucleic acid sequences to at least one digital sequence, wherein the at least one digital sequence encodes for at least one item of information.

Provided herein are methods for retrieving information, the method comprising: (a) releasing a plurality of oligonucleotides from a surface; (b) applying as CRISPR/Cas complex to the plurality of oligonucleotides; (c) enriching the plurality of oligonucleotides, thereby selecting a plurality of enriched oligonucleotides; (d) sequencing the enriched oligonucleotides to generate nucleic acid sequences; and (e) converting the nucleic acid sequences to at least one digital sequence, wherein the at least one digital sequence encodes for at least one item of information.

Provided herein are systems for storing information, the system comprising: (a) a receiving unit for receiving machine instructions for at least one item of information in a form of at least one digital sequence, and machine instructions for at least one form of bioencryption; (b) a processor unit for converting the at least one digital sequence to a plurality of bioencrypted oligonucleotide sequences; (c) a synthesizer unit for receiving machine instructions from the processor unit for synthesizing the plurality of bioencrypted oligonucleotide sequences; and (d) a storage unit for receiving the plurality of oligonucleotides deposited from the synthesizer unit.

Provided herein are systems for storing information, the system comprising: (a) a receiving unit for receiving machine instructions for at least one item of information in a form of at least one digital sequence, and machine instructions for an enzymatic, electromagnetic, chemical, or affinity based bioencryption; (b) a processor unit for converting the at least one digital sequence to a plurality of bioencrypted oligonucleotide sequences; (c) a synthesizer unit for receiving machine instructions from the processor unit for synthesizing the plurality of bioencrypted oligonucleotide sequences; and (d) a storage unit for receiving the plurality of oligonucleotides deposited from the synthesizer unit.

Provided herein are systems for storing information, the system comprising: (a) a receiving unit for receiving machine instructions for at least one item of information in a form of at least one digital sequence, and machine instructions for bioencryption by CRISPR/Cas complex; (b) processor unit for converting the at least one digital sequence to a plurality of bioencrypted oligonucleotide sequences; (c) a synthesizer unit for receiving machine instructions from the processor unit for synthesizing the plurality of bioencrypted oligonucleotide sequences; and (d) a storage unit for receiving the plurality of oligonucleotides deposited from the synthesizer unit.

Provided herein are systems for retrieving information, the method comprising: (a) a storage unit comprising a plurality of oligonucleotides on a surface; (b) a deposition unit for applying at least one form of biodecryption to the plurality of oligonucleotides; (c) a sequencing unit for sequencing the plurality of oligonucleotides to obtain nucleic acid sequence; and (d) a processor unit for converting the nucleic acid sequences to at least one digital sequence, wherein the at least one digital sequence encodes for at least one item of information.

Provided herein are systems for retrieving information, the method comprising: (a) a storage unit comprising a plurality of oligonucleotides on a surface; (b) a deposition unit for applying at least an enzymatic, electromagnetic, chemical, or affinity based bioencryption to the plurality of oligonucleotides; (c) a sequencing unit for sequencing the plurality of oligonucleotides to obtain nucleic acid sequence; and (d) a processor unit for converting the nucleic acid sequences to at least one digital sequence, wherein the at least one digital sequence encodes for at least one item of information.

Provided herein are systems for retrieving information, the method comprising: (a) a storage unit comprising a plurality of oligonucleotides on a surface; (b) a deposition unit for applying CRISPR/Cas complex to the plurality of oligonucleotides; (c) a sequencing unit for sequencing the plurality of oligonucleotides to obtain nucleic acid sequence; and (d) a processor unit for converting the nucleic acid sequences to at least one digital sequence, wherein the at least one digital sequence encodes for at least one item of information.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Definitions

Unless defined otherwise, all technical and scientific terms used herein have the same meaning as is commonly understood by one of ordinary skill in the art to which these inventions belong.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The term "oligonucleotide" as used herein is used interchangeably with "oligonucleic acid." The terms "oligonucleotide" and "oligonucleic acid" encompass double- or triple-stranded nucleic acids, as well as single-stranded molecules.

Nucleic Acid Based Information Storage

Figure 1:
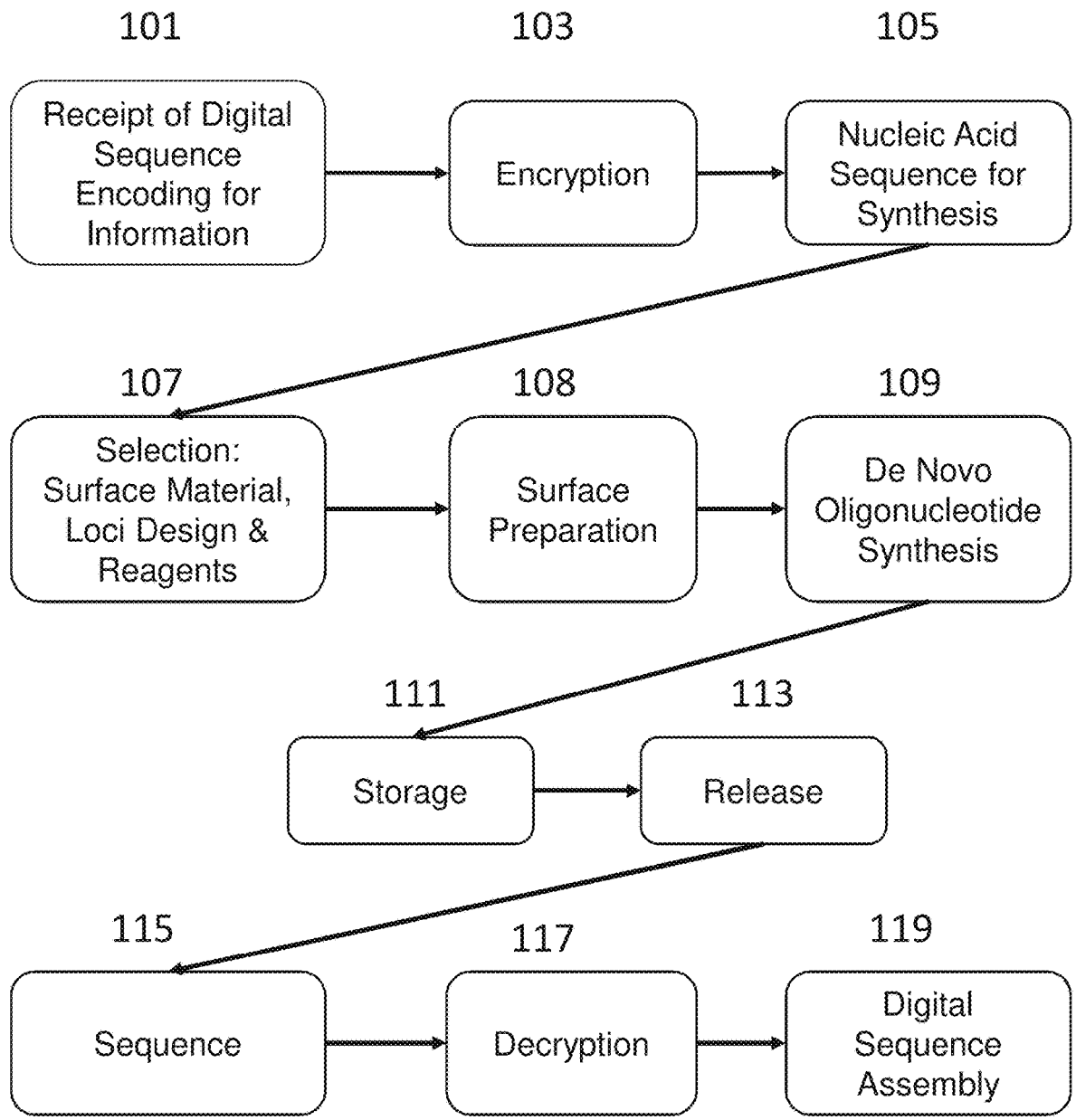
FIG. 1 illustrates an exemplary workflow for nucleic acid-based data storage.

Provided herein are devices, compositions, systems, and methods for nucleic acid-based information (data) storage. An exemplary workflow is provided in FIG. 1. In a first step, a digital sequence encoding an item of information (i.e., digital information in a binary code for processing by a computer) is received 101. An encryption 103 scheme is applied to convert the digital sequence from a binary code to a nucleic acid sequence 105. A surface material for nucleic acid extension, a design for loci for nucleic acid extension (aka, arrangement spots), and reagents for nucleic acid synthesis are selected 107. The surface of a structure is prepared for nucleic acid synthesis 108. De novo oligonucleotide synthesis is performed 109. The synthesized oligonucleotides are stored 111 and available for subsequent release 113, in whole or in part. Once released, the oligonucleotides, in whole or in part, are sequenced 115, and subject to decryption 117 to convert the nucleic sequence back to the digital sequence. The digital sequence is then assembled 119 to obtain an alignment encoding for the original item of information.

Figure 2:
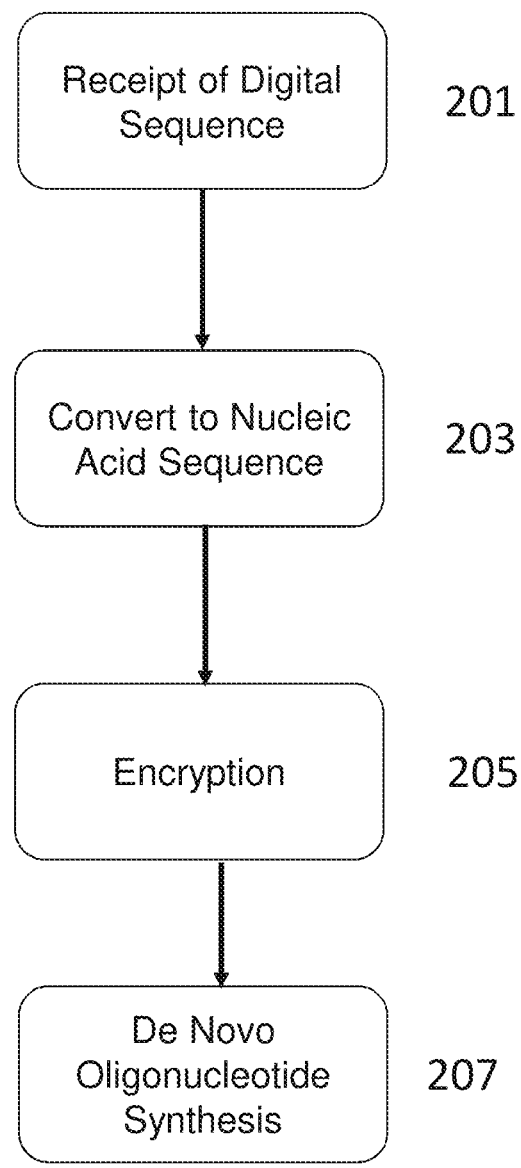
FIG. 2 illustrates an exemplary workflow for storage for bioencryption.

Further provided herein are methods and systems for secured DNA-based information storage including receipt of one or more digital sequences encoding for at least one item of information 201, conversion of the one or more digital sequences to a nucleic acid sequence 203, encryption of the nucleic acid sequence 205, and de novo oligonucleotide synthesis of the encrypted nucleic acid sequence 207. See FIG. 2.

Provided herein are devices, compositions, systems, and methods for nucleic acid-based information storage, wherein machine instructions are received for conversion from a digital sequence to a nucleic acid sequence, bioencryption, biodecryption, or a combination of any of these steps. Machine instructions may be received for desired items of information for conversion and for one or more types of bioencryption selected from a list of options, for example, without limitation, enzymatic based (e.g., CRISPR/Cas complex or restriction enzyme digest), electromagnetic radiation based (e.g., photolysis or photodetection), chemical cleavage (e.g, gaseous ammonia or methylamine treatment to cleave Thymidine-succinyl hexamide CED phosphoramidite (CLP-2244 from ChemGenes)), and affinity based (e.g., a sequence tag for hybridization, or incorporation of modified nucleotides with enhanced affinity to a capture reagent) forms of bioencryption. Following receipt of a particular bioencryption selection, a program module performs the step of converting the item of information to nucleic acid sequence and applying design instructions for design of a bioencrypted version of the sequence, before providing synthesis instructions to a material deposition device for de novo synthesis of oligonucleotides. In some instances, machine instructions for selection of one or more species within a category of bioencryption are provided.

Figure 3:
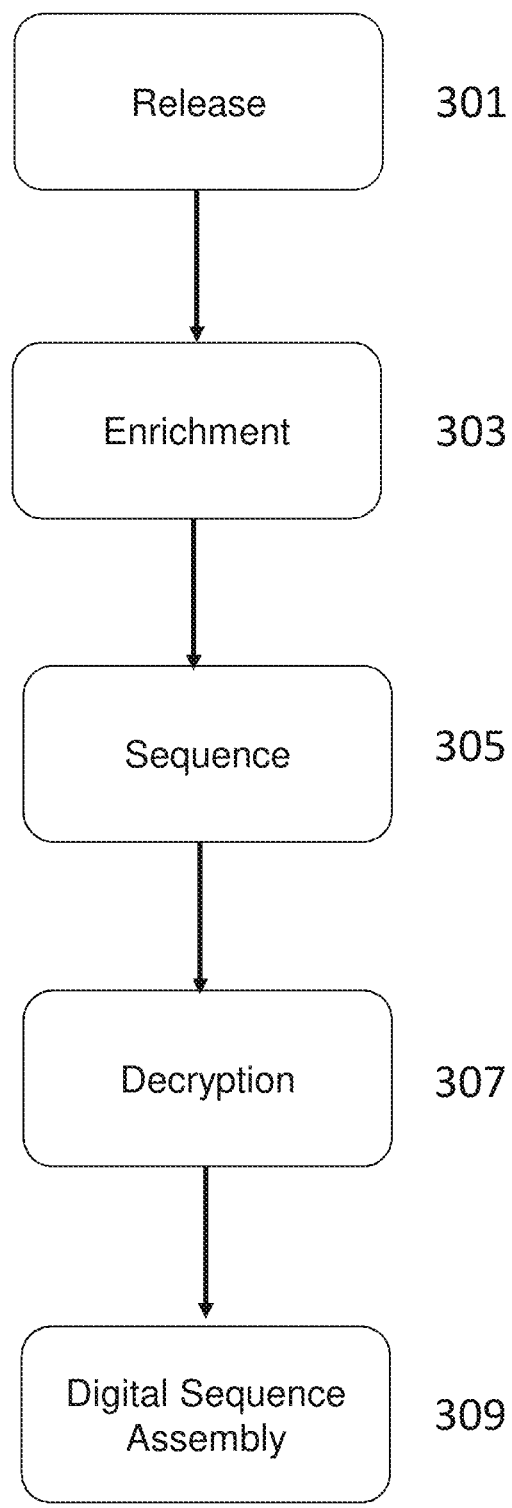
FIG. 3 illustrates an exemplary workflow for retrieval following bioencryption.

Further provided herein are methods and systems for secured DNA-based information retrieval including release of oligonucleotides from a surface 301, enrichment of desired oligonucleotides 303, sequencing of the oligonucleotides 305, decryption of the nucleic acid sequence 307, and assembly of one or more digital sequences encoding for an item of information 309. See FIG. 3.

Machine instructions as described herein may also be provided for biodecryption. Biodecryption may comprise receipt of machine instructions. Such instructions may include one or more formats of biodecryption selected from a list of options, for example, without limitation, enzymatic based (e.g., CRISPR/Cas complex or restriction enzyme digest), electromagnetic radiation based (e.g., photolysis or photodetection), chemical cleavage (e.g, gaseous ammonia or methylamine treatment to cleave Thymidine-succinyl hexamide CED phosphoramidite (CLP-2244 from ChemGenes)), and affinity based (e.g., nucleic acid sequences for hybridization, or incorporation of modified nucleotides with enhanced affinity to a capture reagent) forms of biodecryption of the oligonucleotides. Following receipt of a particular biodecryption selection, a program module performs the step releasing the modulatory agent(s) for enrichment of the oligonucleotides. Following enrichment, the oligonucleotides are sequenced, optionally aligned to a longer nucleic acid sequence, and converted to a digital sequence corresponding to an item of information. In some instances, machine instructions for selection of one or more species within a category of biodecryption are provided.

Items of Information

Optionally, an early step of a DNA data storage process disclosed herein includes obtaining or receiving one or more items of information in the form of an initial code (e.g., digital sequence). Items of information include, without limitation, text, audio and visual information. Exemplary sources for items of information include, without limitation, books, periodicals, electronic databases, medical records, letters, forms, voice recordings, animal recordings, biological profiles, broadcasts, films, short videos, emails, bookkeeping phone logs, internet activity logs, drawings, paintings, prints, photographs, pixelated graphics, and software code. Exemplary biological profile sources for items of information include, without limitation, gene libraries, genomes, gene expression data, and protein activity data. Exemplary formats for items of information include, without limitation, .txt, .PDF, .doc, .docx, .ppt, .pptx, .xls, .xlsx, .rtf, .jpg, .gif, .psd, .bmp, .tiff, .png, and .mpeg. The amount of individual file sizes encoding for an item of information, or a plurality of files encoding for items of information, in digital format include, without limitation, up to 1024 bytes (equal to 1 KB), 1024 KB (equal to 1 MB), 1024 MB (equal to 1 GB), 1024 GB (equal to 1TB), 1024 TB (equal to 1 PB), 1 exabyte, 1 zettabyte, 1 yottabyte, 1 xenottabyte or more. In some instances, an amount of digital information is at least or about 1 gigabyte (GB). In some instances, the amount of digital information is at least or about 1, 2, 3, 4, 5, 6, 7, 8, 9, 10, 20, 50, 100, 200, 300, 400, 500, 600, 700, 800, 900, 1000 or more than 1000 gigabytes. In some instances, the amount of digital information is at least or about 1 terabyte (TB). In some instances, the amount of digital information is at least or about 1, 2, 3, 4, 5, 6, 7, 8, 9, 10, 20, 50, 100, 200, 300, 400, 500, 600, 700, 800, 900, 1000 or more than 1000 terabytes. In some instances, the amount of digital information is at least or about 1 petabyte (PB). In some instances, the amount of digital information is at least or about 1, 2, 3, 4, 5, 6, 7, 8, 9, 10, 20, 50, 100, 200, 300, 400, 500, 600, 700, 800, 900, 1000 or more than 1000 petabytes.

Encryption

Biological Encryption and Decryption

Described herein are devices, compositions, systems, and methods comprising biological encryption (aka "bioencryption") following receipt of a digital sequence encoding an item of information. In addition to individual forms of bioencryption and biodecryption described herein, also provided herein are processes for incorporating the selection of one or more classes or species of masking a biological sequence into a workflow for information storage and/or retrieval.

Provided herein are devices, compositions, systems, and methods of target enrichment of a nucleic acid sequence of interest from a larger population of nucleic acid sequences comprising biological encryption. In some instances, biological encryption is used to enrich a target signal from noise. In some instances, the target signal is a nucleic acid sequence of interest. In some instances, biological encryption comprises introducing the nucleic acid sequence of interest into a larger population of nucleic acid sequences with known sequences. The known nucleic acid sequences can be referred to as encryption nucleic acid sequences. In some instances, the encryption nucleic acids are decrypted. In some instances, decryption of the known nucleic acid sequences results in an increase in signal-to-noise ratio of the nucleic acid sequence of interest.

Provided herein are devices, compositions, systems, and methods comprising incorporation of biological molecule encryption in an information storage and/or retrieval workflow. Exemplary forms of bioencryption and biodecryption include, without limitation, enzymatic based, electromagnetic radiation based, chemical cleavage, and affinity based bioencryption and biodecryption.

Provided herein are devices, compositions, systems, and methods comprising application of nuclease complex activity based encryption. Exemplary nucleases include, without limitation, a Cas nuclease (CRISPR associated), a Zinc Finger Nuclease (ZFNs), a Transcription Activator-Like Effector Nucleases, an Argonaute nuclease, S1 Nuclease, mung bean nuclease, or a DNAse. Exemplary Cas nucleases include, without limitation, Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, Cs0, Csf4, Cpf1, c2c1, and c2c3. In some instances, the Cas nuclease is Cas9. In some instances, a CRISPR/Cas complex provides for predetermined removal of one or more nucleic acid sequences. In some instances, enrichment steps described herein comprises depletion of abundant sequences by hybridization (DASH). In some instances, the DASH comprises application of a nuclease. For example, a nuclease such as Cas9, when bound to a CRISPR complex including a guide RNA ("gRNA") sequence, induces a stranded break such that a longer form of a nucleic acid sequence is no longer intact. In some instances, excised nucleic acids are unavailable for subsequent amplification following enrichment. In some instances, gRNA shepherds the Cas9 enzyme to a specific stretch of nucleic acids. In alternative arrangements, a gRNA has multiple sites for cleavage. A gRNA-based system allows for generation of an encryption code with high specificity and selectivity. For example, since a CRISPR/Cas9 based system uses 20 bp to identify a sequence to cleave, at least about 10^12 different possibilities are available for designing a predetermined gRNA sequence for decryption using a 4 base system. Following removal of extraneous (aka "junk") DNA, the predetermined oligonucleotides encoding for a target sequence are subject to downstream processing, e.g., amplification and sequencing, resulting in a final sequence without the extra (junk) sequence. In some instances, each oligonucleotide of the plurality of oligonucleotides is designed for modification (e.g., cleavage, base swapping, recombination) at multiple locations. For example, each oligonucleotide of the plurality of oligonucleotides is synthesized with complementary regions for binding to about 1, 2, 3, 4, 5, 6, 7, 8, 9, 10 or more gRNA sequences. In such an arrangement, each of the plurality of oligonucleotides is subject to cleavage, base swapping, recombination subsequent to nuclease (e.g., CRISPR/Cas) complex activity at 1, 2, 3, 4, 5, 6, 7, 8, 9, 10 or more locations.

Figure 4A:
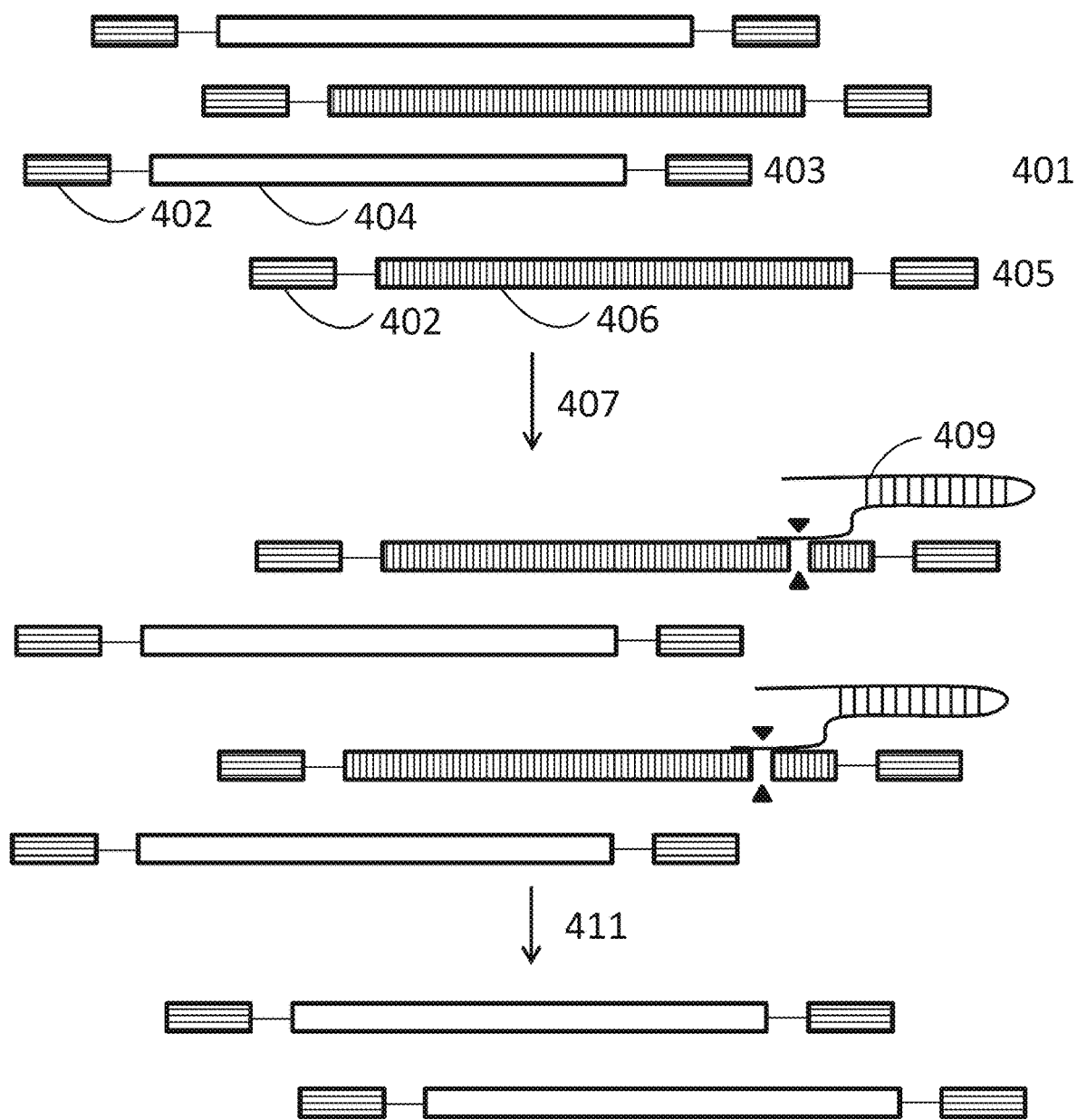
FIGS. 4A-4B depict a bioencryption method using a Cas enzyme.

A first process for target enrichment for data encryption using CRISPR/Cas9 is illustrated in FIG. 4A. A population of DNA sequences 401 comprises DNA information 403 and encrypted DNA 405. The DNA information 403 and encrypted DNA 405 comprise adapter sequences 402 and DNA sequences 404, 406, respectively. Guide RNAs 409 are added 407 to the population of DNA sequences 401. The guide RNAs 409 are used to remove the encrypted DNA 405 by recognizing cleavage sequences encrypted in the encrypted DNA 405. Following addition of the guide RNAs 409, the encrypted DNA 405 is cleaved resulting in a nucleic acid sequence no longer intact. The encrypted DNA 405 are thus removed 411 from the population leaving the DNA information 403, for example, when the encrypted DNA 405 comprising a nucleic acid sequence that is no longer intact is unable to be amplified.

Figure 4B:
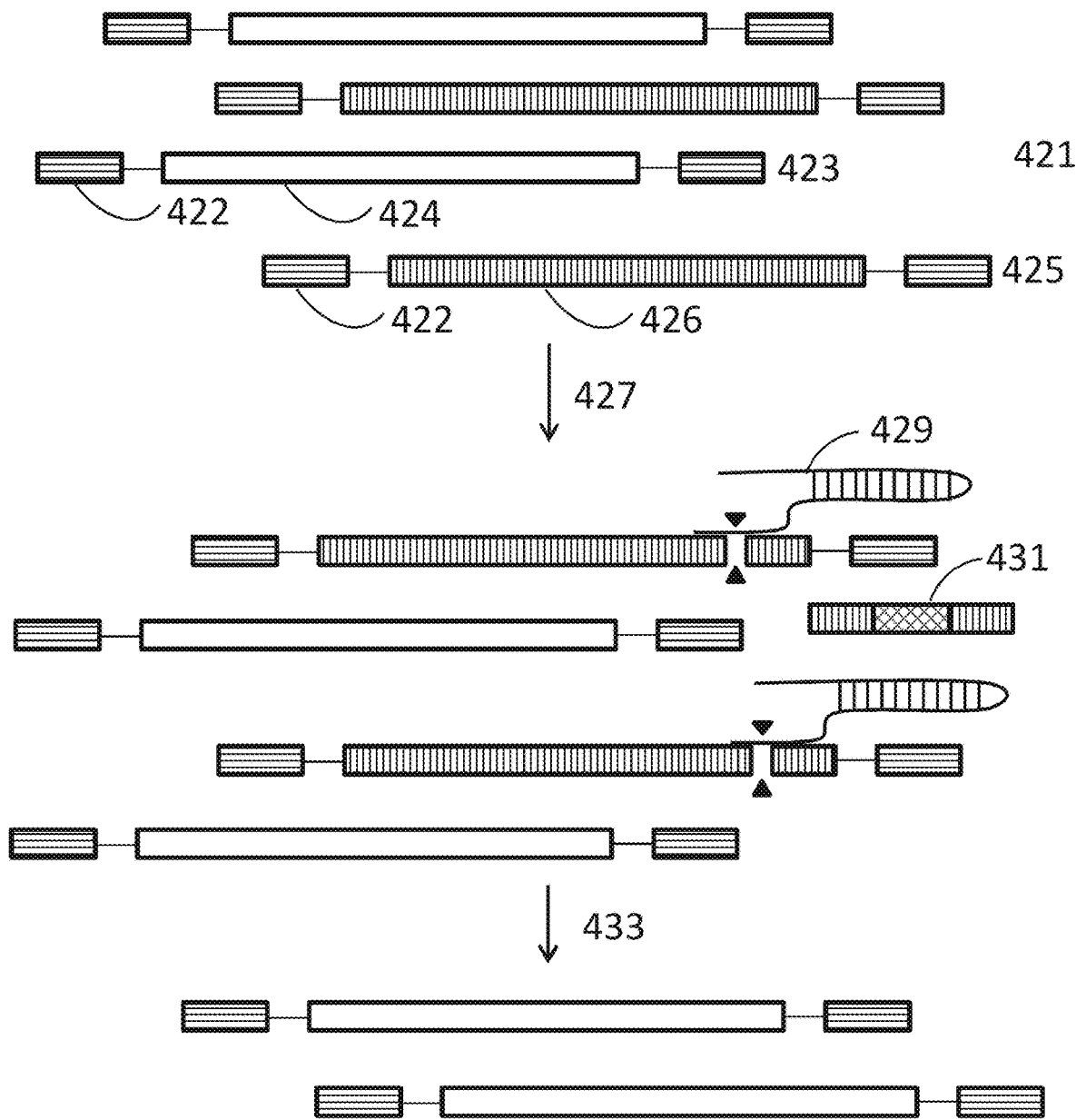

A second process for target enrichment for data encryption using CRISPR/Cas9 is illustrated in FIG. 4B. A population of DNA sequences 421 comprises DNA information 423 and encrypted DNA 425. The DNA information 423 and encrypted DNA 425 comprise adapter sequences 422 and DNA sequences 424, 426, respectively. Guide RNAs 429 and donor DNA 431 are added 427 to the population of DNA sequences 421. The guide RNAs 429 recognize an encrypted cleavage site in the encrypted DNA 425 and generate a cleavage site for insertion of the donor DNA 431. Insertion of the donor DNA 431 results in an insertion or frameshift in the encrypted DNA 425. In some instances, insertion of the donor DNA 431 results in introduction of a sequence tag for hybridization or incorporation of modified nucleotides with enhanced affinity to a capture reagent. For example, the donor DNA 431 is recognized by a fluorescent probe. In some instances, the donor DNA 431 introduces a sequence for electromagnetic radiation based (e.g., photolysis or photodetection) or chemical cleavage based (e.g, gaseous ammonia or methylamine treatment to cleave Thymidine-succinyl hexamide CED phosphoramidite (CLP-2244 from ChemGenes)) bioencryption and/or biodecryption. In some instances, the encrypted DNA 425 is no longer recognized for amplification, and only DNA information 423 is amplified resulting in enrichment of the DNA information 423.

Devices, compositions, systems, and methods comprising application of nuclease complex activity based encryption as described herein may comprise base swapping or sequence swapping. For example, bioencryption and biodecryption using CRISPR/Cas comprises base swapping or sequence swapping. In some instances, bioencryption comprises a CRISPR/dCas9 where a disabled or "dead" Cas9 ("dCas9") no longer has a splicing function but, with the addition of another enzymatic activity, performs a different target molecule modifying function. For example, tethering a cytidine deaminase to dCas9 converts a C-G DNA base pair into T-A base pair. In an alternative dCas9 process, a different enzyme tethered to the dCas9 results in changing the base C into a T, or a G to an A in a target DNA.

Provided herein are devices, compositions, systems, and methods for bioencryption and biodecryption comprising application of a restriction enzyme. In some instances, the restriction enzyme targets an enzyme recognition site. In some instances, the enzyme recognition site is a specific nucleotide sequence. In some instances, the restriction enzyme cleaves the phosphate backbone at or near the enzyme recognition site. In some instances, cleavage of the recognition site results in a non-blunt end or a blunt end. In some instances, the restriction enzyme recognizes a nucleotide (e.g., A, T, G, C, U). In some instances, the restriction enzyme recognizes a modification such as, but not limited to, methylation, hydroxylation, or glycosylation. In some instances, the restriction enzyme results in fragmentation. In some instances, fragmentation produces fragments having 5' overhangs, 3' overhangs, blunt ends, or a combination thereof. In some instances, the fragments are selected, for example, based on size. In some instances, fragmentation by a restriction enzyme is followed by ligation. For example, fragmentation by a restriction enzyme is used to leave a predictable overhang, followed by ligation with one or more adapter oligonucleotides comprising an overhang complementary to the predictable overhang on a nucleic acid fragment. Exemplary restriction enzymes and their recognition sequences are provided in Table 1.

TABLE 1

| Restriction Enzymes Table 1 | |
|---|---|
| Recognition Sequence | Enzyme |
| AA/CGTT | AclI |
| A/AGCTT | HindIII HindIII-HF ® |
| AAT/ATT | SspI SspI-HF ® |
| /AATT | MluCI Tsp509I |
| A/CATGT | PciI |
| A/CCGGT | AgeI AgeI-HF ® |
| ACCTGC(4/8) | BspMI BfuAI |
| A/CCWGGT | SexAI |
| A/CGCGT | MluI MluI-HF ® |
| ACGGC(12/14) | BceAI |
| A/CGT | HpyCH4IV |
| ACN/GT | HpyCH4III |
| (10/15)ACNNNNNGTAYC(12/7) (SEQ ID NO: 5) | BaeI |
| (9/12)ACNNNNNCTCC(10/7) (SEQ ID NO: 6) | BsaXI |
| A/CRYGT | AflIII |
| A/CTAGT | SpeI SpeI-HF ® |
| ACTGG(1/-1) | BsrI |
| ACTGGG(5/4) | BmrI |
| A/GATCT | BglII |
| AGC/GCT | AfeI |
| AG/CT | AluI |
| AGG/CCT | StuI |
| AGT/ACT | ScaI ScaI-HF ® |
| AT/CGAT | ClaI BspDI |
| ATCTATGTCGGGTGCGGAGAAAGAGGTAAT (-15/-19) (SEQ ID NO: 7) | PI-SceI |
| ATGCA/T | NsiI NsiI-HF ® |
| AT/TAAT | AseI |
| ATTT/AAAT | SwaI |
| (11/13)CAANNNNNGTGG(12/10) (SEQ ID NO: 8) | CspCI |
| C/AATTG | MfeI MfeI-HF ® |
| CACGAG(-5/-1) | BssSI BssSαI |
| CACGAG | Nb. BssSI |
| CACGTC(-3/-3) | BmgBI |
| CAC/GTG | PmlI |
| CACNNN/GTG | DraIII DraIII-HF ® |
| CACNN/NNGTG (SEQ ID NO: 9) | AleI |
| CAGCAG(25/27) | EcoP15I |
| CAG/CTG | PvuII PvuII-HF ® |
| CAGNNN/CTG | AlwNI |
| CAGTG(2/0) | BtsIMutI |
| NNCASTGNN/ | TspRI |
| CA/TATG | NdeI |
| CATG/ | NlaIII |
| C/ATG | CviAII |
| /CATG | FatI |
| CAYNN/NNRTG (SEQ ID NO: 10) CC(12/16) | MslI FspEI |
| CCANNNNN/NNNNTGG (SEQ ID NO: 11) | XcmI |

TABLE 1-continued

Restriction Enzymes
Table 1

| Recognition Sequence | Enzyme |
|---|---|
| CCANNNNN/NTGG (SEQ ID NO: 12) | BstXI |
| CCANNNN/NTGG (SEQ ID NO: 13) | PflMI |
| CCATC(4/5) | BccI |
| C/CATGG | NcoI NcoI-HF ® |
| CCCAGC(-5/-1) | BseYI |
| CCCGC(4/6) | FauI |
| CCC/GGG | SmaI |
| C/CCGGG | XmaI TspMI |
| (0/-1)CCD | Nt. CviPII |
| CCDG(10/14) | LpnPI |
| CCGC(-3/-1) | AciI |
| CCGC/GG | SacII |
| CCGCTC(-3/-3) | BsrBI |
| C/CGG | MspI HpaII |
| CC/NGG | ScrFI |
| /CCNGG | BssKI StyD4I |
| C/CNNGG | BsaJI |
| CCNNNNN/NNGG (SEQ ID NO: 14) | BslI |
| C/CRYGG | BtgI |
| CC/SGG | NciI |
| C/CTAGG | AvrII |
| CCTC(7/6) | MulI |
| CCTCAGC(-5/-2) | BbvCI |
| CCTCAGC | Nb. BbvCI |
| CCTCAGC(-5/-7) | Nt. BbvCI |
| CCTGCA/GG | SbfI SbfI-HF ® |
| CCTNAGC(-5/-2) | Bpu10I |
| CC/TNAGG | Bsu36I |
| CCTNN/NNNAGG (SEQ ID NO: 15) | EcoNI |
| CCTTC(6/5) | HpyAV |
| CC/WGG | BstNI |
| /CCWGG | PspGI |
| C/CWWGG | StyI StyI-HF ® |
| (10/12)CGANNNNNNTGC(12/10) (SEQ ID NO: 16) | BcgI |
| CGAT/CG | PvuI PvuI-HF ® |
| CG/CG | BstUI |
| C/GGCCG | EagI EagI-HF ® |
| CG/GWCCG | RsrII |
| CGRY/CG | BsiEI |
| C/GTACG | BsiWI BsiWI-HF ® |
| CGTCTC(1/5) | BsmBI |
| CGWCG/ | Hpy99I |
| CMG/CKG | MspA1I |
| CNNR(9/13) | MspJI |
| CR/CCGYG | SgrAI |
| C/TAG | BfaI |
| CTCAG(9/7) | BspCNI |
| C/TCGAG | XhoI PaeR7I TliI |
| CTCTTC(1/4) | EarI |
| CTGAAG(16/14) | AcuI |
| CTGCA/G | PstI PstI-HF ® |
| CTGGAG(16/14) | BpmI |
| C/TNAG | DdeI |
| C/TRYAG | SfcI |
| C/TTAAG | AflII |
| CTTGAG(16/14) | BpuEI |
| C/TYRAG | SmlI |
| C/YCGRG | AvaI BsoBI |
| GAAGA(8/7) | MboII |
| GAAGAC(2/6) | BbsI BbsI-HF ® |
| GAANN/NNTTC (SEQ ID NO: 17) | XmnI |
| GAATGC(1/-1) | BsmI |
| GAATGC | Nb. BsmI |
| G/AATTC | EcoRI EcoRI-HF ® |
| GACGC(5/10) | HgaI |
| GACGT/C | AatII |
| GAC/GTC | ZraI |
| GACN/NNGTC | Tth111I PflFI |
| GACNN/NNGTC (SEQ ID NO: 18) | PshAI |
| GACNNN/NNGTC (SEQ ID NO: 19) | AhdI |
| GACNNNN/NNGTC (SEQ ID NO: 20) | DrdI |
| GAG/CTC | Eco53kI |
| GAGCT/C | SacI SacI-HF ® |
| GAGGAG(10/8) | BseRI |

TABLE 1-continued

Restriction Enzymes
Table 1

| Recognition Sequence | Enzyme |
|---|---|
| GAGTC(4/5) | PleI |
| GAGTC(4/-5) | Nt.BstNBI |
| GAGTC(5/5) | MlyI |
| G/ANTC | HinfI |
| GAT/ATC | EcoRV EcoRV-HF® |
| /GATC | MboI Sau3AI DpnII BfuCI |
| GA/TC | DpnI |
| GATNN/NNATC (SEQ ID NO: 21) | BsaBI |
| G/AWTC | TfiI |
| GCAATG(2/0) | BsrDI |
| GCAATG | Nb.BsrDI |
| GCAGC(8/12) | BbvI |
| GCAGTG(2/0) | BtsI BtsαI |
| GCAGTG | Nb.BtsI |
| GCANNNN/NTGC (SEQ ID NO: 22) | BstAPI |
| GCATC(5/9) | SfaNI |
| GCATG/C | SphI SphI-HF® |
| GCCC/GGGC | SrfI |
| GCCGAG(21/19) | NmeAIII |
| GCC/GGC | NaeI |
| G/CCGGC | NgoMIV |
| GCCNNNN/NGGC (SEQ ID NO: 23) | BglI |
| GCGAT/CGC | AsiSI |
| GCGATG(10/14) | BtgZI |
| G/CGC | HinP1I |
| GCG/C | HhaI |
| G/CGCGC | BssHII |
| GC/GGCCGC | NotI NotI-HF® |
| GC/NGC | Fnu4HI |
| GCN/NGC | Cac8I |
| GCNNNNN/NNGC (SEQ ID NO: 24) | MwoI |
| G/CTAGC | NheI NheI-HF® |
| GCTAG/C | BmtI BmtI-HF® |
| GCTCTTC(1/4) | SapI BspQI |
| GCTCTTC(1/-7) | Nt.BspQI |
| GC/TNAGC | BlpI |
| G/CWGC | TseI ApeKI |
| GDGCH/C | Bsp1286I |
| GGATC(4/5) | AlwI |
| GGATC(4/-5) | Nt.AlwI |
| G/GATCC | BamHI BamHI-HF® |
| GGATG(9/13) | FokI |
| GGATG(2/0) | BtsCI |
| GG/CC | HaeIII PhoI |
| GGCCGG/CC | FseI |
| GGCCNNNN/NGGCC (SEQ ID NO: 25) | SfiI |
| GG/CGCC | NarI |
| G/GCGCC | KasI |
| GGC/GCC | SfoI |
| GGCGC/C | PluTI |
| GG/CGCGCC | AscI |
| GGCGGA(11/9) | EciI |
| GGGAC(10/14) | BsmFI |
| GGGCC/C | ApaI |
| G/GGCCC | PspOMI |
| G/GNCC | Sau96I |
| GGN/NCC | NlaIV |
| GGTAC/C | KpnI KpnI-HF® |
| G/GTACC | Acc65I |
| GGTCTC(1/5) | BsaI BsaI-HF® |
| GGTGA(8/7) | HphI |
| G/GTNACC | BstEII BstEII-HF® |
| G/GWCC | AvaII |
| G/GYRCC | BanI |
| GKGCM/C | BaeGI |
| GR/CGYC | BsaHI |
| GRGCY/C | BanII |
| GT/AC | RsaI |
| G/TAC | CviQI |
| GTA/TAC | BstZ17I |
| GTATAC | BstZ17I-HF® |
| GTATCC(6/5) | BciVI |
| G/TCGAC | SalI SalI-HF® |
| GTCTC(1/-5) | Nt.BsmAI |
| GTCTC(1/5) | BsmAI BcoDI |

TABLE 1-continued

Restriction Enzymes

| Recognition Sequence | Enzyme |
|---|---|
| G/TGCAC | ApaLI |
| GTGCAG(16/14) | BsgI |
| GT/MKAC | AccI |
| GTN/NAC | Hpy166II |
| /GTSAC | Tsp45I |
| GTT/AAC | HpaI |
| GTTT/AAAC | PmeI |
| GTY/RAC | HincII |
| GWGCW/C | BsiHKAI |
| R/AATTY | ApoI ApoI-HF |
| RCATG/Y | NspI |
| R/CCGGY | BsrFI BsrFαI |
| R/GATCY | BstYI |
| RGCGC/Y | HaeII |
| RG/CY | CviKI-1 |
| RG/GNCCY | EcoO109I |
| RG/GWCCY | PpuMI |
| TAACTATAACGGTCCTAAGGTAGCGAA (-9/-13) (SEQ ID NO: 26) | I-CeuI |
| TAC/GTA | SnaBI |
| TAGGGATAACAGGGTAAT(-9/-13) (SEQ ID NO: 27) | I-SceI |
| T/CATGA | BspHI |
| T/CCGGA | BspEI |
| TCCRAC(20/18) | MmeI |
| T/CGA | TaqαI |
| TCG/CGA | NruI NruI-HF ® |
| TCN/GA | Hpy188I |
| TC/NNGA | Hpy188III |
| T/CTAGA | XbaI |
| T/GATCA | BclI |
| TG/CA | HpyCH4V |
| TGC/GCA | FspI |
| TGGCAAACAGCTATTATGGGTATTATGGGT (-13/-17) (SEQ ID NO: 28) | PI-PspI |
| TGG/CCA | MscI |
| T/GTACA | BsrGI BsrGI-HF ® |
| T/TAA | MseI |
| TTAAT/TAA | PacI |
| TTA/TAA | PsiI |
| TT/CGAA | BstBI |
| TTT/AAA | DraI |
| VC/TCGAGB | PspXI |
| W/CCGGW | BsaWI |
| YAC/GTR | BsaAI |
| Y/GGCCR | EaeI |

Provided herein are devices, compositions, systems, and methods for bioencryption and biodecryption may comprise application of a repair enzyme. DNA repair enzymes, in some instances, are derived from a particular organism or virus or are non-naturally occurring variants thereof. Exemplary DNA repair enzymes include, but are not limited to, *E. coli* endonuclease IV, Tth endonuclease IV, human AP endonuclease, glycosylases, such as UDG, *E. coli* 3-methyladenine DNA glycoylase (AlkA) and human Aag, glycosylase/lyases, such as *E. coli* endonuclease III, *E. coli* endonuclease VIII, *E. coli* Fpg, human OGG1, and T4 PDG, and lyases. Exemplary additional DNA repair enzymes are listed in Table 2.

TABLE 2

DNA Repair Enzymes.

| Gene Name | Activity | Accession Number |
|---|---|---|
| UNG | Uracil-DNA glycosylase | NM_080911 |
| SMUG1 | Uracil-DNA glycosylase | NM_014311 |
| MBD4 | Removes U or T opposite G at CpG sequences | NM_003925 |
| TDG | Removes U, T or ethenoC opposite G | NM_003211 |
| OGG1 | Removes 8-oxoG opposite C | NM_016821 |
| MUTYH (MYH) | Removes A opposite 8-oxoG | NM_012222 |
| NTHL1 (NTH1) | Removes Ring-saturated or fragmented pyrimidines | NM_002528 |
| MPG | Removes 3-meA, ethenoA, hypoxanthine | NM_002434 |
| NEIL1 | Removes thymine glycol | NM_024608 |
| NEIL2 | Removes oxidative products of pyrimidines | NM_145043 |
| XPC | Binds damaged DNA as complex with RAD23B, CETN2 | NM_004628 |
| RAD23B (HR23B) | Binds damaged DNA as complex with XPC, CETN2 | NM_002874 |
| CETN2 | Binds damaged DNA as complex with XPC, RAD23B | NM_004344 |
| RAD23A (HR23A) | Substitutes for HR23B | NM_005053 |
| XPA | Binds damaged DNA in preincision complex | NM_000380 |
| RPA1 | Binds DNA in preincision complex | NM_002945 |
| RPA2 | Binds DNA in preincision complex | NM_002946 |
| RPA3 | Binds DNA in preincision complex | NM_002947 |
| ERCC5 (XPG) | 3' incision | NM_000123 |
| ERCC1 | 5' incision subunit | NM_001983 |
| ERCC4 (XPF) | 5' incision subunit | NM_005236 |
| LIG1 | DNA joining | NM_000234 |
| CKN1(CSA) | Cockayne syndrome; Needed for transcription-coupled NER | NM_000082 |
| ERCC6 (CSB) | Cockayne syndrome; Needed for transcription-coupled NER | NM_000124 |

TABLE 2-continued

DNA Repair Enzymes.

| Gene Name | Activity | Accession Number |
|---|---|---|
| XAB2 (HCNP) | Cockayne syndrome; Needed for transcription-coupled NER | NM_020196 |
| DDB1 | Complex defective in XP group E | NM_001923 |
| DDB2 | DDB1, DDB2 | NM_000107 |
| MMS19L (MMS19) | Transcription and NER | NM_022362 |
| FEN1 (DNase IV) | Flap endonuclease | NM_004111 |
| SPO11 | endonuclease | NM_012444 |
| FLJ35220 (ENDOV) | incision 3' of hypoxanthine and uracil | NM_173627 |
| FANCA | Involved in tolerance or repair of DNA crosslinks | NM_000135 |
| FANCB | Involved in tolerance or repair of DNA crosslinks | NM_152633 |
| FANCC | Involved in tolerance or repair of DNA crosslinks | NM_000136 |
| FANCD2 | Involved in tolerance or repair of DNA crosslinks | NM_033084 |
| FANCE | Involved in tolerance or repair of DNA crosslinks | NM_021922 |
| FANCF | Involved in tolerance or repair of DNA crosslinks | NM_022725 |
| FANCG (XRCC9) | Involved in tolerance or repair of DNA crosslinks | NM_004629 |
| FANCL | Involved in tolerance or repair of DNA crosslinks | NM_018062 |
| DCLRE1A (SNM1) | DNA crosslink repair | NM_014881 |
| DCLRE1B (SNM1B) | Related to SNM1 | NM_022836 |
| NEIL3 | Resembles NEIL1 and NEIL2 | NM_018248 |
| ATRIP (TREX1) | ATR-interacting protein 5' alternative ORF of the TREX1/ATRIP gene | NM_130384 |
| NTH | Removes damaged pyrimidines | NP_416150.1 |
| NEI | Removes damaged pyrimidines | NP_415242.1 |
| NFI | Deoxyinosine 3' endonuclease | NP_418426.1 |
| MUTM | Formamidopyrimidine DNA glycosylase | NP_418092.1 |
| UNG | Uracil-DNA glycosylase | NP_417075.1 |
| UVRA | DNA excision repair enzyme complex | NP_418482.1 |
| UVRB | DNA excision repair enzyme complex | NP_415300.1 |
| UVRC | DNA excision repair enzyme complex | NP_416423.3 |
| DENV | Pyrimidine dimer glycosylase | NP_049733.1 |

Provided herein are devices, compositions, systems, and methods for bioencryption and/or biodecryption comprising nucleic acid modification. In some instances, the nucleic acid modification impacts activity of nucleic acid sequences in a sequencing reaction. For example, the nucleic acid modification prevents the encrypted nucleic acid sequences from being amplified. In some instances, the nucleic acid modification comprises, but is not limited to, methylated bases, PNA (peptide nucleic acid) nucleotides, LNA (locked nucleic acid) nucleotides, and 2'-O-methyl-modified nucleotides. In some instances, the nucleic acid modification comprises a modified nucleobase that is not a cytosine, guanine, adenine or thymine. Non-limiting modified nucleobases include, without limitation, uracil, 3-meA (3-methyladenine), hypoxanthine, 8-oxoG (7,8-dihydro-8-oxoguanine), FapyG, FapyA, Tg (thymine glycol), hoU (hydroxyuracil), hmU (hydroxymethyluracil), fU (formyluracil), hoC (hydroxycytosine), fC (formylcytosine), 5-meC (5-methylcytosine), 6-meG (O6-methylguanine), 7-meG (N7-methylguanine), εC (ethenocytosine), 5-caC (5-carboxylcytosine), 2-hA, εA (ethenoadenine), 5-fU (5-fluorouracil), 3-meG (3-methylguanine), and isodialuric acid.

Provided herein are devices, compositions, systems, and methods for bioencryption comprising use of nucleic acid probe sequences. In some instances, nucleic acid probe sequences that are complementary to a portion of the nucleic acid sequences are then removed by a nuclease. For example, the nuclease is a duplex specific nuclease that recognizes a double stranded nucleic acid molecule formed between the nucleic acid probes and the nucleic acid sequences. In some instances, the nucleic acid probe allows for capturing and isolating nucleic acid sequences. In some instances, the nucleic acid probes comprise at least about 5, 10, 15, 20, 25, 30, 35, 40, 45, 50, 55, 60, 65, 70, 75, 80, 85, 90, 95, 100, or more than 100 nucleotides in length.

In some instances, nucleic acid sequences are identified using nucleic acid probes comprising a label such as, but not limited to, an affinity tag such as biotin, digoxigenin, Ni-Nitrilotriacetic acid, desthiobiotin, histidine, polyhistidine, myc, hemagglutinin (HA), FLAG, a fluorescence tag, a tandem affinity purification (TAP) tag, glutathione S transferase (GST), a polynucleotide, an aptamer, a polypeptide (e.g., an antigen or antibody), or derivatives thereof. In some instances, the label is detected by light absorption, fluorescence, chemiluminescence, electrochemiluminescence, mass, or charge. Non-limiting examples of fluorophores are Alexa-Fluor dyes (e.g., Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, and Alexa Fluor® 750), APC, Cascade Blue, Cascade Yellow and R-phycoerythrin (PE), DyLight 405, DyLight 488, DyLight 550, DyLight 650, DyLight 680, DyLight 755, DyLight 800, FITC, Pacific Blue, PerCP, Rhodamine, Texas Red, Cy5, Cy5.5, and Cy7.

Provided herein are devices, compositions, systems, and methods for bioencryption and/or biodecryption comprising nucleic acid hybridization based binding. Nucleic acid probes comprising an affinity tag may be used. In some instances, the affinity tag allows for the nucleic acid sequences to be pulled down. For example, the affinity tag biotin is conjugated to nucleic acid probes that are complementary to the nucleic acid sequences and is pulled down using streptavidin. In some instances, the affinity tag comprises magnetically susceptible material, e.g., a magnet or magnetically susceptible metal. In some instances, the nucleic acid sequences are pulled down using a solid support such as streptavidin and immobilized on the solid support. In some instances, the nucleic acid sequences are pulled down in solution such as through beads. In some instances, the nucleic acid probes allow for exclusion based on size. For example, the nucleic acid probes result in the nucleic acid sequences having a size different from other nucleic acid sequences so that the nucleic acid sequences are removed by size-based depletion.

Devices, compositions, systems, and methods for bioencryption and/or biodecryption comprising nucleic acid hybridization based binding may comprise controlled amplification. In some instances, the nucleic acid hybridization based binding strategy is directed to controlled amplification, where a plurality of oligonucleotides synthesized have a similar region for a forward primer to bind, but the reverse primer region is not readily identifiable. In such an instance, a predetermined reverse primer would be required. In a first exemplary workflow, a pool of reverse primers with preselected regions to bind to each of the different synthesized oligonucleotides is generated and used in an extension amplification reaction (e.g., with a DNA polymerase) to amplify the oligonucleotides for downstream processing, e.g., further amplification or a DNA sequencing reaction. Optionally, each of the reverse primers comprises an adapter region comprising a common sequence to incorporate a universal reverse primer binding site by an extension amplification reaction (e.g., with a DNA polymerase). In such an arrangement, the downstream processing is simplified as only a single forward or reverse primer is required to amplify or sequence the plurality of oligonucleotides. In a second exemplary workflow, a plurality of oligonucleotides are synthesized, each having one or two regions comprising a hybridization motif that, while varied, has sufficient hybridization ability to a common primer to allow downstream processing of the plurality of oligonucleotides (e.g., amplification or sequencing reactions) utilizing a common primer for one of or both of 5' and 3' regions of each of the synthesized oligonucleotides. In some instances, the oligonucleotide population is designed to be hybridized to about 1, 2, 3, 4, 5, 6, 7, 8, 9, 10, 11, 12, 13, 14, 15, 16, 17, 18, 19, 20 or more nucleobases of the common primer.

Provided herein are devices, compositions, systems, and methods for bioencryption and/or biodecryption comprising use of electromagnetic radiation (EMR). In some instances, the electromagnetic radiation provides for cleavage or image capture-based detection of a nucleic acid sequence. In some instances, EMR is applied towards a surface at a wavelength from about 100 nm to about 400 nm, from about 100 nm to about 300 nm, or from about 100 nm to about 200 nm. In some instances, EMR is applied towards a surface at a wavelength from less than 0.01 nm. In some instances, EMR is applied towards a surface at a wavelength from about 10 nm to about 400 nm, about 400 nm to about 700 nm, or about 700 nm to about 100,000 nm. For example, EMR is applied at an ultraviolet (UV) wavelength, or a deep UV wavelength. In some instances, deep UV light is applied to a surface at a wavelength of about 172 nm to cleave a bound agent from the surface. In some instances, EMR is applied with a xenon lamp. Exposure distance is a measurement between the lamp and the surface. In some instances, the exposure distance is about 0.1 to 5 cm. In some instances, the exposure distance is about 0.5 to 2 cm. In some instances, the exposure distance is about 0.5, 1, 2, 3, 4, or 5 cm. In some instances, EMR is applied with a laser. Exemplary lasers and their wavelengths include but are not limited to $Ar_2$ (126 nm), $Kr_2$ (146 nm), $F_2$ (157 nm), $Xe_2$ (172 and 175 nm), ArF (193 nm). In some instances, the nucleic acid sequences comprise nucleobases that are photocleavable at a specific site. In some instances, the nucleic acid sequences comprise a modified nucleobase that is photocleavable. In some instances, the nucleic acid sequences are photocleavable by application of a specific wavelength of light. In some instances, the nucleic acid sequences are photocleavable by application of multiple wavelengths of light.

Provided herein are devices, compositions, systems, and methods for bioencryption and/or biodecryption comprising use of chemical lysis. In some instances, the nucleic acid sequences comprise nucleobases that are chemically cleavable at a specific site. In some instances, the nucleic acid sequences comprise a modified nucleobase that is chemically cleavable. In some instances, the modified nucleobase comprises a modification that is chemically cleavable. In some instances, chemical lysis is performed using an amine reagent. In some instances, the amine reagent is a liquid, a gas, an aqueous reagent, or an anhydrous reagent. Non-limiting examples of amine reagents are ammonium hydroxide, ammonia gas, a $C_1$-$C_6$ alkylamine, or methylamine.

Devices, compositions, systems, and methods for bioencryption as described herein may comprise conversion of the digital sequence to a nucleic acid sequence. In some instances, the nucleic acid sequence is a DNA sequence. In some instances, the DNA sequence is single stranded or double stranded. In some instances, the nucleic acid sequence is a RNA sequence. In some instances, the RNA sequence is single stranded or double stranded. In some instances, the nucleic acid sequence is encrypted in a larger population of nucleic acid sequences. In some instances, the larger population of nucleic acid sequences is a homogenous population or a heterogeneous population. In some instances, the population of nucleic acid sequences comprises DNA sequences. In some instances, the DNA sequences are single stranded or double stranded. In some instances, the population of nucleic acid sequences comprises RNA sequences. In some instances, the RNA sequences are single stranded or double stranded.

A number of nucleic acid sequences may be encrypted. In some instances, the number of nucleic acid sequences that are encrypted are about 10 sequences to about 1 million or more sequences. In some instances, a number of nucleic acid sequences that are encrypted are at least about 10, 50, 100, 200, 500, 1,000, 2,000, 4,000, 8,000, 10,000, 25,000, 30,000, 35,000, 40,000, 45,000, 50,000, 55,000, 60,000, 65,000, 70,000, 80,000, 90,000, 100,000, 200,000, 300,000, 400,000, 500,000, 600,000, 700,000, 800,000, 900,000, 1 million, or more than 1 million sequences. In some instances, a number of nucleic acid sequences that are encrypted is greater than 1 trillion.

In some instances, the nucleic acid sequences that are encrypted comprise at least 10, 25, 50, 75, 100, 125, 150, 175, 200, 225, 250, 300, or more than 300 bases in length. In some instances, the nucleic acid sequences that are encrypted comprises 10 bases to 25 bases, 10 bases to 50 bases, 10 bases to 75 bases, 10 bases to 100 bases, 10 bases to 125 bases, 10 bases to 150 bases, 10 bases to 175 bases, 10 bases to 200 bases, 10 bases to 225 bases, 10 bases to 250 bases, 10 bases to 300 bases, 25 bases to 50 bases, 25 bases to 75 bases, 25 bases to 100 bases, 25 bases to 125 bases, 25 bases to 150 bases, 25 bases to 175 bases, 25 bases to 200 bases, 25 bases to 225 bases, 25 bases to 250 bases, 25 bases to 300 bases, 50 bases to 75 bases, 50 bases to 100 bases, 50 bases to 125 bases, 50 bases to 150 bases, 50 bases to 175 bases, 50 bases to 200 bases, 50 bases to 225 bases, 50 bases to 250 bases, 50 bases to 300 bases, 75 bases to 100 bases, 75 bases to 125 bases, 75 bases to 150 bases, 75 bases to 175 bases, 75 bases to 200 bases, 75 bases to 225 bases, 75 bases to 250 bases, 75 bases to 300 bases, 100 bases to 125 bases, 100 bases to 150 bases, 100 bases to 175 bases, 100 bases to 200 bases, 100 bases to 225 bases, 100 bases to 250 bases, 100 bases to 300 bases, 125 bases to 150 bases, 125 bases to 175 bases, 125 bases to 200 bases, 125 bases to 225 bases, 125 bases to 250 bases, 125 bases to 300 bases, 150 bases to 175 bases, 150 bases to 200 bases, 150 bases to 225 bases, 150 bases to 250 bases, 150 bases to 300 bases, 175 bases to 200 bases, 175 bases to 225 bases, 175 bases to 250 bases, 175 bases to 300 bases, 200 bases to 225 bases, 200 bases to 250 bases, 200 bases to 300 bases, 225 bases to 250 bases, 225 bases to 300 bases, or 250 bases to 300 bases.

In some instances, nucleic acid sequences that are encrypted result in at least 10%, 20%, 30%, 40%, 50%, 60%, 70%, 80%, 90%, 95%, or more than 95% enrichment of a nucleic acid sequence of interest. In some instances, nucleic acid sequences that are encrypted result in about 10%, 20%, 30%, 40%, 50%, 60%, 70%, 80%, 90%, 95%, or more than 95% enrichment of a nucleic acid sequence of interest.

Devices, compositions, systems, and methods for bioencryption and/or biodecryption as described herein may comprise a DNA or RNA based system. Canonical DNA is a base 4 coding system, having four different nucleobases available: A, T, C or G (adenine, thymine, cytosine, and guanine). Thus, these 4 bases allow for a base 3 (using less than all), or a 4 base coding scheme. In addition, use of uracil (U), which is found in RNA, provides a fifth base and allows for a base 5 coding scheme. In addition, a modified nucleobase may be used for a nucleic acid base coding greater than 4. Nucleobases that are not canonical DNA nucleobases or modified nucleobases include, without limitation, uracil, 3-meA (3-methyladenine), hypoxanthine, 8-oxoG (7,8-dihydro-8-oxoguanine), FapyG, FapyA, Tg (thymine glycol), hoU (hydroxyuracil), hmU (hydroxymethyluracil), fU (formyluracil), hoC (hydroxycytosine), fC (formylcytosine), 5-meC (5-methylcytosine), 6-meG (06-methylguanine), 7-meG (N7-methylguanine), εC (ethenocytosine), 5-caC (5-carboxylcytosine), 2-hA, εA (ethenoadenine), 5-fU (5-fluorouracil), 3-meG (3-methylguanine), hmC (hydroxymethylcytosine) and isodialuric acid. Further provided herein are coding schemes where machine instructions provide for conversion of digital information in the form of a binary sequence into an intermediate code prior to ultimately being converted to the final nucleic acid sequence.

In some instances, to store data in a sequence of DNA, the information is converted from the 1s and 0s of binary code into the code of A, T, G, and C bases of DNA. In some instances, items of information are first encoded in a digital information form. In some cases, the binary code of digital information is converted into a biomolecule-based (e.g., DNA-based) code while preserving the information that the code represents. This converted code (digital binary code to a biomolecule code) is referred to herein as resulting in a "predetermined" sequence with respect to the deposit of a biomolecule disclosed herein on a surface disclosed herein. The predetermined sequence may encode sequence for a plurality of oligonucleotides.

Binary Code Conversion

Generally, the initial code is digital information, typically in the form of binary code employed by a computer. General purpose computers are electronic devices reading "on" or "off" states, represented by the numbers "0" and "1". This binary code is application for computers to read multiple types of items of information. In binary arithmetic, the number two is written as the number 10. For example, "10" indicates "one time the number, two and no more". The number "3," is written as "11" to mean "one times two and one more." The number "4" is written as "100," the number "5" as "101," "six" as "110," etc. An example of American Standard Code II (ASCII) for binary code is provided for the alphabet in lower and upper case in Table 3.

TABLE 3

American Standard Code II (ASCII) for Binary Code

| Letter | ASCII Code | Binary | Letter | ASCII Code | Binary | No. | ASCII Code | Binary |
|---|---|---|---|---|---|---|---|---|
| a | 97 | 1100001 | A | 65 | 1000001 | 0 | chr (0) | 00000000 |
| b | 98 | 1100010 | B | 66 | 1000010 | 1 | chr (1) | 00000001 |
| c | 99 | 1100011 | C | 67 | 1000011 | 2 | chr (2) | 00000010 |
| d | 100 | 1100100 | D | 68 | 1000100 | 3 | chr (3) | 00000011 |
| e | 101 | 1100101 | E | 69 | 1000101 | 4 | chr (4) | 00000100 |
| f | 102 | 1100110 | F | 70 | 1000110 | 5 | chr (5) | 00000101 |
| g | 103 | 1100111 | G | 71 | 1000111 | 6 | chr (6) | 00000110 |
| h | 104 | 1101000 | H | 72 | 1001000 | 7 | chr (7) | 00000111 |
| i | 105 | 1101001 | I | 73 | 1001001 | 8 | chr (8) | 00001000 |
| j | 106 | 1101010 | J | 74 | 1001010 | 9 | chr (9) | 00001001 |
| k | 107 | 1101011 | K | 75 | 1001011 | 10 | chr (10) | 00001010 |
| l | 108 | 1101100 | L | 76 | 1001100 | 11 | chr (11) | 00001011 |
| m | 109 | 1101101 | M | 77 | 1001101 | 12 | chr (12) | 00001100 |
| n | 110 | 1101110 | N | 78 | 1001110 | 13 | chr (13) | 00001101 |
| o | 111 | 1101111 | O | 79 | 1001111 | 14 | chr (14) | 00001110 |
| p | 112 | 1110000 | P | 80 | 1010000 | 15 | chr (15) | 00001111 |
| q | 113 | 1110001 | Q | 81 | 1010001 | 16 | chr (16) | 00010000 |
| r | 114 | 1110010 | R | 82 | 1010010 | 17 | chr (17) | 00010001 |
| s | 115 | 1110011 | S | 83 | 1010011 | 18 | chr (18) | 00010010 |
| t | 116 | 1110100 | T | 84 | 1010100 | 19 | chr (19) | 00010011 |
| u | 117 | 1110101 | U | 85 | 1010101 | 20 | chr (20) | 00010100 |
| v | 118 | 1110110 | V | 86 | 1010110 | 21 | chr (21) | 00010101 |
| w | 119 | 1110111 | W | 87 | 1010111 | 22 | chr (22) | 00010110 |
| x | 120 | 1111000 | X | 88 | 1011000 | 23 | chr (23) | 00010111 |
| y | 121 | 1111001 | Y | 89 | 1011001 | 24 | chr (24) | 00011000 |
| z | 122 | 1111010 | Z | 90 | 1011010 | 25 | chr (25) | 00011001 |
| | | | | | | 26 | chr (26) | 00011010 |
| | | | | | | 27 | chr (27) | 00011011 |
| | | | | | | 28 | chr (28) | 00011100 |
| | | | | | | 29 | chr (29) | 00011101 |
| | | | | | | 30 | chr (30) | 00011110 |

Provided herein are methods for converting information in the form of a first code, e.g., a binary sequence to a nucleic acid sequence. The process may involve direct conversion from a base 2 code (i.e., binary) to a base code that is higher. Exemplary base codes include 2, 3, 4, 5, 6, 7, 8, 9, 10 or more. Table 4 illustrates an exemplary alignment between various base numbering schemes. A computer receiving machine instructions for conversion, can automatically convert sequence information from one code to another.

TABLE 4

Alignment of Base Numbering Schemes

| Decimal | 0 | 1 | 2 | 3 | 4 | 5 | 6 | 7 | 8 | 9 |
|---|---|---|---|---|---|---|---|---|---|---|
| Quaternary | 0 | 1 | 2 | 3 | 10 | 11 | 12 | 13 | 20 | 21 |

TABLE 4-continued

Alignment of Base Numbering Schemes

| Octal | 0 | 1 | 2 | 3 | 4 | 5 | 6 | 7 | 10 | 11 |
|---|---|---|---|---|---|---|---|---|---|---|
| Ternary | 0 | 1 | 2 | 10 | 11 | 12 | 20 | 21 | 22 | 100 |
| Binary | 0 | 1 | 10 | 11 | 100 | 101 | 110 | 111 | 1000 | 1001 |

Nucleic Acid Sequence

Figure 5A:
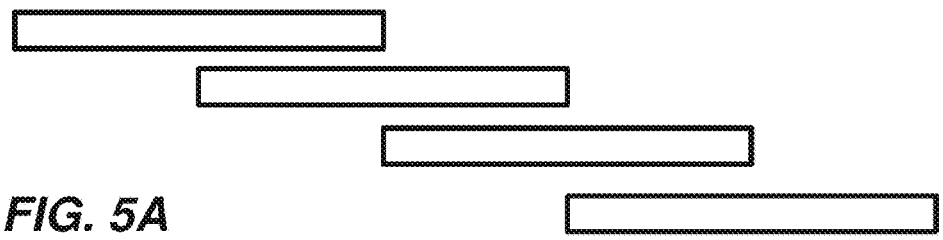
FIGS. 5A-5C depict various oligonucleotide sequence design schemes.
Figure 5B:
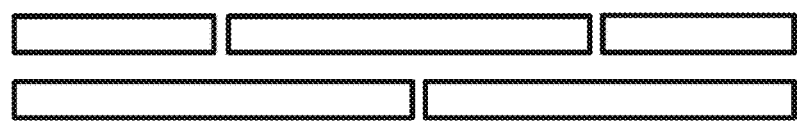
Figure 5C:
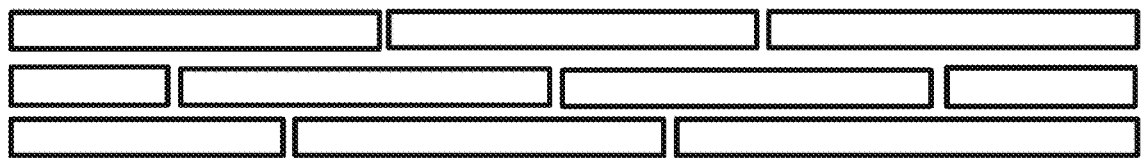

Provided herein are methods for designing a sequence for an oligonucleotide described herein such that the nucleic acid sequence encodes for at least part of an item of information. In some instances, each oligonucleotide sequence has design features to facilitate with sequence alignment during subsequent assembly steps and also to provide a means for error correction. In some arrangements, oligonucleotide sequences are designed such that overlap exits between each oligonucleotide sequence with another in the population. In some instances, each oligonucleotide sequence overlaps with a portion of just one other oligonucleotide sequence, FIG. 5A. In an alternative arrangement, each oligonucleotide sequence region overlaps with two sequences such that 2 copies are generated for each sequence within a single oligonucleotide, FIG. 5B. In yet another arrangement, each oligonucleotide sequence region overlaps with more than two sequences such that 3 copies are generated for each sequence within a single oligonucleotide, FIG. 5C. Sequences for oligonucleotides described herein may encode for 10-2000, 10-500, 30-300, 50-250, or 75-200 bases in length. In some instances, each of the oligonucleotide sequence is at least 10, 15, 20, 25, 30, 50, 100, 150, 200, 500 or more bases in length.

Figure 6A:
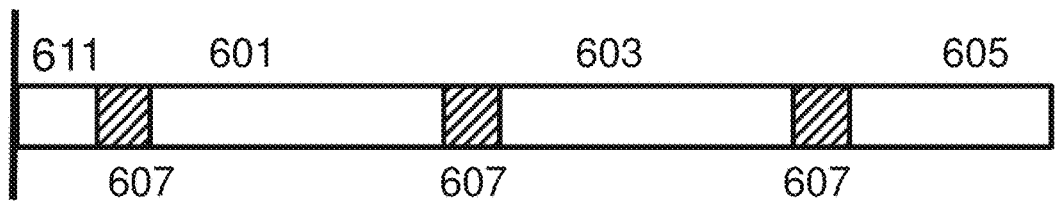
FIGS. 6A-6C depict various oligonucleotide sequence design schemes.
Figure 6B:
Figure 6C:
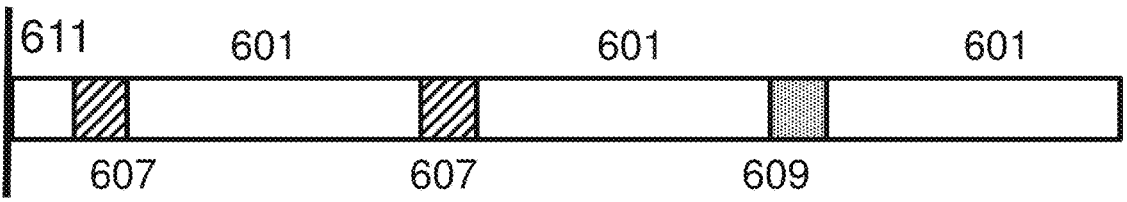

Provided herein are methods, systems and compositions wherein each oligonucleotide sequence described herein is designed to comprise a plurality of coding regions and a plurality of non-coding regions, FIG. 6A. In such an arrangement, each coding region (e.g., 601, 603, 605) encodes for at least a portion of an item of information. Optionally, each coding region in the same oligonucleotide encodes for a sequence from the same item of information, and an overlapping scheme is optionally employed as described herein, FIG. 6B. In further instances, each coding region in the same oligonucleotide encodes for the same sequence, FIG. 6C. Sequences for oligonucleotides described herein may encode for at least 1, 2, 3, 4, 5, 6, 7, 8, 9, 10, 11, 12, 13, 14, 15, 16, 17, 18, 19, 20 or more coding regions. Sequences for oligonucleotides described herein may encode for at least 1, 2, 3, 4, 5, 6, 7, 8, 9, 10, 11, 12, 13, 14, 15, 16, 17, 18, 19, 20 or more of the same coding region. In some instances, each of the multiple coding regions is 10-1000, 20-500, 30-300, 50-250, or 75-200 bases in length. In some instances, each of the multiple coding regions is at least 10, 15, 20, 25, 30, 50, 100, 150, 200 or more bases in length. In some instances, each oligonucleotide comprises a tether region 611 linking the molecule to the surface 602 of a structure.

In arrangements where multiple coding sequences are present in the same oligonucleotide, a cleavage region 607 is optionally present in between each coding region. The cleavage region 607 may be present at the junction between each coding region, or may be present within an adaptor region having a string of sequence between each coding region. A cleavage region 607 may encode for a sequence feature, once synthesized, which will break from the strand subsequent to application of a cleavage signal. The cleavage region 607 may encode for a restriction enzyme recognition site, a modified nucleic acid that is light sensitive and will break under application of electromagnetic radiation (e.g., oligodeoxynucleotide heteropolymers carrying base-sensitive S-pivaloylthioethyl (t-Bu-SATE) phosphotriester linkages sensitive to light wavelengths of >300 nm), or a modified nucleic acid that is sensitive to application of a certain chemical, e.g., Thymidine-succinyl hexamide CED phosphoramidite (CLP-2244 from ChemGenes) which breaks subsequent to application of ammonia gas. Because the design of a sequence to have a particular cleavage scheme may not be readily apparent from sequencing synthesized oligonucleotides, the cleavage scheme provides a means for adding a level of security to sequences encoded by the synthesized nucleic acid library. Sequences for oligonucleotides described herein may encode for at least 1, 2, 3, 4, 5, 6, 7, 8, 9, 10, 11, 12, 13, 14, 15, 16, 17, 18, 19, 20 or more cleavage regions. In some instances, each of the cleavage region encodes for 1-100, 1-50, 1-20, 1-10, 5-25, or 5-30 bases in length. In some instances, each of the cleavage region encodes for at least 1, 2, 3, 4, 5, 6, 7, 8, 9, 10, 11, 12, 13, 14, 15, 16, 17, 18, 19, 20, 25, 30, 40, 50 100 or more bases. In some arrangements, for each oligonucleotide, each coding region is identical and each cleavage region between each coding region is different. For example, a first cleavage region 607 is different from a second cleavage region 609. In some arrangements, the cleavage region 607 closest to the surface 602 is identical to the next distal cleavage region 607.

Figure 7A:
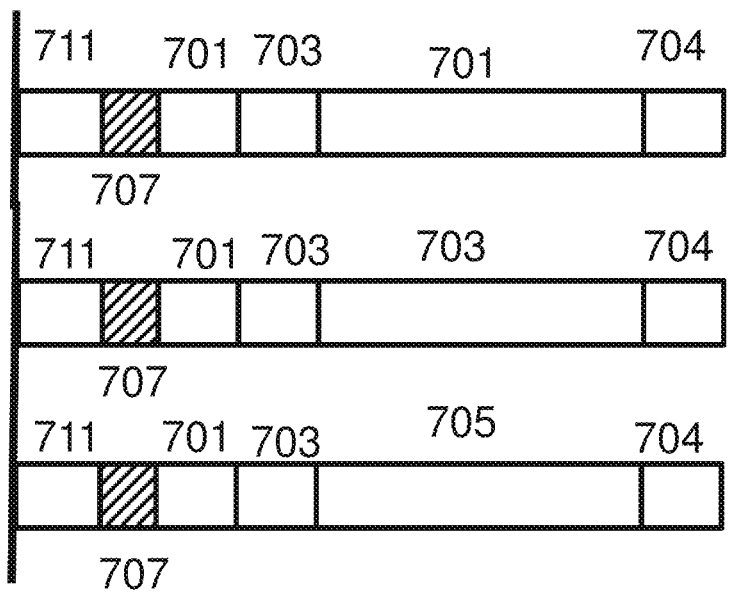
FIGS. 7A-7B depict a barcode design scheme.
Figure 7B:
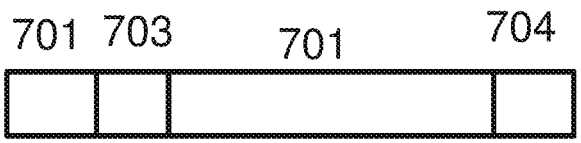
Figure 7B:
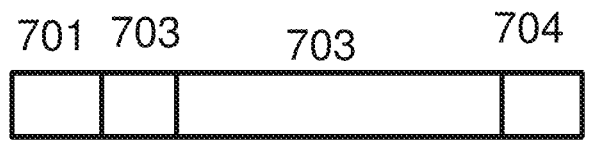
Figure 7B:
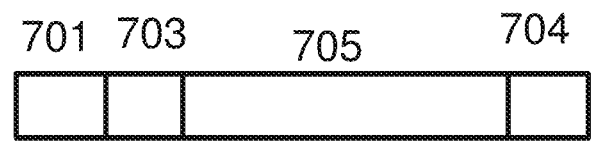

Barcodes are typically known nucleic acid sequences that allow some feature of a polynucleotide with which the barcode is associated to be identified. FIGS. 7A-7B provide an illustrative barcode arrangement. In FIG. 7A, each coding region for a first oligonucleotide 701, a second oligonucleotide 703, and a third oligonucleotide 705, has the following features (from surface 702 outward): a tether region 702, a cleavage region 707, a first primer binding region 701, a barcode region 703, a coding region 701, 703, 705, and a second primer binding region 704. The oligonucleotides may be amplified with the use of primers that recognize the first and/or second primer binding regions. Amplification may occur to oligonucleotides attached to the surface or released from the surface (i.e., via cleavage at the cleavage region 707). After sequencing, the barcode region 703, provides an indicator for identifying a characteristic associated with the coding region. In some instances, a barcode comprises a nucleic acid sequence that when joined to a target polynucleotide serves as an identifier of the sample from which the target polynucleotide was derived. Barcodes can be designed at suitable lengths to allow sufficient degree of identification, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 , 36 , 37, 38, 39, 40, 41, 42, 43, 44, 45, 46, 47, 48, 49, 50, 51, 52, 53, 54, 55, or more bases in length. Multiple barcodes, such as 2, 3, 4, 5, 6, 7, 8, 9, 10, or more barcodes, may be used on the same molecule, optionally separated by non-barcode sequences. In some instances, barcodes are shorter than 10, 9, 8, 7, 6, 5, or 4 bases in length. In some instances, barcodes associated with some polynucleotides are of different lengths than barcodes associated with other polynucleotides. In general, barcodes are of sufficient length and comprise sequences that are sufficiently different to allow the identification of samples based on barcodes with which they are associated. In some arrangements, a barcode, and the sample source with which it is associated, can be identified accurately after the mutation, insertion, or deletion of one or more bases in the barcode sequence, such as the mutation, insertion, or deletion of 1, 2, 3, 4, 5, 6, 7, 8, 9, 10, or more bases. In some instances, each barcode in a plurality of barcodes differ from every other barcode in the plurality by at least three base positions, such as at least 3, 4, 5, 6, 7, 8, 9, 10, or more positions. Arrangements provided herein may include a barcode sequence that indicates the nucleic acid sequence encoding for a sequence in a particular region of a digital sequence. For example, a barcode sequence may indicate where in a large file a particular oligonucleotide sequence encodes. In some instances, a barcode sequence may indicate which file a particular oligonucleotide sequence is associated with. In some instances, a barcode sequence includes information associated with the conversion scheme for a particular sequence, providing an added layer of security.

Provided herein are oligonucleotide sequence design schemes where each oligonucleotide sequence in a population of oligonucleotide sequences is designed to have at least one region in common amongst oligonucleotide sequences in that population. For example, all oligonucleotides in the same population may comprise one or more primer regions. The design of sequence-specific primer regions allows for the selection of oligonucleotides to be amplified in selected batches from a large library of multiple oligonucleotides. Each oligonucleotide sequence may comprise at least 1, 2, 3, 4, 5, 6, 7, 8, 9, 10 or more primer binding sequences. A population of oligonucleotide sequences may comprise at least 1, 2, 3, 4, 5, 6, 7, 8, 9, 10, 25, 50, 100, 200, 500, 1000, 5000, 10000, 50000, 100000 or more non-identical binding sequences. Primer binding sequences may comprise 5-100, 10-75, 7-60, 8-60, 10-50, or 10-40 bases in length.

Structures for Oligonucleotide Synthesis

Figure 8:
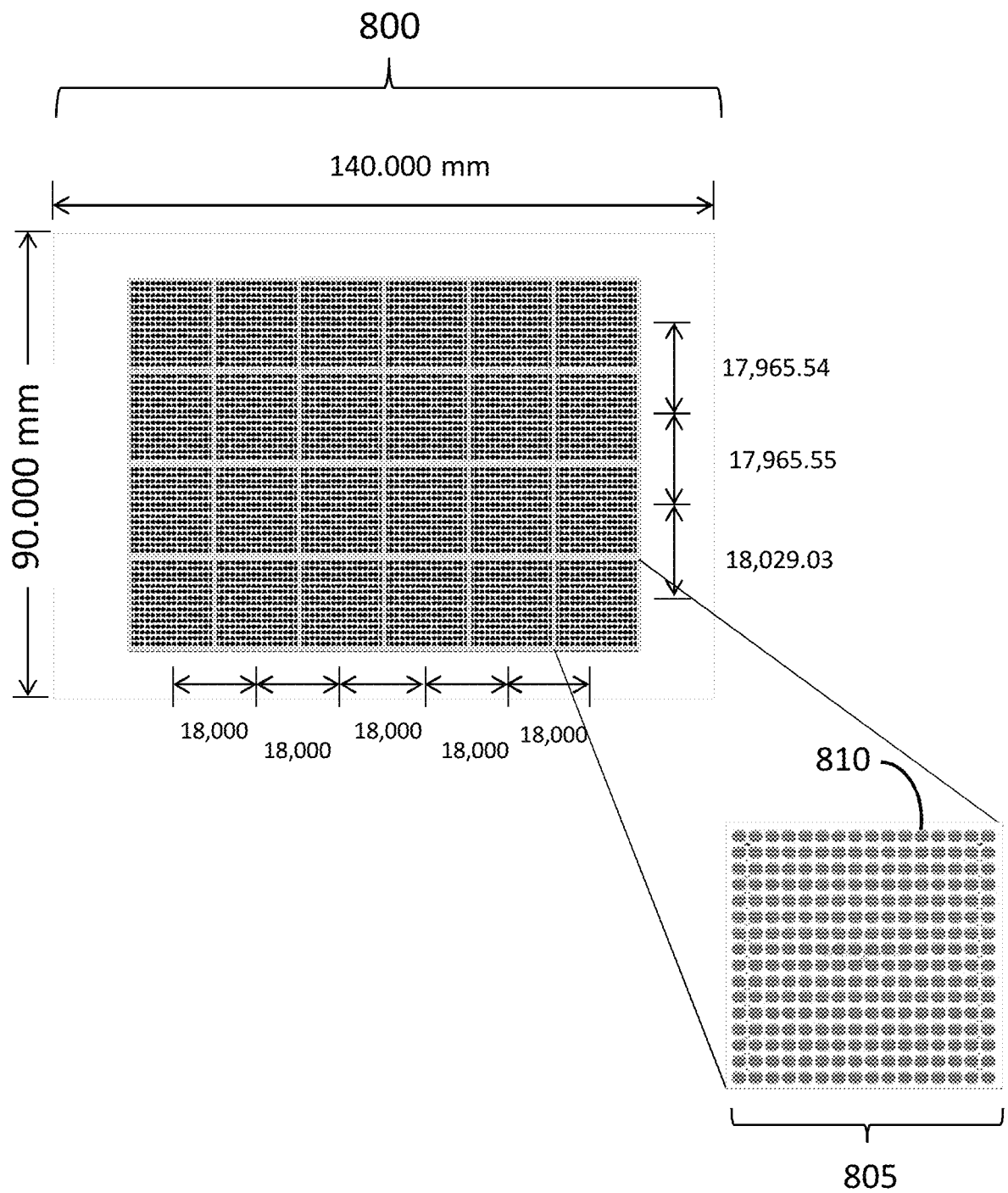
FIG. 8 illustrates a plate configured for oligonucleotide synthesis comprising 24 regions, or sub-fields, each having an array of 256 clusters.
Figure 9:
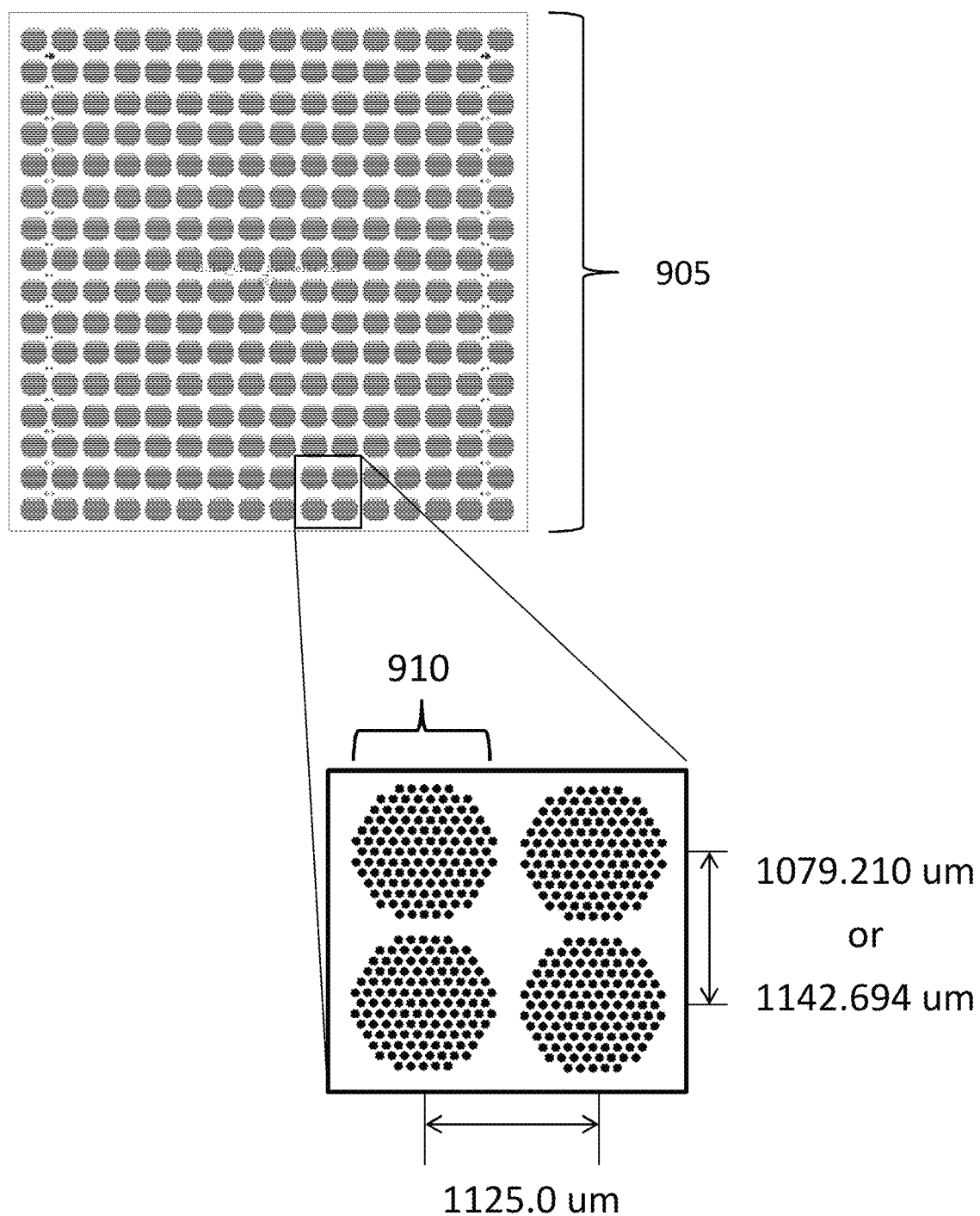
FIG. 9 illustrates a closer view of the sub-field in FIG. 8 having 16×16 of clusters, each cluster having 121 individual loci.
Figure 10:
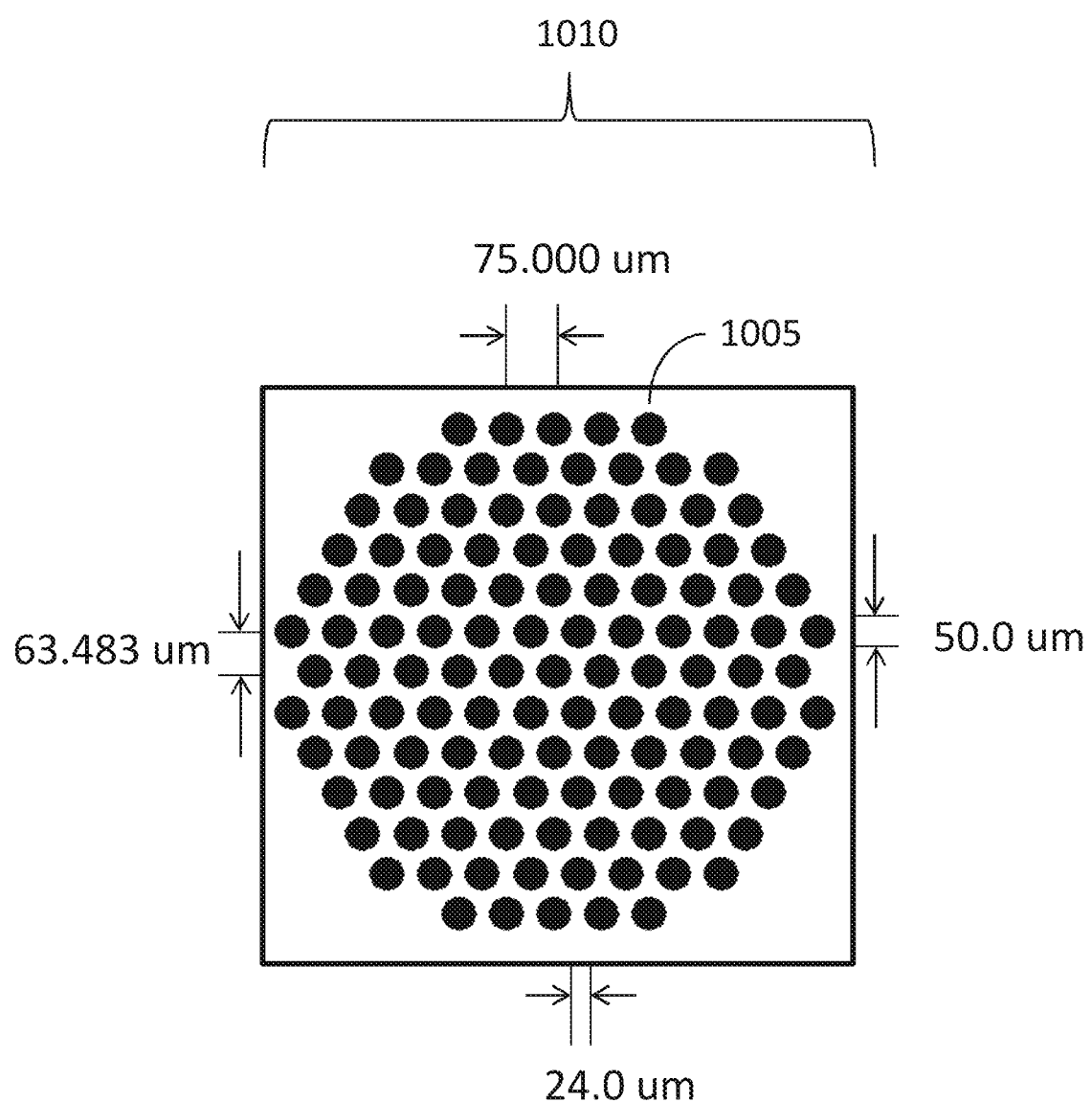
FIG. 10 illustrates a detailed view of the cluster in FIG. 8, where the cluster has 121 loci.
Figure 11A:
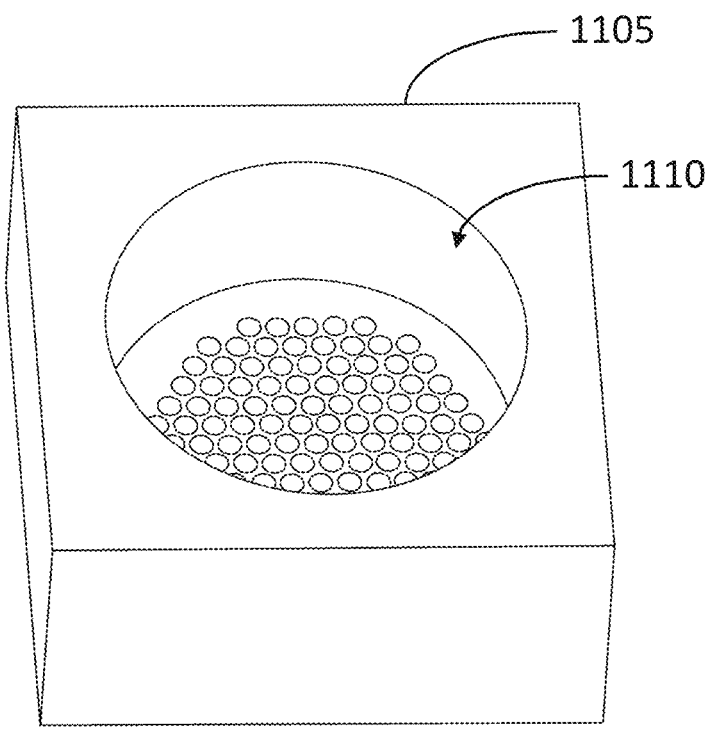
FIG. 11A illustrates a front view of a plate with a plurality of channels.
Figure 11B:
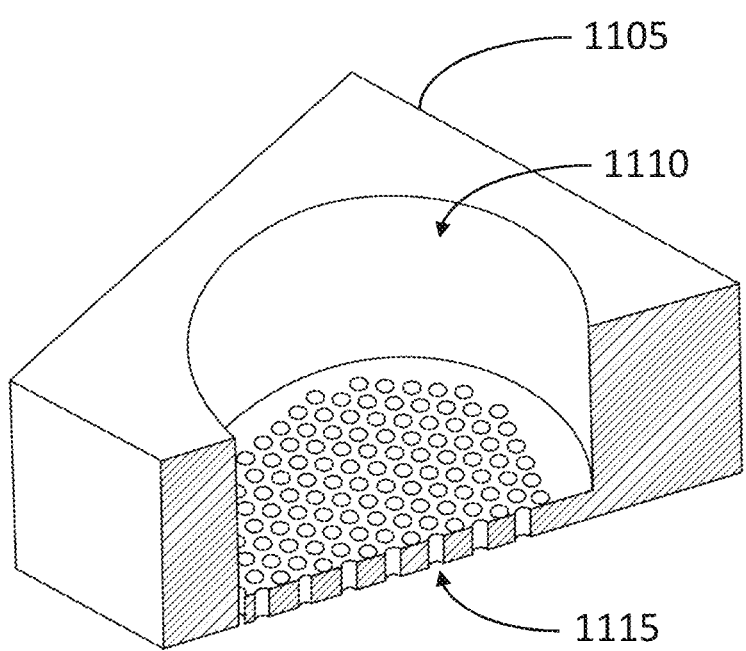
FIG. 11B illustrates a sectional view of plate with a plurality of channels.

Provided herein are rigid or flexibles structures for oligonucleotide synthesis for use with devices, compositions, systems, and methods for bioencryption and/or biodecryption as described herein. In the case of rigid structures, provided herein are devices having structures (e.g., a plate) for the generation of a library of oligonucleotides. An exemplary structure 800 is illustrated in FIG. 8, wherein the structure 800 has about the same size dimensions as a standard 96 well plate: 140 mm by 90 mm. The structure 800 comprises clusters grouped in 24 regions or sub-fields 805, each sub-field 805 comprising an array of 256 clusters 810. An expanded view of an exemplary sub-field 805 is shown in FIG. 9. The structure as seen in FIG. 8 and FIG. 9 may be substantially planar. In the expanded view of four clusters (FIG. 9), a single cluster 910, has a Y axis cluster pitch (distance from center to center of adjacent clusters) of 1079.210 um or 1142.694 um, and an X axis cluster pitch of 1125 um. An illustrative cluster 1010 is depicted in FIG. 10, where the Y axis loci pitch (distance from center to center of adjacent loci) is 63.483 um, and an X axis loci pitch is 75 um. The locus width at the longest part, e.g., diameter for a circular locus, is 50 um and the distance between loci is 24 um. The number of loci 1005 in the exemplary cluster in FIG. 10 is 121. The loci (also referred to as "features"), may be flat, wells, or channels. An exemplary channel arrangement is illustrated in FIGS. 11A-11B where a plate 1105 is illustrated comprising a main channel 1110 and a plurality of channels 1115 connected to the main channel 1110. The connection between the main channel 1110 and the plurality of channels 1115 provides for a fluid communication for flow paths from the main channel 1110 to the each of the plurality of channels 1115. A plate 1105 described herein can comprise multiple main channels 1110. The plurality of channels 1115 collectively forms a cluster within the main channel 1110.

Figure 12A:
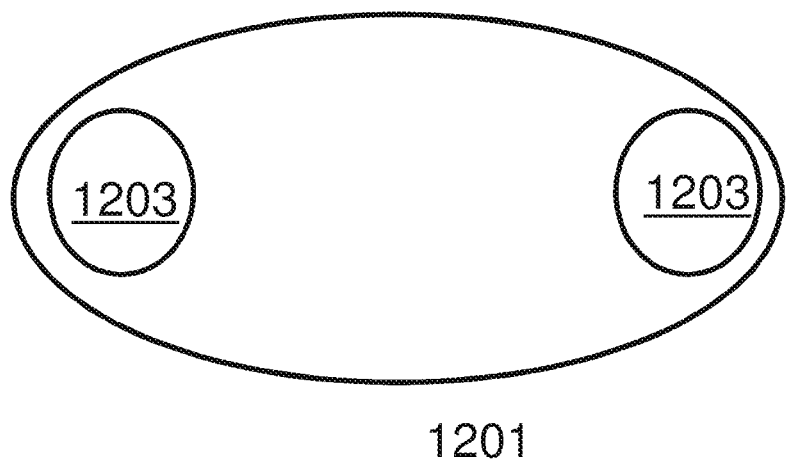
FIGS. 12A-12B depict a continuous loop and reel-to-reel arrangements for flexible structures.
Figure 12B:
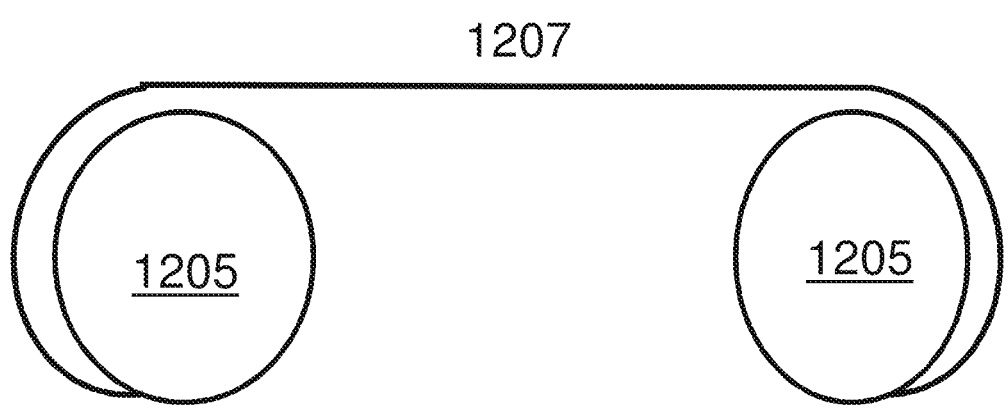
Figure 13A:
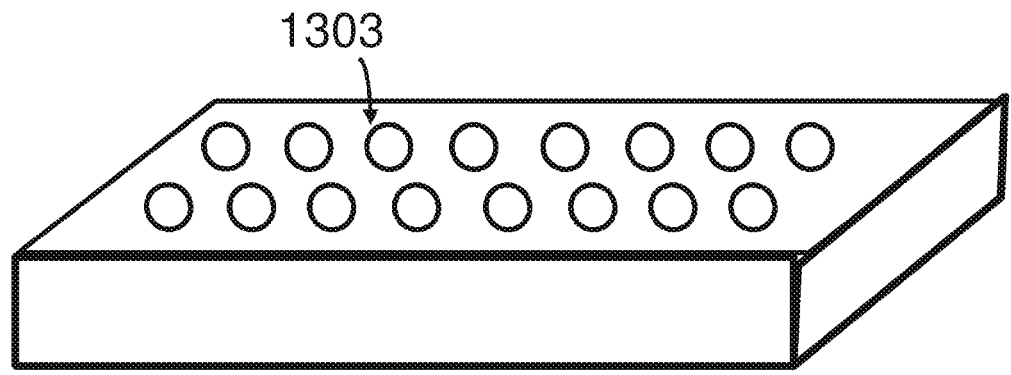
FIGS. 13A-13C depict a zoom in of a flexible structure, having flat features (loci), channels, or wells, respectively.
Figure 13B:
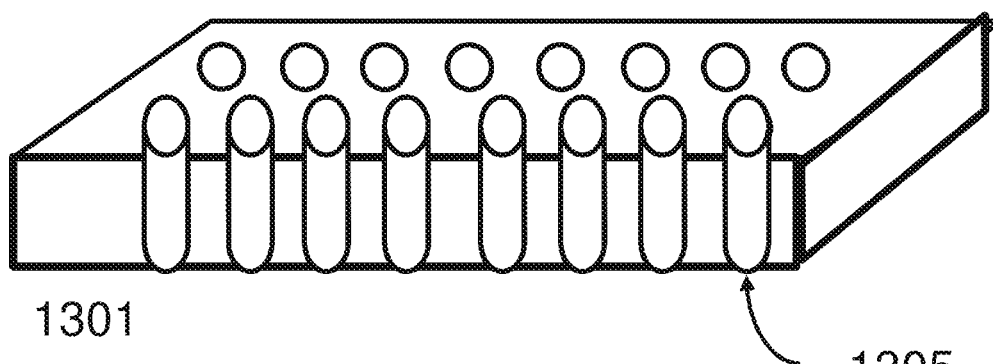
Figure 13C:
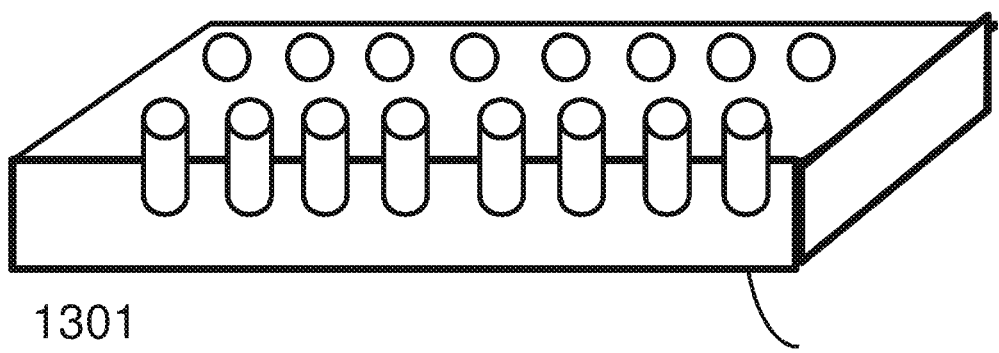

In the case of flexible structures, provided herein are devices wherein the flexible structure comprises a continuous loop 1201 wrapped around one or more fixed structures, e.g., a pair of rollers 1203 or a non-continuous flexible structure 1207 wrapped around separate fixed structures, e.g., a pair reels 1205. See FIGS. 12A-12B. Provided herein are flexible structures having a surface with a plurality of features (loci) for oligonucleotide extension. Each feature in a portion of the flexible structure 1301 may be a substantially planar feature 1303 (e.g., flat), a channel 1305, or a well 1307. See FIGS. 13A-13C. In one exemplary arrangement, each feature of the structure has a width of about 10 um and a distance between the center of each structure of about 21 um. See FIG. 14A. Features may comprise, without limitation, circular, rectangular, tapered, or rounded shapes.

Structures for oligonucleotide synthesis for use with devices, compositions, systems, and methods for bioencryption and/or biodecryption as described herein may comprise a channel. In some instances, a channel described herein has a width to depth (or height) ratio of 1 to 0.01, wherein the width is a measurement of the width at the narrowest segment of the microchannel. In some instances, a channel described herein has a width to depth (or height) ratio of 0.5 to 0.01, wherein the width is a measurement of the width at the narrowest segment of the microchannel. In some instances, a channel described herein has a width to depth (or height) ratio of about 0.01, 0.05, 0.1, 0.15, 0.16, 0.2, 0.5, or 1.

Provided herein are structures for polynucleotide synthesis comprising a plurality of discrete loci, channels, wells or protrusions for polynucleotide synthesis. Structures described herein may comprise a plurality of clusters, each cluster comprising a plurality of wells, loci or channels. Alternatively, described herein are structures that may comprise a homogenous arrangement of wells, loci or channels. In some instances, a structure described herein is provided comprising a plurality of channels corresponding to a plurality of features (loci) within a cluster, wherein the height or depth of the channel is from about 5 um to about 500 um, from about 5 um to about 400 um, from about 5 um to about 300 um, from about 5 um to about 200 um, from about 5 um to about 100 um, from about 5 um to about 50 um, or from about 10 um to about 50 um. In some cases, the height or depth of a channel is less than 100 um, less than 80 um, less than 60 um, less than 40 um or less than 20 um. In some cases, channel height or depth is about 10, 20, 30, 40, 50, 60, 70, 80, 90, 100, 200, 300, 400, 500 um or more. In some instances, the height or depth is at least 10, 25, 50, 75, 100, 200, 300, 400, 500, 600, 700, 800, 900, 1000, or more than 1000 nm. In some instances, the height or depth is in a range of about 10 nm to about 1000 nm, about 25 nm to about 900 nm, about 50 nm to about 800 nm, about 75 nm to about 700 nm, about 100 nm to about 600 nm, or about 200 nm to about 500. In some instances, the height or depth is in a range of about 50 nm to about 1 um.

Structures for oligonucleotide synthesis for use with devices, compositions, systems, and methods for bioencryption and/or biodecryption as described herein may comprise a feature. In some instances, the width of a feature (e.g., substantially planar feature, well, channel, locus, or protrusion) is from about 0.1 um to about 500 um, from about 0.5 um to about 500 um, from about 1 um to about 200 um, from about 1 um to about 100 um, from about 5 um to about 100 um, or from about 0.1 um to about 100 um, for example, about 90 um, 80 um, 70 um, 60 um, 50 um, 40 um, 30 um, 20 um, 10 um, 5 um, 1 um or 0.5 um. In some instances, the width of a feature (e.g., microchannel) is less than about 100 um, 90 um, 80 um, 70 um, 60 um, 50 um, 40 um, 30 um, 20 um or 10 um. In some instances, the width of a feature is at least 10, 25, 50, 75, 100, 200, 300, 400, 500, 600, 700, 800, 900, 1000, or more than 1000 nm. In some instances, the width of a feature is in a range of about 10 nm to about 1000 nm, about 25 nm to about 900 nm, about 50 nm to about 800 nm, about 75 nm to about 700 nm, about 100 nm to about 600 nm, or about 200 nm to about 500. In some instances, the width of a feature is in a range of about 50 nm to about 1000 nm. In some instances, the distance between the center of two adjacent features is from about 0.1 um to about 500 um, 0.5 um to about 500 um, from about 1 um to about 200 um, from about 1 um to about 100 um, from about 5 um to about 200 um, from about 5 um to about 100 um, from about 5 um to about 50 um, or from about 5 um to about 30 um, for example, about 20 um. In some instances, the total width of a feature is about 5um, 10 um, 20 um, 30 um, 40 um, 50 um, 60 um, 70 um, 80 um, 90 um, or 100 um. In some instances, the total width of a feature is about 1 um to 100 um, 30 um to 100 um, or 50 um to 70 um. In some instances, the distance between the center of two adjacent features is from about 0.5 um to about 2 um, from about 0.5 um to about 2 um, from about 0.75 um to about 2 um, from about 1 um to about 2 um, from about 0.2 um to about 1 um, from about 0.5 um to about 1.5 um, from about 0.5 um to about 0.8 um, or from about 0.5 um to about 1 um, for example, about 1 um. In some instances, the total width of a features is about 50 nm, 0.1 um, 0.2 um, 0.3 um, 0.4 um, 0.5 um, 0.6 um, 0.7 um, 0.8 um, 0.9 um, 1 um, 1.1 um, 1.2 um, 1.3 um, 1.4 um, or 1.5 um. In some instances, the total width of a feature is about 0.5 um to 2 um, 0.75 um to 1 um, or 0.9 um to 2 um.

In some instances, each feature supports the synthesis of a population of oligonucleotides having a different sequence than a population of oligonucleotides grown on another feature. Provided herein are surfaces which comprise at least 10, 100, 256, 500, 1000, 2000, 3000, 4000, 5000, 6000, 7000, 8000, 9000, 10000, 11000, 12000, 13000, 14000, 15000, 20000, 30000, 40000, 50000 or more clusters. Provided herein are surfaces which comprise more than 2,000; 5,000; 10,000; 20,000; 30,000; 50,000; 100,000; 200,000; 300,000; 400,000; 500,000; 600,000; 700,000; 800,000; 900,000; 1,000,000; 5,000,000; or 10,000,000 or more distinct features. In some cases, each cluster includes 1, 2, 3, 4, 5, 6, 7, 8, 9, 10, 20, 30, 40, 50, 60, 70, 80, 90, 100, 120, 130, 150, 200, 500 or more features. In some cases, each cluster includes 50 to 500, 50 to 200, 50 to 150, or 100 to 150 features. In some cases, each cluster includes 100 to 150 features. In exemplary arrangements, each cluster includes 109, 121, 130 or 137 features.

Provided herein are features having a width at the longest segment of 5 to 100 um. In some cases, the features have a width at the longest segment of about 30, 35, 40, 45, 50, 55 or 60 um. In some cases, the features are channels having multiple segments, wherein each segment has a center to center distance apart of 5 to 50 um. In some cases, the center to center distance apart for each segment is about 5, 10, 15, 20 or 25 um.

In some instances, the number of distinct oligonucleotides synthesized on the surface of a structure described herein is dependent on the number of distinct features available in the substrate. In some instances, the density of features within a cluster of a substrate is at least or about 1 feature per mm$^2$, 10 features per mm$^2$, 25 features per mm$^2$, 50 features per mm$^2$, 65 features per mm$^2$, 75 features per mm$^2$, 100 features per mm$^2$, 130 features per mm$^2$, 150 features per mm$^2$, 175 features per mm$^2$, 200 features per mm$^2$, 300 features per mm$^2$, 400 features per mm$^2$, 500 features per mm$^2$, 1,000 features per mm$^2$ or more. In some cases, a substrate comprises from about 10 features per mm$^2$ to about 500 mm$^2$, from about 25 features per mm$^2$ to about 400 mm$^2$, from about 50 features per mm$^2$ to about 500 mm$^2$, from about 100 features per mm$^2$ to about 500 mm$^2$, from about 150 features per mm$^2$ to about 500 mm$^2$, from about 10 features per mm$^2$ to about 250 mm$^2$, from about 50 features per mm$^2$ to about 250 mm$^2$, from about 10 features per mm$^2$ to about 200 mm$^2$, or from about 50 features per mm$^2$ to about 200 mm$^2$. In some instances, the distance between the centers of two adjacent features within a cluster is from about 10 um to about 500 um, from about 10 um to about 200 um, or from about 10 um to about 100 um. In some cases, the distance between two centers of adjacent features is greater than about 10 um, 20 um, 30 um, 40 um, 50 um, 60 um, 70 um, 80 um, 90 um or 100 um. In some cases, the distance between the centers of two adjacent features is less than about 200 um, 150 um, 100 um, 80 um, 70 um, 60 um, 50 um, 40 um, 30 um, 20 um or 10 um. In some cases, the distance between the centers of two adjacent features is less than about 10000 nm, 8000 nm, 6000 nm, 4000 nm, 2000 nm 1000 nm, 800 nm, 600 nm, 400 nm, 200 nm, 150 nm, 100 nm, 80 nm, 70 nm, 60 nm, 50 nm, 40 nm, 30 nm, 20 nm or 10 nm. In some instances, each square meter of a structure described herein allows for at least about $10^7$, $10^8$, $10^9$, $10^{10}$, $10^{11}$ features, where each feature supports one oligonucleotide. In some instances, $10^9$ oligonucleotides are supported on less than about 6, 5, 4, 3, 2 or 1 m$^2$ of a structure described herein.

Structures for oligonucleotide synthesis for use with devices, compositions, systems, and methods for bioencryption and/or biodecryption as described herein supports synthesis of a number of oligonucleotides. In some instances, a structure described herein provides support for the synthesis of more than 2,000; 5,000; 10,000; 20,000; 30,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical oligonucleotides. In some cases, the structure provides support for the synthesis of more than 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more oligonucleotides encoding for distinct sequences. In some instances, at least a portion of the oligonucleotides have an identical sequence or are configured to be synthesized with an identical sequence. In some instances, the structure provides a surface environment for the growth of oligonucleotides having at least about 50, 60, 70, 75, 80, 85, 90, 95, 100, 110, 120, 130, 140, 150, 160, 175, 200, 225, 250, 275, 300, 325, 350, 375, 400, 425, 450, 475, 500 bases or more.

In some instances, oligonucleotides are synthesized on distinct features of a structure, wherein each feature supports the synthesis of a population of oligonucleotides. In some cases, each feature supports the synthesis of a population of oligonucleotides having a different sequence than a population of oligonucleotides grown on another locus. In some instances, the features of a structure are located within a plurality of clusters. In some instances, a structure comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a structure comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct features. In some cases, each cluster includes 1, 2, 3, 4, 5, 6, 7, 8, 9, 10, 20, 30, 40, 50, 60, 70, 80, 90, 100, 120, 130, 150 or more features (loci). In some instances, each cluster includes 50 to 500, 100 to 150, or 100 to 200 features. In some instances, each cluster includes 109, 121, 130 or 137 features. In some instances, each cluster includes 5, 6, 7, 8, 9, 10, 11 or 12 features. In some instances, oligonucleotides from distinct features within one cluster have sequences that, when assembled, encode for a contiguous longer oligonucleotide of a predetermined sequence.

Structure Size

Structures for oligonucleotide synthesis for use with devices, compositions, systems, and methods for bioencryption and/or biodecryption as described herein comprise a variety of sizes. In some instances, a structure described herein is about the size of a standard 96 well plate, for example between about 100 and 200 mm by between about 50 and 150 mm. In some instances, a structure described herein has a diameter less than or equal to about 1000 mm, 500 mm, 450 mm, 400 mm, 300 mm, 250 nm, 200 mm, 150 mm, 100 mm or 50 mm. In some instances, the diameter of a substrate is between about 25 mm and 1000 mm, between about 25 mm and about 800 mm, between about 25 mm and about 600 mm, between about 25 mm and about 500 mm, between about 25 mm and about 400 mm, between about 25 mm and about 300 mm, or between about 25 mm and about 200. Non-limiting examples of substrate size include about 300 mm, 200 mm, 150 mm, 130 mm, 100 mm, 76 mm, 51 mm and 25 mm. In some instances, a substrate has a planar surface area of at least about 100 mm$^2$; 200 mm$^2$; 500 mm$^2$; 1,000 mm$^2$; 2,000 mm$^2$; 5,000 mm$^2$; 10,000 mm$^2$; 12,000 mm$^2$; 15,000 mm$^2$; 20,000 mm$^2$; 30,000 mm$^2$; 40,000 mm$^2$; 50,000 mm$^2$ or more. In some instances, the thickness of the substrate is between about 50 mm and about 2000 mm, between about 50 mm and about 1000 mm, between about 100 mm and about 1000 mm, between about 200 mm and about 1000 mm, or between about 250 mm and about 1000 mm. Non-limiting examples of substrate thickness include 275 mm, 375 mm, 525 mm, 625 mm, 675 mm, 725 mm, 775 mm and 925 mm. In some cases, the thickness of the substrate varies with diameter and depends on the composition of the substrate. For example, a structure comprising materials other than silicon may have a different thickness than a silicon structure of the same diameter. Structure thickness may be determined by the mechanical strength of the material used and the structure must be thick enough to support its own weight without cracking during handling. In some instances, a structure is more than about 1, 2, 3, 4, 5, 10, 15, 30, 40, 50 feet in any one dimension.

Materials

Structures for oligonucleotide synthesis for use with devices, compositions, systems, and methods for bioencryption and/or biodecryption as described herein may be fabricated from a variety of materials. In certain instances, the materials from which the substrates/solid supports of the disclosure are fabricated exhibit a low level of oligonucleotide binding. In some situations, material(s) that is (are) transparent to visible and/or UV light can be employed. Materials that are sufficiently conductive, e.g. those that can form uniform electric fields across all or a portion of the substrates/solids support described herein, can be utilized. In some instances, such materials may be connected to an electric ground. In some cases, the substrate or solid support can be heat conductive or insulated. The materials can be chemical resistant and heat resistant to support chemical or biochemical reactions such as a series of oligonucleotide synthesis reactions. For flexible materials, materials of interest can include: nylon, both modified and unmodified, nitrocellulose, polypropylene, and the like.

For rigid materials, specific materials of interest include: glass; fuse silica; silicon, plastics (for example polytetraflouroethylene, polypropylene, polystyrene, polycarbonate, and blends thereof, and the like); and metals (for example, gold, platinum, and the like). The structure can be fabricated from a material selected from the group consisting of silicon, polystyrene, agarose, dextran, cellulosic polymers, polyacrylamides, polydimethylsiloxane (PDMS), and glass. The substrates/solid supports or the microstructures, reactors therein may be manufactured with a combination of materials listed herein or any other suitable material known in the art.

The term "flexible" is used herein to refer to a structure that is capable of being bent, folded or similarly manipulated without breakage. In some cases, a flexible structure is bent at least 30 degrees around a roller. In some cases, a flexible structure is bent at least 180 degrees around a roller. In some cases, a flexible structure is bent at least 270 degrees around a roller. In some instances, a flexible structure is bent about 360 degrees around a roller. In some cases, the roller is less than about 10 cm, 5 cm, 3 cm, 2 cm or 1 cm in radius. In some instances, the flexible structure is bent and straightened repeatedly in either direction at least 100 times without failure (for example, cracking) or deformation at 20° C. In some instances, a flexible structure described herein has a thickness that is amenable to rolling. In some cases, the thickness of the flexible structure described herein is less than about 50 mm, 10 mm, 1 mm, or 0.5 mm.

Exemplary flexible materials for structure described herein include, without limitation, nylon (unmodified nylon, modified nylon, clear nylon), nitrocellulose, polypropylene, polycarbonate, polyethylene, polyurethane, polystyrene, acetal, acrylic, acrylonitrile, butadiene styrene (ABS), polyester films such as polyethylene terephthalate, polymethyl methacrylate or other acrylics, polyvinyl chloride or other vinyl resin, transparent PVC foil, transparent foil for printers, poly(methyl methacrylate) (PMMA), methacrylate copolymers, styrenic polymers, high refractive index polymers, fluorine-containing polymers, polyethersulfone, polyimides containing an alicyclic structure, rubber, fabric, metal foils, and any combination thereof. Various plasticizers and modifiers may be used with polymeric substrate materials to achieve selected flexibility characteristics.

Flexible structures described herein may comprise a plastic material. In some instances, the flexible structure comprises a thermoplastic material. Non-limiting examples of thermoplastic materials include acrylic, acrylonitrile butadiene styrene, nylon, polylactic acid, polybenzimidazole, polycarbonate, polyether sulfone, polyetherether ketone, polyetherimide, polyethylene, polyphenylene oxide, polyphenylene sulfide, polypropylene, polystyrene, polyvinyl chloride, and polytetrafluoroethylene. In some instances, the substrate comprises a thermoplastic material in the polyaryletherketone (PEAK) family. Non-limiting examples of PEAK thermoplastics include polyetherketone (PEK), polyetherketoneketone (PEKK), poly(ether ether ketone ketone) (PEEKK), polyether ether ketone (PEEK), and polyetherketoneetherketoneketone (PEKEKK). In some instances, the flexible structure comprises a thermoplastic material compatible with toluene. In some instances, the flexibility of the plastic material is increased by the addition of a plasticizer. An example of a plasticizer is an ester-based plasticizer, such as phthalate. Phthalate plasticizers include bis(2-ethylhexyl) phthalate (DEHP), diisononly phthalate (DINP), di-n-butyl phthalate (DnBP, DBP), butyl benzyl phthalate (BBzP), diisodecyl phthalate (DIDP), dioctyl phthalate (DOP, DnOP), diisooctyl phthalate (DIOP), diethyl phthalate (DEP), diisobutyl phthalate (DIBP), and di-n-hexyl phthalate. In some instances, modification of the thermoplastic polymer through copolymerization or through the addition of non-reactive side chains to monomers before polymerization also increases flexibility.

Provided herein are flexible structures which may further comprise a fluoroelastomer. Materials having about 80% fluoroelastomers are designated as FKMs. Fluoroelastomers include perfluoro-elastomers (FFKMs) and tetrafluoroethylene/propylene rubbers (FEPM). Fluoroelastomers have five known types. Type 1 FKMs are composed of vinylidene fluoride (VDF) and hexafluoropropylene (HFP) and their fluorine content typically is around 66% by weight. Type 2 FKMs are composed of VDF, HFP, and tetrafluoroethylene (TFE) and typically have between about 68% and 69% fluorine. Type 3 FKMs are composed of VDF, TFE, and perfluoromethylvinylether (PMVE) and typically have between about 62% and 68% fluorine. Type 4 FKMs are composed of propylene, TFE, and VDF and typically have about 67% fluorine. Type 5 FKMs are composed of VDF, HFP, TFE, PMVE, and ethylene.

In some instances, a substrate disclosed herein comprises a computer readable material. Computer readable materials include, without limitation, magnetic media, reel-to-reel tape, cartridge tape, cassette tape, flexible disk, paper media, film, microfiche, continuous tape (e.g., a belt) and any media suitable for storing electronic instructions. In some cases, the substrate comprises magnetic reel-to-reel tape or a magnetic belt. In some instances, the substrate comprises a flexible printed circuit board.

Structures described herein may be transparent to visible and/or UV light. In some instances, structures described herein are sufficiently conductive to form uniform electric fields across all or a portion of a structure. In some instances, structures described herein are heat conductive or insulated. In some instances, the structures are chemical resistant and heat resistant to support a chemical reaction such as an oligonucleotide synthesis reaction. In some instances, the structure is magnetic. In some instances, the structures comprise a metal or a metal alloy.

Structures for oligonucleotide synthesis may be over 1, 2, 5, 10, 30, 50 or more feet long in any dimension. In the case of a flexible structure, the flexible structure is optionally stored in a wound state, e.g., in a reel. In the case of a large rigid structure, e.g., greater than 1 foot in length, the rigid structure can be stored vertically or horizontally.

Encryption Key Markings on the Structure's Surface

Structures for oligonucleotide synthesis for use with devices, compositions, systems, and methods for bioencryption and/or biodecryption as described herein may comprise encryption markings. Provided herein are structures having markings 1401 wherein the markings provide information relating to the source item of information associated with a nearby population of oligonucleotides, an encryption scheme for decrypting the sequence of the nearby population of oligonucleotides, the copy number for the nearby population of oligonucleotides, or any combination thereof. See, e.g., FIGS. 14B-14C. The markings may be visible to the naked eye, or visible under a magnified view using a microscope. In some instances, the markings on the surface are only visible after a treatment condition to expose the marking, such as a heat, chemical or light treatment (e.g., UV or IR light to illuminate the marking). An example ink developed by heat includes, without limitation, cobalt chloride, (which turns blue when heated). Example inks developed by chemical reaction include, without limitation, phenolphthalein, copper sulfate, lead(II) nitrate, cobalt(II) chloride, and cerium oxalate developed by manganese sulfate and hydrogen peroxide.

Surface Preparation

Structures for oligonucleotide synthesis for use with devices, compositions, systems, and methods for bioencryption and/or biodecryption as described herein may comprise a surface for oligonucleotide synthesis. Provided herein are methods to support the immobilization of a biomolecule on a substrate, where a surface of a structure described herein comprises a material and/or is coated with a material that facilitates a coupling reaction with the biomolecule for attachment. To prepare a structure for biomolecule immobilization, surface modifications may be employed that chemically and/or physically alter the substrate surface by an additive or subtractive process to change one or more chemical and/or physical properties of a substrate surface or a selected site or region of the surface. For example, surface modification involves (1) changing the wetting properties of a surface, (2) functionalizing a surface, i.e. providing, modifying or substituting surface functional groups, (3) defunctionalizing a surface, i.e. removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface. In some instances, the surface of a structure is selectively functionalized to produce two or more distinct areas on a structure, wherein at least one area has a different surface or chemical property that another area of the same structure. Such properties include, without limitation, surface energy, chemical termination, surface concentration of a chemical moiety, and the like.

In some instances, a surface of a structure disclosed herein is modified to comprise one or more actively functionalized surfaces configured to bind to both the surface of the substrate and a biomolecule, thereby supporting a coupling reaction to the surface. In some instances, the surface is also functionalized with a passive material that does not efficiently bind the biomolecule, thereby preventing biomolecule attachment at sites where the passive functionalization agent is bound. In some cases, the surface comprises an active layer only defining distinct features for biomolecule support.

In some instances, the surface is contacted with a mixture of functionalization groups which are in any different ratio. In some instances, a mixture comprises at least 2, 3, 4, 5 or more different types of functionalization agents. In some cases, the ratio of the at least two types of surface functionalization agents in a mixture is about 1:1, 1:2, 1:5, 1:10, 2:10, 3:10, 4:10, 5:10, 6:10, 7:10, 8:10, 9:10, or any other ratio to achieve a desired surface representation of two groups. In some instances, desired surface tensions, wettabilities, water contact angles, and/or contact angles for other suitable solvents are achieved by providing a substrate surface with a suitable ratio of functionalization agents. In some cases, the agents in a mixture are chosen from suitable reactive and inert moieties, thus diluting the surface density of reactive groups to a desired level for downstream reactions. In some instances, the mixture of functionalization reagents comprises one or more reagents that bind to a biomolecule and one or more reagents that do not bind to a biomolecule. Therefore, modulation of the reagents allows for the control of the amount of biomolecule binding that occurs at a distinct area of functionalization.

In some instances, a method for substrate functionalization comprises deposition of a silane molecule onto a surface of a substrate. The silane molecule may be deposited on a high energy surface of the substrate. In some instances the high surface energy region includes a passive functionalization reagent. Methods described herein provide for a silane group to bind the surface, while the rest of the molecule provides a distance from the surface and a free hydroxyl group at the end to which a biomolecule attaches. In some instances, the silane is an organofunctional alkoxysilane molecule. Non-limiting examples of organofunctional alkoxysilane molecules include dimethylchloro-octodecyl-silane, methyldichloro-octodecyl-silane, trichloro-octodecyl-silane, and trimethyl-octodecyl-silane, triethyl-octodecyl-silane. In some instances, the silane is an amino silane. Examples of amino silanes include, without limitation, 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide. In some instances, the silane comprises 11-acetoxyundecyltriethoxysilane, n-decyltriethoxysilane, (3-aminopropyl)trimethoxysilane, (3-aminopropyl)triethoxysilane, glycidyloxypropyl/trimethoxysilane, N-(3-triethoxysilylpropyl)-4-hydroxybutyramide, or any combination thereof. In some instances, an active functionalization agent comprises 11-acetoxyundecyltriethoxysilane. In some instances, an active functionalization agent comprises n-decyltriethoxysilane. In some cases, an active functionalization agent comprises glycidyloxypropyltriethoxysilane (GOPS). In some instances, the silane is a fluorosilane. In some instances, the silane is a hydrocarbon silane. In some cases, the silane is 3-iodo-propyltrimethoxysilane. In some cases, the silane is octylchlorosilane.

In some instances, silanization is performed on a surface through self-assembly with organofunctional alkoxysilane molecules. The organofunctional alkoxysilanes are classified according to their organic functions. Non-limiting examples of siloxane functionalizing reagents include hydroxyalkyl siloxanes (silylate surface, functionalizing with diborane and oxidizing the alcohol by hydrogen peroxide), diol (dihydroxyalkyl) siloxanes (silylate surface, and hydrolyzing to diol), aminoalkyl siloxanes (amines require no intermediate functionalizing step), glycidoxysilanes (3-glycidoxypropyl-dimethyl-ethoxysilane, glycidoxy-trimethoxysilane), mercaptosilanes (3-mercaptopropyl-trimethoxysilane, 3-4 epoxycyclohexyl-ethyltrimethoxysilane or 3-mercaptopropyl-methyl-dimethoxysilane), bicyclohepthenyl-trichlorosilane, butyl-aldehydr-trimethoxysilane, or dimeric secondary aminoalkyl siloxanes. Exemplary hydroxyalkyl siloxanes include allyl trichlorochlorosilane turning into 3-hydroxypropyl, or 7-oct-1-enyl trichlorochlorosilane turning into 8-hydroxyoctyl. The diol (dihydroxyalkyl) siloxanes include glycidyl trimethoxysilane-derived (2,3-dihydroxypropyloxy)propyl (GOPS). The aminoalkyl siloxanes include 3-aminopropyl trimethoxysilane turning into 3-aminopropyl (3-aminopropyl-triethoxysilane, 3-aminopropyl-diethoxy-methylsilane, 3-aminopropyl-dimethyl-ethoxysilane, or 3-aminopropyl-trimethoxysilane). In some cases, the dimeric secondary aminoalkyl siloxanes is bis (3-trimethoxysilylpropyl) amine turning into bis(silyloxylpropyl)amine.

Active functionalization areas may comprise one or more different species of silanes, for example, 1, 2, 3, 4, 5, 6, 7, 8, 9, 10 or more silanes. In some cases, one of the one or more silanes is present in the functionalization composition in an amount greater than another silane. For example, a mixed silane solution having two silanes comprises a 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 75:25, 70:30, 65:35, 60:40, 55:45 ratio of one silane to another silane. In some instances, an active functionalization agent comprises 11-acetoxyundecyltriethoxysilane and n-decyltriethoxysilane. In some instances, an active functionalization agent comprises 11-acetoxyundecyltriethoxysilane and n-decyltriethoxysilane in a ratio from about 20:80 to about 1:99, or about 10:90 to about 2:98, or about 5:95.

In some instances, functionalization comprises deposition of a functionalization agent to a structure by any deposition technique, including, but not limiting to, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD), physical vapor deposition (e.g., sputter deposition, evaporative deposition), and molecular layer deposition (MLD).

Any step or component in the following functionalization process be omitted or changed in accordance with properties desired of the final functionalized substrate. In some cases, additional components and/or process steps are added to the process workflows embodied herein. In some instances, a substrate is first cleaned, for example, using a piranha solution. An example of a cleaning process includes soaking a substrate in a piranha solution (e.g., 90% $H_2SO_4$, 10% $H_2O_2$) at an elevated temperature (e.g., 120° C.) and washing (e.g., water) and drying the substrate (e.g., nitrogen gas). The process optionally includes a post piranha treatment comprising soaking the piranha treated substrate in a basic solution (e.g., $NH_4OH$) followed by an aqueous wash (e.g., water). In some instances, a surface of a structure is plasma cleaned, optionally following the piranha soak and optional post piranha treatment. An example of a plasma cleaning process comprises an oxygen plasma etch. In some instances, the surface is deposited with an active functionalization agent following by vaporization. In some instances, the substrate is actively functionalized prior to cleaning, for example, by piranha treatment and/or plasma cleaning.

The process for surface functionalization optionally comprises a resist coat and a resist strip. In some instances, following active surface functionalization, the substrate is spin coated with a resist, for example, SPR™ 3612 positive photoresist. The process for surface functionalization, in various instances, comprises lithography with patterned functionalization. In some instances, photolithography is performed following resist coating. In some instances, after lithography, the surface is visually inspected for lithography defects. The process for surface functionalization, in some instances, comprises a cleaning step, whereby residues of the substrate are removed, for example, by plasma cleaning or etching. In some instances, the plasma cleaning step is performed at some step after the lithography step.

In some instances, a surface coated with a resist is treated to remove the resist, for example, after functionalization and/or after lithography. In some cases, the resist is removed with a solvent, for example, with a stripping solution comprising N-methyl-2-pyrrolidone. In some cases, resist stripping comprises sonication or ultrasonication. In some instances, a resist is coated and stripped, followed by active functionalization of the exposed areas to create a desired differential functionalization pattern.

In some instances, the methods and compositions described herein relate to the application of photoresist for the generation of modified surface properties in selective areas, wherein the application of the photoresist relies on the fluidic properties of the surface defining the spatial distribution of the photoresist. Without being bound by theory, surface tension effects related to the applied fluid may define the flow of the photoresist. For example, surface tension and/or capillary action effects may facilitate drawing of the photoresist into small structures in a controlled fashion before the resist solvents evaporate. In some instances, resist contact points are pinned by sharp edges, thereby controlling the advance of the fluid. The underlying structures may be designed based on the desired flow patterns that are used to apply photoresist during the manufacturing and functionalization processes. A solid organic layer left behind after solvents evaporate may be used to pursue the subsequent steps of the manufacturing process. Structures may be designed to control the flow of fluids by facilitating or inhibiting wicking effects into neighboring fluidic paths. For example, a structure is designed to avoid overlap between top and bottom edges, which facilitates the keeping of the fluid in top structures allowing for a particular disposition of the resist. In an alternative example, the top and bottom edges overlap, leading to the wicking of the applied fluid into bottom structures. Appropriate designs may be selected accordingly, depending on the desired application of the resist.

In some instances, a structure described herein has a surface that comprises a material having a thickness of at least or at least about 0.1 nm, 0.5 nm, 1 nm, 2 nm, 5 nm, 10 nm or 25 nm that comprises a reactive group capable of binding nucleosides. Exemplary surfaces include, without limitation, glass and silicon, such as silicon dioxide and silicon nitride. In some cases, exemplary surfaces include nylon and PMMA.

In some instances, electromagnetic radiation in the form of UV light is used for surface patterning. In some instances, a lamp is used for surface patterning, and a mask mediates exposure locations of the UV light to the surface. In some instances, a laser is used for surface patterning, and a shutter opened/closed state controls exposure of the UV light to the surface. The laser arrangement may be used in combination with a flexible structure that is capable of moving. In such an arrangement, the coordination of laser exposure and flexible structure movement is used to create patterns of one or more agents having differing nucleoside coupling capabilities.

Material Deposition Systems

Provided herein are systems and devices for the deposition and storage of biomolecules on a structure described herein. In some instances, the biomolecules are oligonucleotides that store encoded information in their sequences. In some instances, the system comprises a surface of a structure to support biomolecule attachment and/or a device for application of a biomolecule to the surface of the substrate. In an example, the device for biomolecule application is an oligonucleotide synthesizer. In some instances, the system comprises a device for treating the substrate with a fluid, for example, a flow cell. In some instances, the system comprises a device for moving the substrate between the application device and the treatment device. For instances where the substrate is a reel-to-reel tape, the system may comprise two or more reels that allow for access of different portions of the substrate to the application and optional treatment device at different times.

Figure 15:
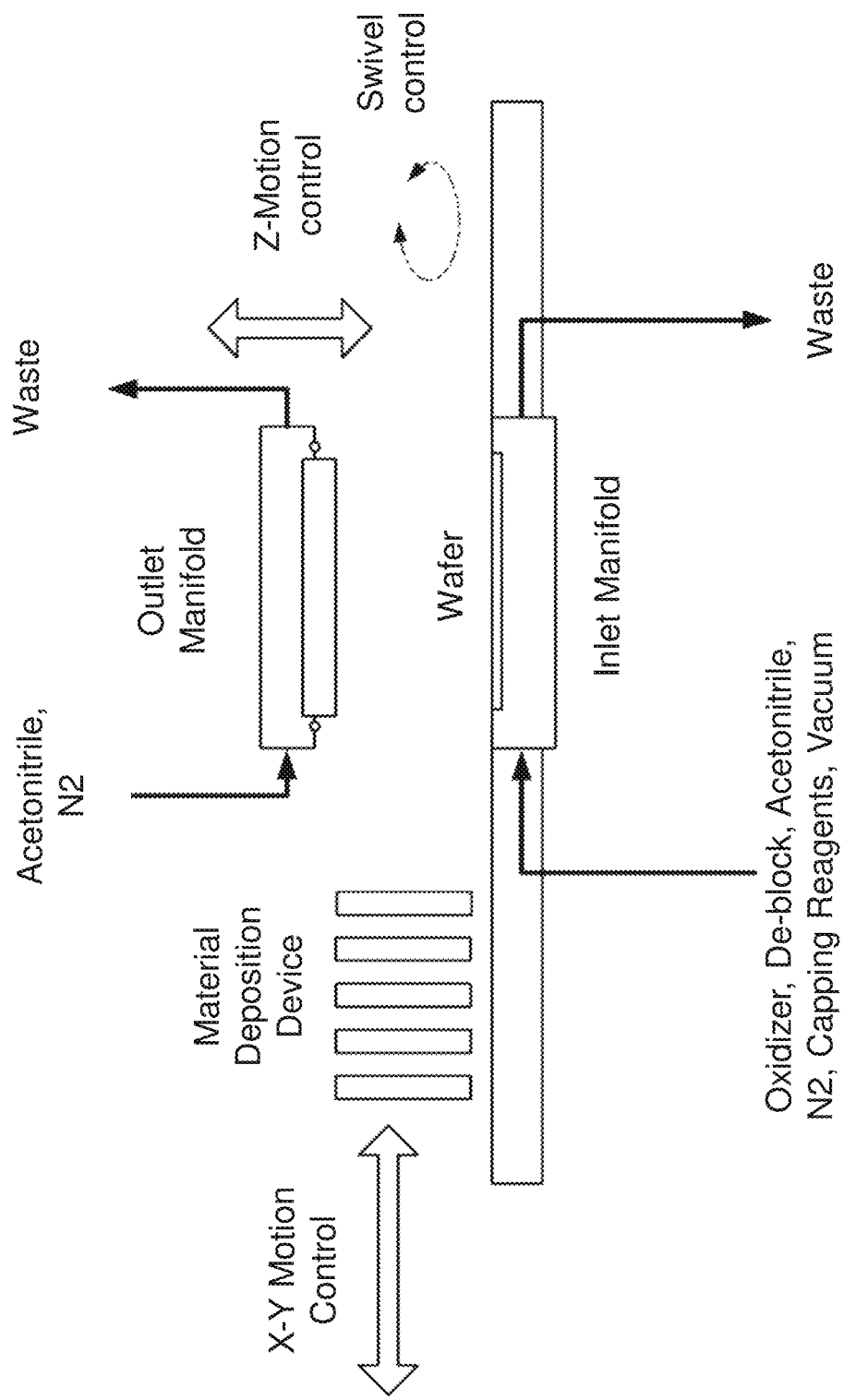
FIG. 15 illustrates an oligonucleotide synthesis material deposition device.

A first example of an oligonucleotide material deposition system for oligonucleotide synthesis is shown in FIG. 15. The system includes a material deposition device that moves in the X-Y direction to align with the location of the substrate. The material deposition device can also move in the Z direction to seal with the substrate, forming a resolved reactor. A resolved reactor is configured to allow for the transfer of fluid, including oligonucleotides and/or reagents, from the substrate to a capping element and/or vice versa. As shown in FIG. 15, fluid may pass through either or both the substrate and the capping element and includes, without limitation, coupling reagents, capping reagents, oxidizers, de-blocking agents, acetonitrile and nitrogen gas. Examples of devices that are capable of high resolution droplet deposition include the printhead of inkjet printers and laser printers. The devices useful in the systems and methods described herein achieve a resolution from about 100 dots per inch (DPI) to about 50,000 DPI; from about 100 DPI to about 20,000 DPI; from about 100 DPI to about 10,000 DPI; from about 100 DPI to about 5,000 DPI; from about 1,000 DPI to about 20,000 DPI; or from about 1,000 DPI to about 10,000 DPI. In some instances, the devices have a resolution at least about 1,000; 2,000; 3,000; 4,000; 5,000; 10,000; 12,000 DPI, or 20,000 DPI. The high resolution deposition performed by the device is related to the number and density of each nozzle that corresponds to a feature of the substrate.

Figure 16:
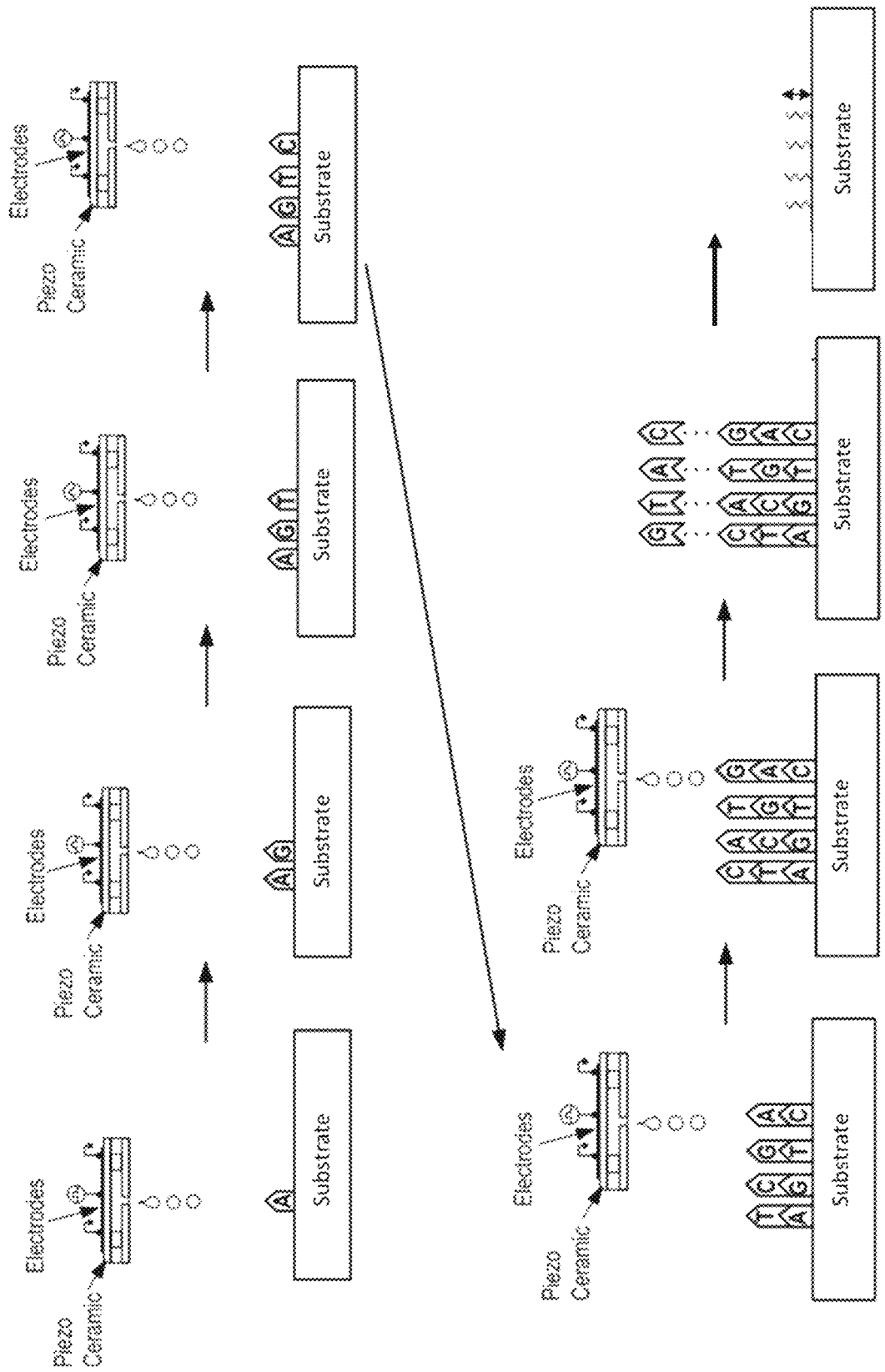
FIG. 16 illustrates an oligonucleotide synthesis workflow.

An exemplary process workflow for de novo synthesis of an oligonucleotide on a substrate using an oligonucleotide synthesizer is shown in FIG. 16. Droplets comprising oligonucleotide synthesis reagents are released from the material deposition device to the substrate in a stepwise manner, wherein the material deposition device has a piezo ceramic material and electrodes to convert electrical signals into a mechanical signal for releasing the droplets. The droplets are released to specific locations on the surface of the substrate one nucleobase at a time to generate a plurality of synthesized oligonucleotides having predetermined sequences that encode data. In some cases, the synthesized oligonucleotides are stored on the substrate. Nucleic acid reagents may be deposited on the substrate surface in a non-continuous, or drop-on-demand method. Examples of such methods include the electromechanical transfer method, electric thermal transfer method, and electrostatic attraction method. In the electromechanical transfer method, piezoelectric elements deformed by electrical pulses cause the droplets to be ejected. In the electric thermal transfer method, bubbles are generated in a chamber of the device, and the expansive force of the bubbles causes the droplets to be ejected. In the electrostatic attraction method, electrostatic force of attraction is used to eject the droplets onto the substrate. In some cases, the drop frequency is from about 5 KHz to about 500 KHz; from about 5 KHz to about 100 KHz; from about 10 KHz to about 500 KHz; from about 10 KHz to about 100 KHz; or from about 50 KHz to about 500 KHz. In some cases, the frequency is less than about 500 KHz, 200 KHz, 100 KHz, or 50 KHz.

The size of the droplets dispensed correlates to the resolution of the device. In some instances, the devices deposit droplets of reagents at sizes from about 0.01 pl to about 20 pl, from about 0.01 pl to about 10 pl, from about 0.01 pl to about 1 pl, from about 0.01 pl to about 0.5 pl, from about 0.01 pl to about 0.01 pl, or from about 0.05 pl to about 1 pl. In some instances, the droplet size is less than about 1 pl, 0.5 pl, 0.2 pl, 0.1 pl, or 0.05 pl. The size of droplets dispensed by the device is correlated to the diameters of deposition nozzles, wherein each nozzle is capable of depositing a reagent onto a feature of the substrate. In some instances, a deposition device of an oligonucleotide synthesizer comprises from about 100 to about 10,000 nozzles; from about 100 to about 5,000 nozzles; from about 100 to about 3,000 nozzles; from about 500 to about 10,000 nozzles; or from about 100 to about 5,000 nozzles. In some cases, the deposition device comprises greater than 1,000; 2,000; 3,000; 4,000; 5,000; or 10,000 nozzles. In some instances, each material deposition device comprises a plurality of nozzles, where each nozzle is optionally configured to correspond to a feature on a substrate. Each nozzle may deposit a reagent component that is different from another nozzle. In some instances, each nozzle deposits a droplet that covers one or more features of the substrate. In some instances, one or more nozzles are angled. In some instances, multiple deposition devices are stacked side by side to achieve a fold increase in throughput. In some cases, the gain is 2×, 4×, 8× or more. An example of a deposition device is Samba Printhead (Fujifilm). A Samba Printhead may be used with the Samba Web Administration Tool (SWAT).

The number of deposition sites may be increased by using and rotating the same deposition device by a certain degree or saber angle. By rotating the deposition device, each nozzle is jetted with a certain amount of delay time corresponding to the saber angle. This unsynchronized jetting creates a cross talk among the nozzles. Therefore, when the droplets are jetting at a certain saber angle different from 0 degrees, the droplet volume from the nozzle could be different.

In some arrangements, the configuration of an oligonucleotide synthesis system allows for a continuous oligonucleotide synthesis process that exploits the flexibility of a substrate for traveling in a reel-to-reel type process. This synthesis process operates in a continuous production line manner with the substrate travelling through various stages of oligonucleotide synthesis using one or more reels to rotate the position of the substrate. In an exemplary embodiment, an oligonucleotide synthesis reaction comprises rolling a substrate: through a solvent bath, beneath a deposition device for phosphoramidite deposition, through a bath of oxidizing agent, through an acetonitrile wash bath, and through a deblock bath. Optionally, the tape is also traversed through a capping bath. A reel-to-reel type process allows for the finished product of a substrate comprising synthesized oligonucleotides to be easily gathered on a take-up reel, where it can be transported for further processing or storage.

In some arrangements, oligonucleotide synthesis proceeds in a continuous process as a continuous flexible tape is conveyed along a conveyor belt system Similar to the reel-to-reel type process, oligonucleotide synthesis on a continuous tape operates in a production line manner, with the substrate travelling through various stages of oligonucleotide synthesis during conveyance. However, in a conveyor belt process, the continuous tape revisits an oligonucleotide synthesis step without rolling and unrolling of the tape, as in a reel-to-reel process. In some arrangements, oligonucleotide synthesis steps are partitioned into zones and a continuous tape is conveyed through each zone one or more times in a cycle. For example, an oligonucleotide synthesis reaction may comprise (1) conveying a substrate through a solvent bath, beneath a deposition device for phosphoramidite deposition, through a bath of oxidizing agent, through an acetonitrile wash bath, and through a block bath in a cycle; and then (2) repeating the cycles to achieve synthesized oligonucleotides of a predetermined length. After oligonucleotide synthesis, the flexible substrate is removed from the conveyor belt system and, optionally, rolled for storage. Rolling may be around a reel, for storage.

In an exemplary arrangement, a flexible substrate comprising thermoplastic material is coated with nucleoside coupling reagent. The coating is patterned into features such that each feature has diameter of about 10 um, with a center-to-center distance between two adjacent features of about 21 um. In this instance, the feature size is sufficient to accommodate a sessile drop volume of 0.2 pl during an oligonucleotide synthesis deposition step. In some cases, the feature density is about 2.2 billion features per $m^2$ (1 feature/$441 \times 10^{-12}$ $m^2$). In some cases, a 4.5 $m^2$ substrate comprise about 10 billion features, each with a 10 um diameter.

A material deposition device described herein may comprise about 2,048 nozzles that each deposit about 100,000 droplets per second at 1 nucleobase per droplet. For each deposition device, at least about $1.75 \times 10^{13}$ nucleobases are deposited on the substrate per day. In some instances, 100 to 500 nucleobase oligonucleotides are synthesized. In some cases, 200 nucleobase oligonucleotides are synthesized. Optionally, over 3 days, at a rate of about $1.75 \times 10^{13}$ bases per day, at least about $262.5 \times 10^9$ oligonucleotides are synthesized.

In some arrangements, a device for application of one or more reagents to a substrate during a synthesis reaction is configured to deposit reagents and/or nucleotide monomers for nucleoside phosphoramidite based synthesis. Reagents for oligonucleotide synthesis include reagents for oligonucleotide extension and wash buffers. As non-limiting examples, the device deposits cleaning reagents, coupling reagents, capping reagents, oxidizers, de-blocking agents, acetonitrile, gases such as nitrogen gas, and any combination thereof. In addition, the device optionally deposits reagents for the preparation and/or maintenance of substrate integrity. In some instances, the oligonucleotide synthesizer deposits a drop having a diameter less than about 200 um, 100 um, or 50 um in a volume less than about 1000, 500, 100, 50, or 20 pl. In some cases, the oligonucleotide synthesizer deposits between about 1 and 10000, 1 and 5000, 100 and 5000, or 1000 and 5000 droplets per second.

In some arrangements, during oligonucleotide synthesis, the substrate is positioned within and/or sealed within a flow cell. The flow cell may provide continuous or discontinuous flow of liquids such as those comprising reagents necessary for reactions within the substrate, for example, oxidizers and/or solvents. The flow cell may provide continuous or discontinuous flow of a gas, such as nitrogen, for drying the substrate typically through enhanced evaporation of a volatile substrate. A variety of auxiliary devices are useful to improve drying and reduce residual moisture on the surface of the substrate. Examples of such auxiliary drying devices include, without limitation, a vacuum source, depressurizing pump and a vacuum tank. In some cases, an oligonucleotide synthesis system comprises one or more flow cells, such as 2, 3, 4, 5, 6, 7, 8, 9, 10, or 20 and one or more substrates, such as 2, 3, 4, 5, 6, 7, 8, 9, 10 or 20. In some cases, a flow cell is configured to hold and provide reagents to the substrate during one or more steps in a synthesis reaction. In some instances, a flowcell comprises a lid that slides over the top of a substrate and can be clamped into place to form a pressure tight seal around the edge of the substrate. An adequate seal includes, without limitation, a seal that allows for about 1, 2, 3, 4, 5, 6, 7, 8, 9 or 10 atmospheres of pressure. In some cases, the lid of the flow cell is opened to allow for access to an application device such as an oligonucleotide synthesizer. In some cases, one or more steps of an oligonucleotide synthesis method are performed on a substrate within a flow cell, without the transport of the substrate.

In some arrangements, a device for treating a substrate with a fluid comprises a spray bar. Nucleotide monomers may be applied onto a substrate surface then a spray bar sprays the substrate surface with one or more treatment reagents using spray nozzles of the spray bar. In some arrangements, the spray nozzles are sequentially ordered to correlate with different treatment steps during oligonucleotide synthesis. The chemicals used in different process steps may be changed in the spray bar to readily accommodate changes in a synthesis method or between steps of a synthesis method. In some instances, the spray bar continuously sprays a given chemistry on a surface of a substrate as the substrate moves past the spray bar. In some cases, the spray bar deposits over a wide area of a substrate, much like the spray bars used in lawn sprinklers. In some instances, the spray bar nozzles are positioned to provide a uniform coat of treatment material to a given area of a substrate.

In some instances, an oligonucleotide synthesis system comprises one or more elements useful for downstream processing of synthesized oligonucleotides. As an example, the system comprises a temperature control element such as a thermal cycling device. In some instances, the temperature control element is used with a plurality of resolved reactors to perform nucleic acid assembly such as PCA and/or nucleic acid amplification such as PCR.

De Novo Oligonucleotide Synthesis

Provided herein are systems and methods for oligonucleotide synthesis of a high density of oligonucleotides on a substrate in a short amount of time for use with devices, compositions, systems, and methods for bioencryption and/or biodecryption as described herein. In some instances, the substrate is a flexible substrate. In some instances, at least about $10^{10}$, $10^{11}$, $10^{12}$, $10^{13}$, $10^{14}$, or $10^{15}$ bases are synthesized in one day. In some instances, at least about $10 \times 10^8$, $10 \times 10^9$, $10 \times 10^{10}$, $10 \times 10^{11}$, or $10 \times 10^{12}$ oligonucleotides are synthesized in one day. In some cases, each oligonucleotide synthesized comprises at least about 20, 50, 100, 200, 300, 400 or 500 nucleobases. In some cases, these bases are synthesized with a total average error rate of less than about 1 in 100; 200; 300; 400; 500; 1000; 2000; 5000; 10000; 15000; 20000 bases. In some instances, these error rates are for at least 50%, 60%, 70%, 80%, 90%, 95%, 98%, 99%, 99.5%, or more of the oligonucleotides synthesized. In some instances, these at least 90%, 95%, 98%, 99%, 99.5%, or more of the oligonucleotides synthesized do not differ from a predetermined sequence for which they encode. In some instances, the error rate for synthesized oligonucleotides on a substrate using the methods and systems described herein is less than about 1 in 200. In some instances, the error rate for synthesized oligonucleotides on a substrate using the methods and systems described herein is less than about 1 in 1,000. In some instances, the error rate for synthesized oligonucleotides on a substrate using the methods and systems described herein is less than about 1 in 2,000. In some instances, the error rate for synthesized oligonucleotides on a substrate using the methods and systems described herein is less than about 1 in 3,000. In some instances, the error rate for synthesized oligonucleotides on a substrate using the methods and systems described herein is less than about 1 in 5,000. Individual types of error rates include mismatches, deletions, insertions, and/or substitutions for the oligonucleotides synthesized on the substrate. The term "error rate" refers to a comparison of the collective amount of synthesized oligonucleotide to an aggregate of predetermined oligonucleotide sequences. In some instances, synthesized oligonucleotides disclosed herein comprise a tether of 12 to 25 bases. In some instances, the tether comprises 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more bases.

A suitable method for oligonucleotide synthesis on a substrate of this disclosure is a phosphoramidite method comprising the controlled addition of a phosphoramidite building block, i.e. nucleoside phosphoramidite, to a growing oligonucleotide chain in a coupling step that forms a phosphite triester linkage between the phosphoramidite building block and a nucleoside bound to the substrate. In some instances, the nucleoside phosphoramidite is provided to the substrate activated. In some instances, the nucleoside phosphoramidite is provided to the substrate with an activator. In some instances, nucleoside phosphoramidites are provided to the substrate in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition and linkage of a nucleoside phosphoramidite in the coupling step, the substrate is optionally washed. In some instances, the coupling step is repeated one or more additional times, optionally with a wash step between nucleoside phosphoramidite additions to the substrate. In some instances, an oligonucleotide synthesis method used herein comprises 1, 2, 3 or more sequential coupling steps. Prior to coupling, in many cases, the nucleoside bound to the substrate is deprotected by removal of a protecting group, where the protecting group functions to prevent polymerization. A common protecting group is 4,4'-dimethoxytrityl (DMT).

Following coupling, phosphoramidite oligonucleotide synthesis methods optionally comprise a capping step. In a capping step, the growing oligonucleotide is treated with a capping agent. A capping step generally serves to block unreacted substrate-bound 5'-OH groups after coupling from further chain elongation, preventing the formation of oligonucleotides with internal base deletions. Further, phosphoramidites activated with 1H-tetrazole often react, to a small extent, with the O6 position of guanosine. Without being bound by theory, upon oxidation with $I_2$/water, this side product, possibly via O6-N7 migration, undergoes depurination. The apurinic sites can end up being cleaved in the course of the final deprotection of the oligonucleotide thus reducing the yield of the full-length product. The O6 modifications may be removed by treatment with the capping reagent prior to oxidation with $I_2$/water. In some instances, inclusion of a capping step during oligonucleotide synthesis decreases the error rate as compared to synthesis without capping. As an example, the capping step comprises treating the substrate-bound oligonucleotide with a mixture of acetic anhydride and 1-methylimidazole. Following a capping step, the substrate is optionally washed.

Following addition of a nucleoside phosphoramidite, and optionally after capping and one or more wash steps, the substrate bound growing nucleic acid may be oxidized. The oxidation step comprises oxidizing the phosphite triester into a tetracoordinated phosphate triester, a protected precursor of the naturally occurring phosphate diester internucleoside linkage. In some instances, oxidation of the growing oligonucleotide is achieved by treatment with iodine and water, optionally in the presence of a weak base such as a pyridine, lutidine, or collidine. Oxidation is sometimes carried out under anhydrous conditions using tert-Butyl hydroperoxide or (1S)-(+)-(10-camphorsulfonyl)-oxaziridine (CSO). In some methods, a capping step is performed following oxidation. A second capping step allows for substrate drying, as residual water from oxidation that may persist can inhibit subsequent coupling. Following oxidation, the substrate and growing oligonucleotide is optionally washed. In some instances, the step of oxidation is substituted with a sulfurization step to obtain oligonucleotide phosphorothioates, wherein any capping steps can be performed after the sulfurization. Many reagents are capable of the efficient sulfur transfer, including, but not limited to, 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

In order for a subsequent cycle of nucleoside incorporation to occur through coupling, a protected 5' end of the substrate bound growing oligonucleotide must be removed so that the primary hydroxyl group can react with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound oligonucleotide and thus reduce the yield of the desired full-length product. Methods and compositions described herein provide for controlled deblocking conditions limiting undesired depurination reactions. In some instances, the substrate bound oligonucleotide is washed after deblocking. In some cases, efficient washing after deblocking contributes to synthesized oligonucleotides having a low error rate.

Methods for the synthesis of oligonucleotides on the substrates described herein typically involve an iterating sequence of the following steps: application of a protected monomer to a surface of a substrate feature to link with either the surface, a linker or with a previously deprotected monomer; deprotection of the applied monomer so that it can react with a subsequently applied protected monomer; and application of another protected monomer for linking. One or more intermediate steps include oxidation and/or sulfurization. In some instances, one or more wash steps precede or follow one or all of the steps.

In some instances, oligonucleotides are synthesized with photolabile protecting groups, where the hydroxyl groups generated on the surface are blocked by photolabile-protecting groups. When the surface is exposed to UV light, such as through a photolithographic mask, a pattern of free hydroxyl groups on the surface may be generated. These hydroxyl groups can react with photoprotected nucleoside phosphoramidites, according to phosphoramidite chemistry. A second photolithographic mask can be applied and the surface can be exposed to UV light to generate second pattern of hydroxyl groups, followed by coupling with 5'-photoprotected nucleoside phosphoramidite. Likewise, patterns can be generated and oligomer chains can be extended. Without being bound by theory, the lability of a photocleavable group depends on the wavelength and polarity of a solvent employed and the rate of photocleavage may be affected by the duration of exposure and the intensity of light. This method can leverage a number of factors such as accuracy in alignment of the masks, efficiency of removal of photo-protecting groups, and the yields of the phosphoramidite coupling step. Further, unintended leakage of light into neighboring sites can be minimized. The density of synthesized oligomer per spot can be monitored by adjusting loading of the leader nucleoside on the surface of synthesis.

The surface of the substrate that provides support for oligonucleotide synthesis may be chemically modified to allow for the synthesized oligonucleotide chain to be cleaved from the surface. In some instances, the oligonucleotide chain is cleaved at the same time as the oligonucleotide is deprotected. In some cases, the oligonucleotide chain is cleaved after the oligonucleotide is deprotected. In an exemplary scheme, a trialkoxysilyl amine such as (CH3CH2O)3Si—(CH2)2-NH2 is reacted with surface SiOH groups of a substrate, followed by reaction with succinic anhydride with the amine to create an amide linkage and a free OH on which the nucleic acid chain growth is supported. Cleavage includes gas cleavage with ammonia or methylamine. In some instances, once released from the surface, oligonucleotides are assembled into larger nucleic acids that are sequenced and decoded to extract stored information.

Oligonucleotides may be designed to collectively span a large region of a predetermined sequence that encodes for information. In some instances, larger oligonucleotides are generated through ligation reactions to join the synthesized oligonucleotides. One example of a ligation reaction is polymerase chain assembly (PCA). In some instances, at least a portion of the oligonucleotides are designed to include an appended region that is a substrate for universal primer binding. For PCA reactions, the presynthesized oligonucleotides include overlaps with each other (e.g., 4, 20, 40 or more bases with overlapping sequence). During the polymerase cycles, the oligonucleotides anneal to complementary fragments and then are filled in by polymerase. Each cycle thus increases the length of various fragments randomly depending on which oligonucleotides find each other. Complementarity amongst the fragments allows for forming a complete large span of double-stranded DNA. In some cases, after the PCA reaction is complete, an error correction step is conducted using mismatch repair detecting enzymes to remove mismatches in the sequence. Once larger fragments of a target sequence are generated, they can be amplified. For example, in some cases, a target sequence comprising 5' and 3' terminal adapter sequences is amplified in a polymerase chain reaction (PCR) which includes modified primers that hybridize to the adapter sequences. In some cases, the modified primers comprise one or more uracil bases. The use of modified primers allows for removal of the primers through enzymatic reactions centered on targeting the modified base and/or gaps left by enzymes which cleave the modified base pair from the fragment. What remains is a double-stranded amplification product that lacks remnants of adapter sequence. In this way, multiple amplification products can be generated in parallel with the same set of primers to generate different fragments of double-stranded DNA.

Error correction may be performed on synthesized oligonucleotides and/or assembled products. An example strategy for error correction involves site-directed mutagenesis by overlap extension PCR to correct errors, which is optionally coupled with two or more rounds of cloning and sequencing. In certain instances, double-stranded nucleic acids with mismatches, bulges and small loops, chemically altered bases and/or other heteroduplexes are selectively removed from populations of correctly synthesized nucleic acids. In some instances, error correction is performed using proteins/enzymes that recognize and bind to or next to mismatched or unpaired bases within double-stranded nucleic acids to create a single or double-strand break or to initiate a strand transfer transposition event. Non-limiting examples of proteins/enzymes for error correction include endonucleases (T7 Endonuclease I, *E. coli* Endonuclease V, T4 Endonuclease VII, mung bean nuclease, Cell, *E. coli* Endonuclease IV, UVDE), restriction enzymes, glycosylases, ribonucleases, mismatch repair enzymes, resolvases, helicases, ligases, antibodies specific for mismatches, and their variants. Examples of specific error correction enzymes include T4 endonuclease 7, T7 endonuclease 1, S1, mung bean endonuclease, MutY, MutS, MutH, MutL, cleavase, CELI, and HINF1. In some cases, DNA mismatch-binding protein MutS (*Thermus aquaticus*) is used to remove failure products from a population of synthesized products. In some instances, error correction is performed using the enzyme Correctase. In some cases, error correction is performed using SURVEYOR endonuclease (Transgenomic), a mismatch-specific DNA endonuclease that scans for known and unknown mutations and polymorphisms for heteroduplex DNA.

Release, Extraction and Assembly

Provided herein are method and devices for replicable information storage. In some instances, multiple copies of the same coding region, the oligonucleotide, the same cluster, the same portion of a structure comprising oligonucleotides, or the entire structure comprising oligonucleotides are synthesized. Where multiple copies of the same oligonucleotide are synthesized, each of the oligonucleotides may be attached to distinct regions of the surface. The distinct regions may be separated by breaking or cutting. Alternatively, each of the oligonucleotides may be present at a feature in the form of a spot, well or channel and individually accessible. For example, contacting the feature with a cleavage reagent and then water would free one copy of the oligonucleotide while leaving the other copies intact. Similarly, cleavage of oligonucleotides in an entire region or over an entire plate allows for accessing a fraction of a replicate population. Replicate populations may exist in separated reels, plates, belts, and the like. In the case of a flexible material, such as a tape, a replicate region may be cut and the remaining regions of the tape may be spliced back together. Alternatively, nucleic acid information of the synthesized and stored oligonucleotides may be obtained by performing amplification of oligonucleotides attached to the surface of the structure using primers and a DNA polymerase.

In some instances, an aqueous or gaseous transfer media is deposited onto one or a plurality of channels in a structure to transfer the oligonucleotides from the structure to a receiving unit. For example, a transfer media may pass through a channel in the structure to adhere to, collect and transfer an oligonucleotide from a channel in the structure to a receiving unit. In some instances, a charge conducting feature and an applied voltage are employed to attract or repel a transfer media to or through a channel in the structure. In some instances, a slip is employed to direct a transfer media into a channel in the structure. In some cases a pressure release is employed to direct a transfer media into or through a channel in the structure. In some cases a nozzle is employed to form a localized area of high pressure which forces a transfer media into or through a channel in the structure. In some instances, a pin is employed to transfer an oligonucleotide from a channel in the structure to a container to a receiving unit. In such instances, the pin may comprise agents to facilitate transfer media adhesion. In some cases a charge conducting feature is employed to attract or repel a transfer media to or through a channel in a structure, by forming a voltage potential between the conducting feature and the structure. In some cases, a pipette tip, or other capillary flow inducing structure, is used to transfer the fluid and oligonucleotides via capillary flow. In some instances, a container comprises one or more compartments that each receives a portion of the transfer media, and the one or more oligonucleotides therein, emitted from a single respective channel. In some instances, the container comprises a single compartment that receives one or more portions of the transfer media, each containing one or more oligonucleotides therein, emitted from a one or more structure channels.

Sequencing

After extraction and/or amplification of oligonucleotides from the surface of the structure, suitable sequencing technology may be employed to sequence the oligonucleotides. In some cases, the DNA sequence is read on the substrate or within a feature of a structure. In some cases, the oligonucleotides stored on the substrate are extracted, optionally assembled into longer nucleic acids and then sequenced.

Oligonucleotides synthesized and stored on the structures described herein encode data that can be interpreted by reading the sequence of the synthesized oligonucleotides and converting the sequence into binary code readable by a computer. In some cases the sequences require assembly, and the assembly step may need to be at the nucleic acid sequence stage or at the digital sequence stage.

Provided herein are detection systems comprising a device capable of sequencing stored oligonucleotides, either directly on the structure and/or after removal from the main structure. In cases where the structure is a reel-to-reel tape of flexible material, the detection system comprises a device for holding and advancing the structure through a detection location and a detector disposed proximate the detection location for detecting a signal originated from a section of the tape when the section is at the detection location. In some instances, the signal is indicative of a presence of an oligonucleotide. In some instances, the signal is indicative of a sequence of an oligonucleotide (e.g., a fluorescent signal). In some instances, information encoded within oligonucleotides on a continuous tape is read by a computer as the tape is conveyed continuously through a detector operably connected to the computer. In some instances, a detection system comprises a computer system comprising an oligonucleotide sequencing device, a database for storage and retrieval of data relating to oligonucleotide sequence, software for converting DNA code of an oligonucleotide sequence to binary code, a computer for reading the binary code, or any combination thereof.

Computer Systems

In various aspects, any of the systems described herein are operably linked to a computer and are optionally automated through a computer either locally or remotely. In various instances, the methods and systems of the disclsoure further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the disclosure. In some instances, the computer systems are programmed to interface between the user specified base sequence and the position of a material deposition device to deliver the correct reagents to specified regions of the substrate.

Figure 17:
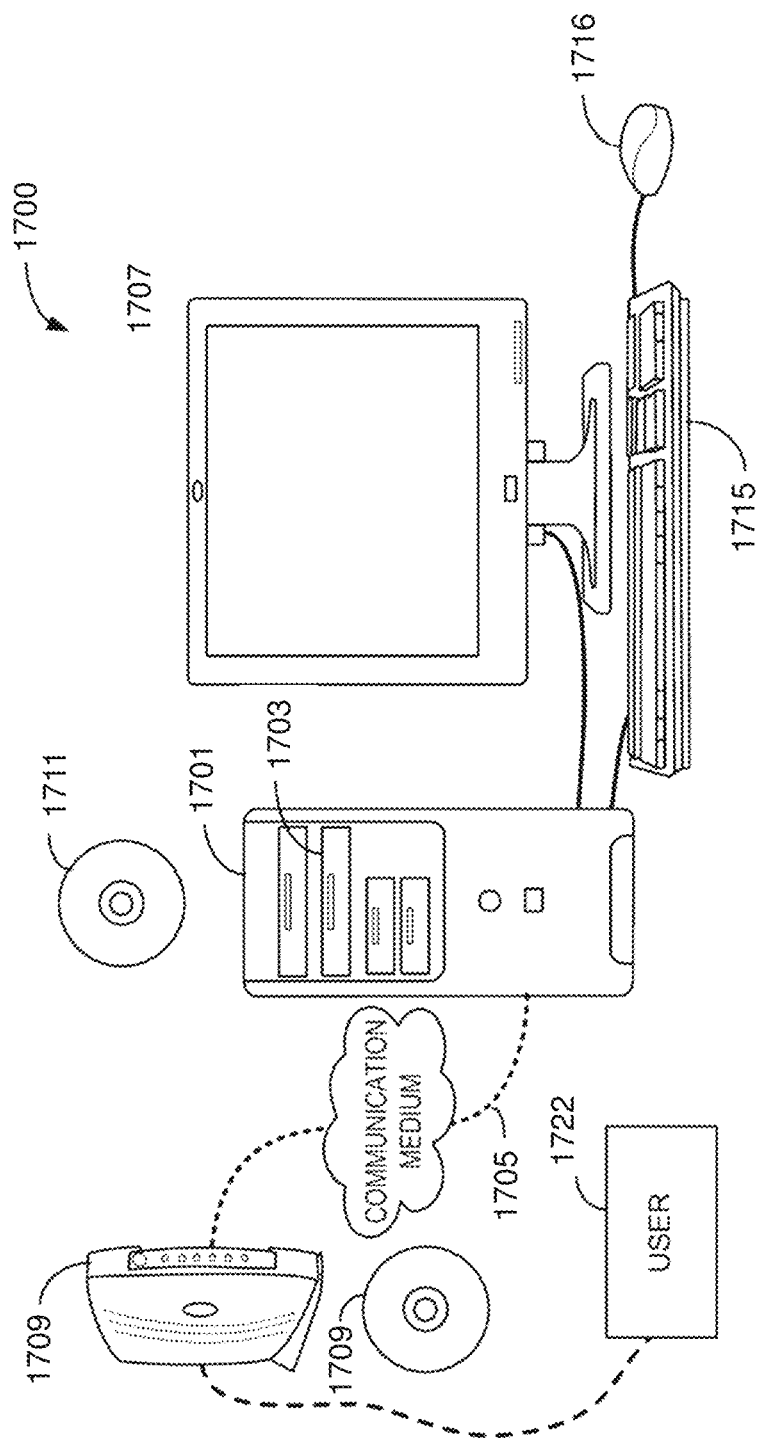
FIG. 17 illustrates an example of a computer system.

The computer system 1700 illustrated in FIG. 17 may be understood as a logical apparatus that can read instructions from media 1711 and/or a network port 1705, which can optionally be connected to server 1709 having fixed media 1712. The system, such as shown in FIG. 17 can include a CPU 1701, disk drives 1703, optional input devices such as keyboard 1715 and/or mouse 1716 and optional monitor 1707. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 1722.

Figure 18:
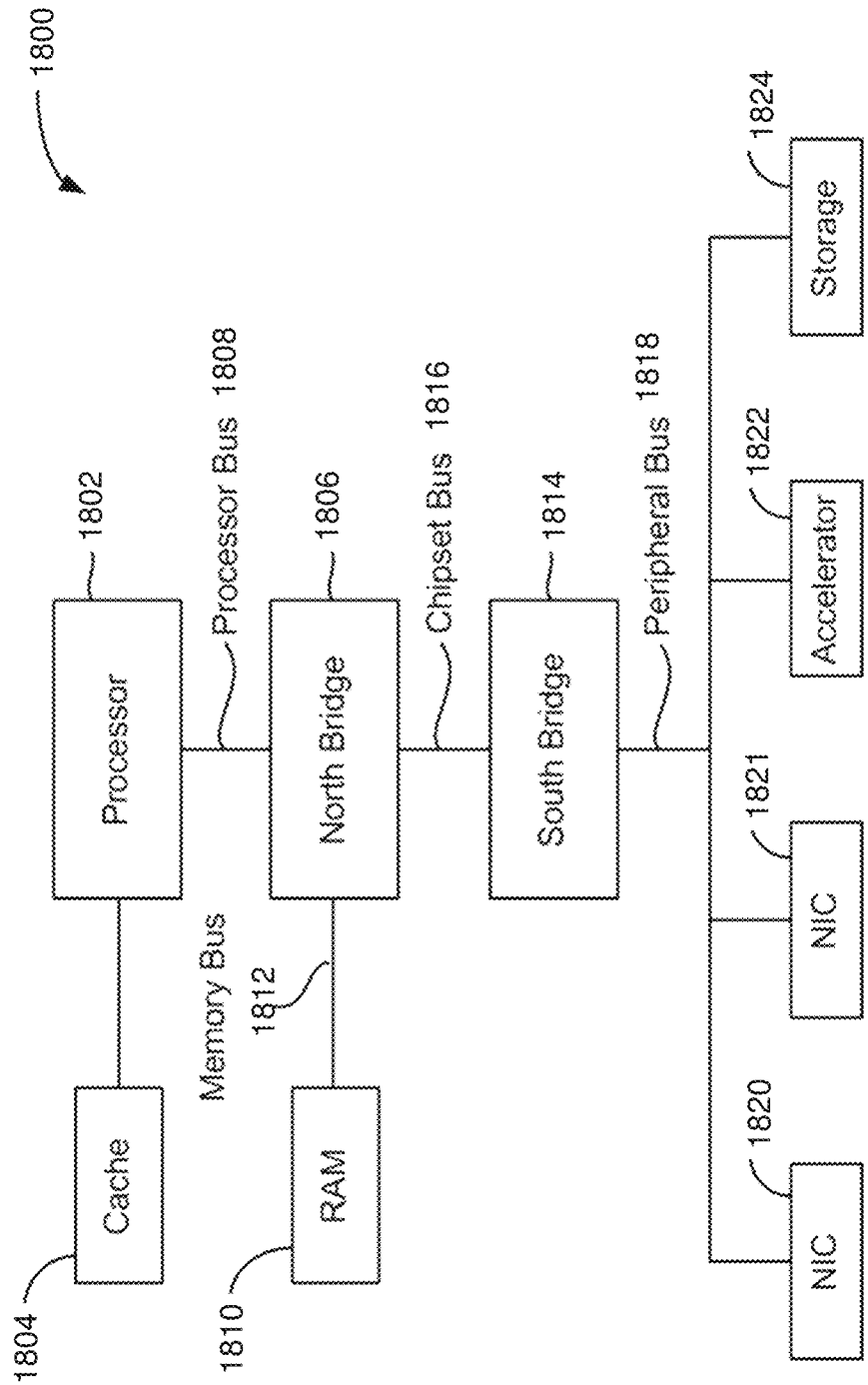
FIG. 18 is a block diagram illustrating architecture of a computer system.

FIG. 18 is a block diagram illustrating a first example architecture of a computer system 1800 that can be used in connection with example embodiments of the present disclosure. As depicted in FIG. 18, the example computer system can include a processor 1802 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices.

As illustrated in FIG. 18, a high speed cache 1804 can be connected to, or incorporated in, the processor 1802 to provide a high speed memory for instructions or data that have been recently, or are frequently, used by processor 1802. The processor 1802 is connected to a north bridge 1806 by a processor bus 1808. The north bridge 1806 is connected to random access memory (RAM) 1810 by a memory bus 1812 and manages access to the RAM 1810 by the processor 1802. The north bridge 1806 is also connected to a south bridge 1814 by a chipset bus 1816. The south bridge 1814 is, in turn, connected to a peripheral bus 1818. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 1818. In some alternative architectures, the functionality of the north bridge can be incorporated into the processor instead of using a separate north bridge chip.

In some instances, system 1800 can include an accelerator card 1822 attached to the peripheral bus 1818. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 1824 and can be loaded into RAM 1810 and/or cache 1804 for use by the processor. The system 1800 includes an operating system for managing system resources; non-limiting examples of operating systems include: Linux, Windows™, MACOS™, iOS™, and other functionally-equivalent operating systems, as well as application software running on top of the operating system for managing data storage and optimization in accordance with example embodiments of the present disclosure.

In this example, system 1800 also includes network interface cards (NICs) 1820 and 1821 connected to the peripheral bus for providing network interfaces to external storage, such as Network Attached Storage (NAS) and other computer systems that can be used for distributed parallel processing.

Figure 19:
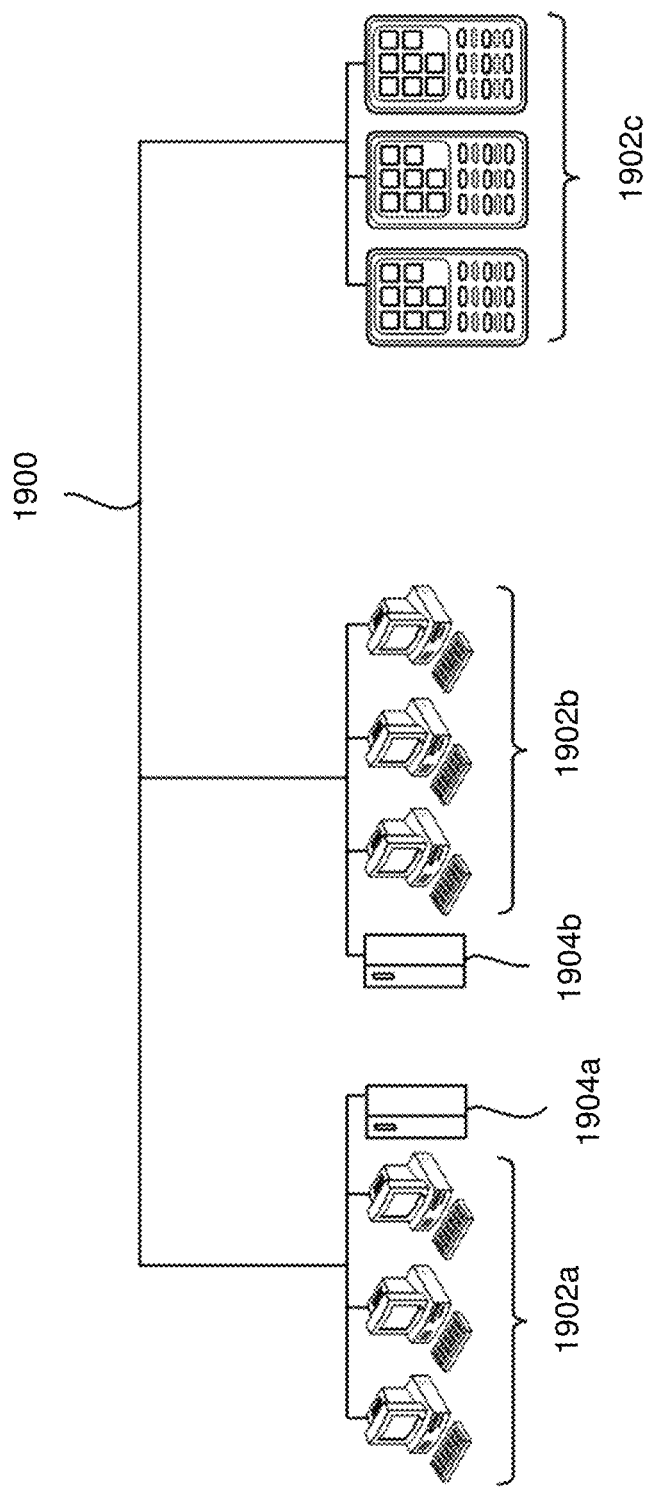
FIG. 19 is a diagram demonstrating a network configured to incorporate a plurality of computer systems, a plurality of cell phones and personal data assistants, and Network Attached Storage (NAS).

FIG. 19 is a diagram showing a network 1900 with a plurality of computer systems 1902a, and 1902b, a plurality of cell phones and personal data assistants 1902c, and Network Attached Storage (NAS) 1904a, and 1904b. In example embodiments, systems 1902a, 1902b, and 1902c can manage data storage and optimize data access for data stored in Network Attached Storage (NAS) 1904a and 1904b. A mathematical model can be used for the data and be evaluated using distributed parallel processing across computer systems 1902a, and 1902b, and cell phone and personal data assistant systems 1902c. Computer systems 1902a, and 1902b, and cell phone and personal data assistant systems 1902c can also provide parallel processing for adaptive data restructuring of the data stored in Network Attached Storage (NAS) 1904a and 1904b. FIG. 19 illustrates an example only, and a wide variety of other computer architectures and systems can be used in conjunction with the various embodiments of the present disclosure. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other instances, some or all of the processors can use a shared virtual address memory space.

Figure 20:
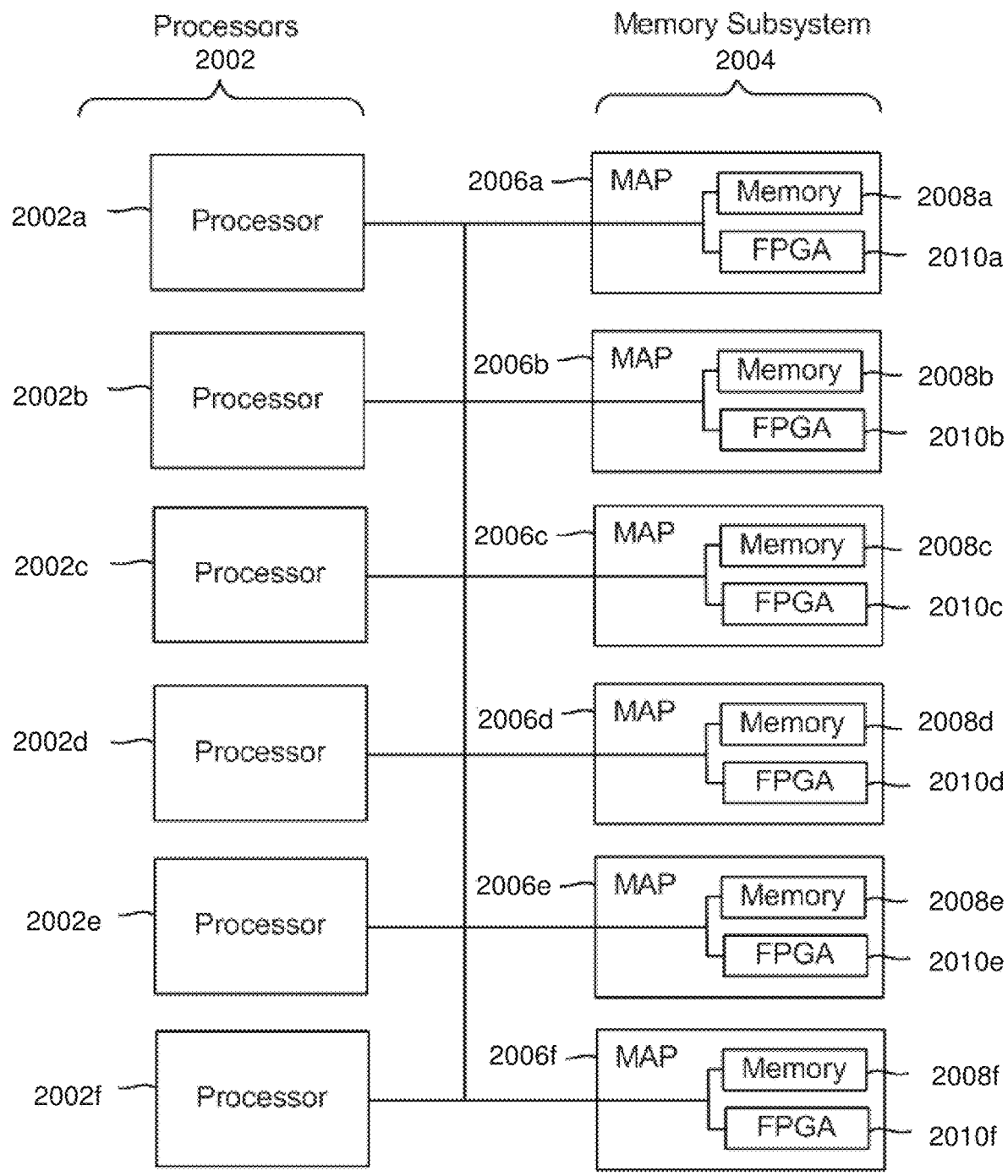
FIG. 20 is a block diagram of a multiprocessor computer system using a shared virtual address memory space.

FIG. 20 is a block diagram of a multiprocessor computer system 2000 using a shared virtual address memory space in accordance with an example embodiment. The system includes a plurality of processors 2002a-f that can access a shared memory subsystem 2004. The system incorporates a plurality of programmable hardware memory algorithm processors (MAPs) 2006a-f in the memory subsystem 2004. Each MAP 2006a-f can comprise a memory 2008a-f and one or more field programmable gate arrays (FPGAs) 2010a-f. The MAP provides a configurable functional unit and particular algorithms or portions of algorithms can be provided to the FPGAs 2010a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 2008a-f, allowing it to execute tasks independently of, and asynchronously from, the respective microprocessor 2002a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example instances, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other instances, the functions of the system can be implemented partially or completely in firmware, programmable logic devices such as field programmable gate arrays (FPGAs), system on chips (SOCs), application specific integrated circuits (ASICs), or other processing and logic elements. For example, the Set Processor and Optimizer can be implemented with hardware acceleration through the use of a hardware accelerator card, such as an accelerator card.

Provided herein are methods for storing information, comprising: converting an item of information in the form of at least one digital sequence to at least one nucleic acid sequence; providing a flexible structure having a surface; synthesizing a plurality of oligonucleotides having predetermined sequences collectively encoding for the at least one nucleic acid sequence, wherein the plurality of oligonucleotides comprises at least about 100,000 oligonucleotides, and wherein the plurality of oligonucleotides extends from the surface of the flexible structure; and storing the plurality of oligonucleotides. Further provided herein are methods wherein synthesizing comprises: depositing nucleosides on the surface at predetermined locations; and moving at least a portion of the flexible structure through a bath or emissions from a spray bar. Further provided herein are methods wherein the bath or emissions from a spray bar expose the surface of the structure to an oxidizing reagent or a deblocking reagent. Further provided herein are methods wherein synthesizing further comprises capping the nucleosides deposited on the surface. Further provided herein are methods wherein the nucleosides comprise a nucleoside phosphoramidite. Further provided herein are methods wherein the flexible structure comprises a reel-to-reel tape or a continuous tape. Further provided herein are methods wherein the flexible structure comprises a thermoplastic material. Further provided herein are methods wherein the thermoplastic material comprises a polyaryletherketone. Further provided herein are methods wherein the polyaryletherketone is polyetherketone, polyetherketoneketone, poly(ether ether ketone ketone), polyether ether ketone or polyetherketoneetherketoneketone. Further provided herein are methods wherein the flexible structure comprises nylon, nitrocellulose, polypropylene, polycarbonate, polyethylene, polyurethane, polystyrene, acetal, acrylic, acrylonitrile, butadiene styrene, polyethylene terephthalate, polymethyl methacrylate, polyvinyl chloride, transparent PVC foil, Poly (methyl methacrylate), styrenic polymer, fluorine-containing polymers, polyethersulfone or polyimide. Further provided herein are methods wherein each oligonucleotide of the plurality of oligonucleotides comprises from 50 to 500 bases in length. Further provided herein are methods wherein the plurality of oligonucleotides comprises at least about 10 billion oligonucleotides. Further provided herein are methods wherein at least about $1.75 \times 10^{13}$ nucleobases are synthesized within 24 hours. Further provided herein are methods wherein at least about $262.5 \times 10^{9}$ oligonucleotides are synthesized within 72 hours. Further provided herein are methods wherein the item of information is text information, audio information or visual information. Further provided herein are methods wherein the nucleosides comprise nucleoside phosphoramidite.

Provided herein are methods for storing information, comprising: converting an item of information in the form of at least one digital sequence to at least one nucleic acid sequence; providing a structure having a surface; synthesizing a plurality of oligonucleotides having predetermined sequences collectively encoding for the at least one nucleic acid sequence, wherein the plurality of oligonucleotides comprises at least about 100,000 oligonucleotides, wherein the plurality of oligonucleotides extends from the surface of the structure, and wherein synthesizing comprises: cleaning a surface of the structure; depositing nucleosides on the surface at predetermined locations; oxidizing, deblocking, and optionally capping the nucleosides deposited on the surface; wherein the cleaning, oxidizing, deblocking, and capping comprises moving at least a portion of the flexible structure through a bath or emissions from a spray bar; and storing the plurality of oligonucleotides. Further provided herein are methods wherein the nucleosides comprise nucleoside phosphoramidite.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

Example 1

Functionalization of a Device Surface

A device was functionalized to support the attachment and synthesis of a library of oligonucleotides. The device surface was first wet cleaned using a piranha solution comprising 90% $H_2SO_4$ and 10% $H_2O_2$ for 20 minutes. The device was rinsed in several beakers with DI water, held under a DI water gooseneck faucet for 5 min, and dried with $N_2$. The device was subsequently soaked in $NH_4OH$ (1:100; 3 mL:300 mL) for 5 min, rinsed with DI water using a handgun, soaked in three successive beakers with DI water for 1 min each, and then rinsed again with DI water using the handgun. The device was then plasma cleaned by exposing the device surface to $O_2$. A SAMCO PC-300 instrument was used to plasma etch $O_2$ at 250 watts for 1 min in downstream mode.

The cleaned device surface was actively functionalized with a solution comprising N-(3-triethoxysilylpropyl)-4-hydroxybutyramide using a YES-1224P vapor deposition oven system with the following parameters: 0.5 to 1 torr, 60 min, 70° C., 135° C. vaporizer. The device surface was resist coated using a Brewer Science 200× spin coater. SPR™ 3612 photoresist was spin coated on the device at 2500 rpm for 40 sec. The device was pre-baked for 30 min at 90° C. on a Brewer hot plate. The device was subjected to photolithography using a Karl Suss MA6 mask aligner instrument. The device was exposed for 2.2 sec and developed for 1 min in MSF 26A. Remaining developer was rinsed with the handgun and the device soaked in water for 5 min. The device was baked for 30 min at 100° C. in the oven, followed by visual inspection for lithography defects using a Nikon L200. A descum process was used to remove residual resist using the SAMCO PC-300 instrument to $O_2$ plasma etch at 250 watts for 1 min.

The device surface was passively functionalized with a 100 μL solution of perfluorooctyltrichlorosilane mixed with 10 μL light mineral oil. The device was placed in a chamber, pumped for 10 min, and then the valve was closed to the pump and left to stand for 10 min. The chamber was vented to air. The device was resist stripped by performing two soaks for 5 min in 500 mL NMP at 70° C. with ultrasonication at maximum power (9 on Crest system). The device was then soaked for 5 min in 500 mL isopropanol at room temperature with ultrasonication at maximum power. The device was dipped in 300 mL of 200 proof ethanol and blown dry with $N_2$. The functionalized surface was activated to serve as a support for oligonucleotide synthesis.

Example 2

Synthesis of a 50-mer Sequence on an Oligonucleotide Synthesis Device

A two dimensional oligonucleotide synthesis device was assembled into a flowcell, which was connected to a flowcell (Applied Biosystems (ABI394 DNA Synthesizer"). The two-dimensional oligonucleotide synthesis device was uniformly functionalized with N-(3-TRIETHOXYSILYLPRO-PYL)-4-HYDROXYBUTYRAMIDE (Gelest) and used to synthesize an exemplary oligonucleotide of 50 bp ("50-mer oligonucleotide") using oligonucleotide synthesis methods described herein.

The sequence of the 50-mer was as described in SEQ ID NO.: 1. 5'AGACAATCAACCAT-TTGGGGTGGACAGCCTTGA CCTCTAGACTTCGGCAT##TTTTT TTTTT3' (SEQ ID NO.: 1), where # denotes Thymidine-succinyl hexamide CED phosphoramidite (CLP-2244 from ChemGenes), which is a cleavable linker enabling the release of oligonucleotides from the surface during deprotection.

The synthesis was done using standard DNA synthesis chemistry (coupling, capping, oxidation, and deblocking) according to the protocol in Table 5 and an ABI synthesizer.

TABLE 5

Synthesis Protocol

General DNA Synthesis — Table 5

| Process Name | Process Step | Time (sec) |
|---|---|---|
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Activator to Flowcell | 0.5 |
| | Activator + | 5 |

TABLE 5-continued

Synthesis Protocol

General DNA Synthesis — Table 5

| Process Name | Process Step | Time (sec) |
|---|---|---|
| | Phosphoramidite to Flowcell | |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the ABI 394 synthesizer to enable faster flow. Without flow restrictor, flow rates for amidites (0.1M in ACN), Activator, (0.25M Benzoylthiotetrazole ("BTT"; 30-3070-xx from GlenResearch) in ACN), and Ox (0.02M I2 in 20% pyridine, 10% water, and 70% THF) were roughly ~100 uL/sec, for acetonitrile ("ACN") and capping reagents (1:1 mix of CapA and CapB, wherein CapA is acetic anhydride in THF/Pyridine and CapB is 16% 1-methylimidizole in THF), roughly ~200 uL/sec, and for Deblock (3% dichloroacetic acid in toluene), roughly ~300 uL/sec (compared to ~50 uL/sec for all reagents with flow restrictor). The time to completely push out Oxidizer was observed, the timing for chemical flow times was adjusted accordingly and an extra ACN wash was introduced between different chemicals. After oligonucleotide synthesis, the chip was deprotected in gaseous ammonia overnight at 75 psi. Five drops of water were applied to the surface to assemble oligonucleotides.

The assembled oligonucleotides were then analyzed on a BioAnalyzer small RNA chip (data not shown).

Example 3

Synthesis of a 100-mer Sequence on an Oligonucleotide Synthesis Device

The same process as described in Example 2 for the synthesis of the 50-mer sequence was used for the synthesis of a 100-mer oligonucleotide ("100-mer oligonucleotide"; 5' CGGGATCCTTATCGTCATCGTCGTACA-GATCCCGACCCATTTGCTGTCCACCAGTCAT GCTAGCCATACCATGATGATGATGATGAGAAC CCCGCAT##TTTTTTTTTT3', where # denotes Thymidine-succinyl hexamide CED phosphoramidite (CLP-2244 from ChemGenes); SEQ ID NO.: 2) on two different silicon chips, the first one uniformly functionalized with N-(3-TRIETHOXYSILYLPROPYL)-4-HYDROXYBUTYR-AMIDE and the second one functionalized with 5/95 mix of 11-acetoxyundecyltriethoxysilane and n-decyltriethoxysilane, and the oligonucleotides extracted from the surface were analyzed on a BioAnalyzer instrument (data not shown).

All ten samples from the two chips were further PCR amplified using a forward (5'ATGCGGGGTTCTCAT-CATC3'; SEQ ID NO.: 3) and a reverse (5'CGGGATCCT-TATCGTCATCG3'; SEQ ID NO.: 4) primer in a 50 uL PCR mix (25 uL NEB Q5 mastermix, 2.5 uL 10 uM Forward primer, 2.5 uL 10 uM Reverse primer, 1 uL oligonucleotide extracted from the surface, and water up to 50 uL) using the following thermalcycling program:

98° C., 30 sec
98° C., 10 sec; 63° C., 10 sec; 72° C., 10 sec; repeat 12 cycles 72° C., 2 min The PCR products were also run on a BioAnalyzer (data not shown), demonstrating sharp peaks at the 100-mer position. Next, the PCR amplified samples were cloned, and Sanger sequenced. Table 6 summarizes the results from the Sanger sequencing for samples taken from spots 1-5 from chip 1 and for samples taken from spots 6-10 from chip 2.

TABLE 6

| \multicolumn{3}{c}{Sequencing Results} | | |
|---|---|---|
| Spot | Error rate | Cycle efficiency |
| 1 | 1/763 bp | 99.87% |
| 2 | 1/824 bp | 99.88% |
| 3 | 1/780 bp | 99.87% |
| 4 | 1/429 bp | 99.77% |
| 5 | 1/1525 bp | 99.93% |
| 6 | 1/1615 bp | 99.94% |
| 7 | 1/531 bp | 99.81% |
| 8 | 1/1769 bp | 99.94% |
| 9 | 1/854 bp | 99.88% |
| 10 | 1/1451 bp | 99.93% |

Thus, the high quality and uniformity of the synthesized oligonucleotides were repeated on two chips with different surface chemistries. Overall, 89%, corresponding to 233 out of 262 of the 100-mers that were sequenced were perfect sequences with no errors.

Table 7 summarizes error characteristics for the sequences obtained from the oligonucleotides samples from spots 1-10.

TABLE 7

| Error Characteristics | | | | | |
|---|---|---|---|---|---|
| | Sample ID/Spot no. | | | | |
| | OSA_0046/1 | OSA_0047/2 | OSA_0048/3 | OSA_0049/4 | OSA_0050/5 |
| Total Sequences | 32 | 32 | 32 | 32 | 32 |
| Sequencing Quality | 25 of 28 | 27 of 27 | 26 of 30 | 21 of 23 | 25 of 26 |
| Oligo Quality | 23 of 25 | 25 of 27 | 22 of 26 | 18 of 21 | 24 of 25 |
| ROI Match Count | 2500 | 2698 | 2561 | 2122 | 2499 |
| ROI Mutation | 2 | 2 | 1 | 3 | 1 |
| ROI Multi Base Deletion | 0 | 0 | 0 | 0 | 0 |
| ROI Small Insertion | 1 | 0 | 0 | 0 | 0 |
| ROI Single Base Deletion | 0 | 0 | 0 | 0 | 0 |
| Large Deletion Count | 0 | 0 | 1 | 0 | 0 |
| Mutation: G > A | 2 | 2 | 1 | 2 | 1 |
| Mutation: T > C | 0 | 0 | 0 | 1 | 0 |
| ROI Error Count | 3 | 2 | 2 | 3 | 1 |
| ROI Error Rate | Err: ~1 in 834 | Err: ~1 in 1350 | Err: ~1 in 1282 | Err: ~1 in 708 | Err: ~1 in 2500 |

TABLE 7-continued

| | | | Error Characteristics | | |
|---|---|---|---|---|---|
| ROI Minus Primer Error Rate | MP Err: ~1 in 763 | MP Err: ~1 in 824 | MP Err: ~1 in 780 | MP Err: ~1 in 429 | MP Err: ~1 in 1525 |

| | Sample ID/Spot no. | | | | |
|---|---|---|---|---|---|
| | OSA_0051/6 | OSA_0052/7 | OSA_0053/8 | OSA_0054/9 | OSA_0055/10 |
| Total Sequences | 32 | 32 | 32 | 32 | 32 |
| Sequencing Quality | 29 of 30 | 27 of 31 | 29 of 31 | 28 of 29 | 25 of 28 |
| Oligo Quality | 25 of 29 | 22 of 27 | 28 of 29 | 26 of 28 | 20 of 25 |
| ROI Match Count | 2666 | 2625 | 2899 | 2798 | 2348 |
| ROI Mutation | 0 | 2 | 1 | 2 | 1 |
| ROI Multi Base Deletion | 0 | 0 | 0 | 0 | 0 |
| ROI Small Insertion | 0 | 0 | 0 | 0 | 0 |
| ROI Single Base Deletion | 0 | 0 | 0 | 0 | 0 |
| Large Deletion Count | 1 | 1 | 0 | 0 | 0 |
| Mutation: G > A | 0 | 2 | 1 | 2 | 1 |
| Mutation: T > C | 0 | 0 | 0 | 0 | 0 |
| ROI Error Count | 1 | 3 | 1 | 2 | 1 |
| ROI Error Rate | Err: ~1 in 2667 | Err: ~1 in 876 | Err: ~1 in 2900 | Err: ~1 in 1400 | Err: ~1 in 2349 |
| ROI Minus Primer Error Rate | MP Err: ~1 in 1615 | MP Err: ~1 in 531 | MP Err: ~1 in 1769 | MP Err: ~1 in 854 | MP Err: ~1 in 1451 |

Example 4

Highly Accurate DNA-based Information Storage and Assembly

Digital information was selected in the form of binary data totaling about 0.2 GB included content for the Universal Declaration of Human Rights in more than 100 languages, the top 100 books of Project Guttenberg and a seed database. The digital information was encrypted into a nucleic acid-based sequence and divided into strings. Over 10 million non-identical oligonucleotides, each corresponding to a string, were synthesized on a rigid silicon surface in a manner similar to that described in Example 2. Each non-identical oligonucleotide was under equal or less than 200 bases in length. The synthesized oligonucleotides were collected and sequenced and decoded back to digital code, with 100% accuracy for the source digital information, compared to the initial at least one digital sequence.

Example 5

Conversion of Digital Information to Nucleic Acid Sequence

A computer txt file includes text information. A general purpose computer uses a software program having machine instructions for conversion of the sequence to base 3, 4, or 5 sequence, depending on instructions received. Each number in base 3 is assigned a nucleic acid (e.g., A=0, T=1, C=2). Each number in base 4 is assigned a nucleic acid (e.g., A=0, T=1, C=2, G=3). Alternatively, a base 5 quinary sequence is used, where each number in base 5 is assigned a nucleic acid (e.g., A=0, T=1, C=2, G=3, U=4). A sequence is generated as depicted in Table 8. Machine instructions are then provided for de novo synthesis of oligonucleotides encoding the nucleic acid sequence.

TABLE 8

| Sequence Conversion | |
|---|---|
| Text | Jack went up the hill. |
| Binary sequence | 01001010011000010110001101101011001000000111011101100101011011100011101000010000001110101011100000001000000111010001101000011001 |

TABLE 8-continued

Sequence Conversion

| | |
|---|---|
| Text | Jack went up the hill. |
| | 0100100000011010000110100101101100011011000010111000001101000010100000110100001010 |
| Ternary sequence | 10101020110002210101002110201222120010111220221000212200221020001111221210201120102111212220010111000100200102200222221100222 22112 |
| Quaternary sequence | 1022120112031223020013131211123213100200131113000200131012201211020012201221123012300232003100220031002231 |
| Quinary sequence | 332214330133012303013123001030244433343300431224103020320210201 12342341100431241100334213 |

Example 6

Flexible Surface Having a High Density of Features

Figure 14A:
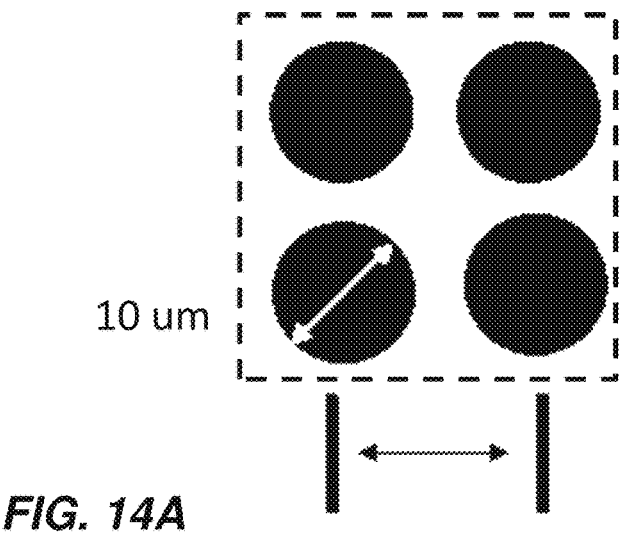
FIG. 14A illustrates a zoom in of features on a structure described herein.
Figure 14B:
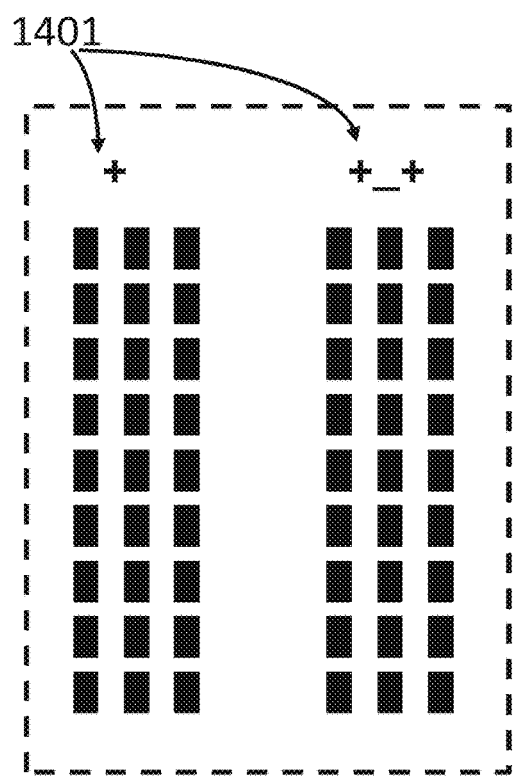
FIGS. 14B-14C illustrate markings on structures described herein.
Figure 14C:
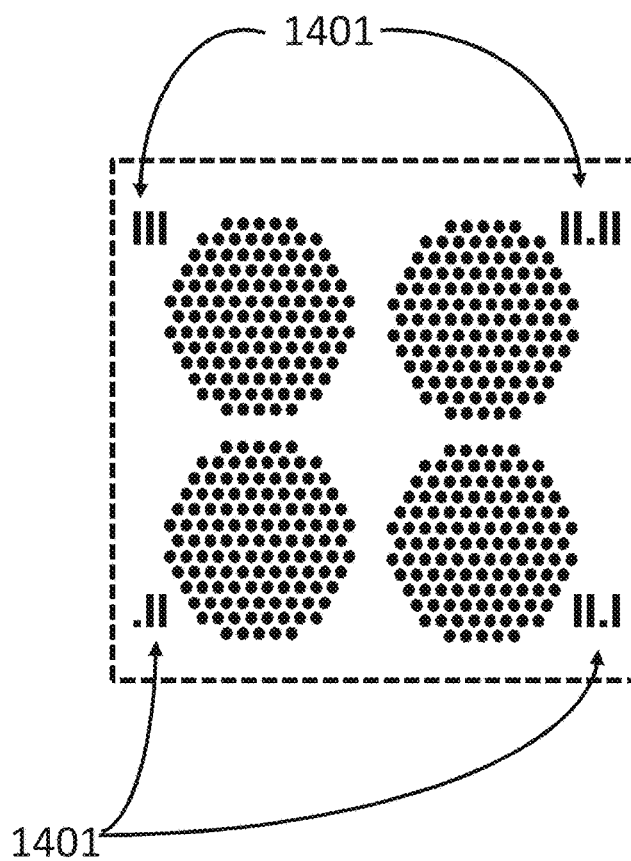

A flexible structure comprising thermoplastic material is coated with a nucleoside coupling reagent. The coating agent is patterned for a high density of features. A portion of the flexible surface is illustrated in FIG. 14A. Each feature has a diameter of 10 um, with a center-to-center distance between two adjacent features of 21 um. The feature size is sufficient to accommodate a sessile drop volume of 0.2 pl during an oligonucleotide synthesis deposition step. The small feature dimensions allow for a high density of oligonucleotides to be synthesized on the surface of the substrate. The feature density is 2.2 billion features /m$^2$ (1 feature/ $441 \times 10^{-12}$ m$^2$). A 4.5 m$^2$ substrate is manufactured having 10 billion features, each with a 10 um diameter. The flexible structure is optionally placed in a continuous loop system, FIG. 12A, or a reel-to-reel system, FIG. 12B, for oligonucleotide synthesis.

Example 7

Oligonucleotide Synthesis on a Flexible Structure

A flexible structure is prepared comprising a plurality of features on a thermoplastic flexible material. The structure serves as a support for the synthesis of oligonucleotides using an oligonucleotide synthesis device comprising a deposition device. The flexible structure is in the form of a flexible media much like a magnetic reel-to-reel tape.

De novo synthesis operates in a continuous production line manner with the structure travelling through a solvent bath and then beneath a stack of printheads where the phosphoramidites are printed on to a surface of the structure. The flexible structure with the sessile drops deposited on to the surface is rolled into a bath of oxidizing agent, then the tape emerges from the oxidizing bath and is immersed in an acetonitrile wash bath then submerged in a deblock bath. Optionally, the tape is traversed through a capping bath. In an alternative workflow, the flexible structure emerges from the oxidizing bath and is sprayed with acetonitrile in a wash step.

Alternatively, a spray bar is used instead of a liquid bath. In this process, the nucleotides are still deposited on the surface with an inkjet device but the flood steps are now done in a chamber with spray nozzles. For example, the deposition device has 2,048 nozzles that each deposits 100,000 droplets per second at 1 nucleobase per droplet. There is a sequential ordering of spray nozzles to mimic the ordering of the flood steps in standard phosphoramidite chemistry. This technique provides for easily changing the chemicals loaded in the spray bar to accommodate different process steps. Oligonucleotides are deprotected or cleaved in the same manner as described in Example 2.

For each deposition device, more than $1.75 \times 10^{13}$ nucleobases are deposited on the structure per day. A plurality of 200 nucleobase oligonucleotides is synthesized. In 3 days, at a rate of $1.75 \times 10^{13}$ bases per day, $262.5 \times 10^9$ oligonucleotides are synthesized.

Example 8

Selection Bioencryption

Machine instructions are received for desired items of information for conversion and for one or more categories of bioencryption selected from enzymatic based (e.g., CRISPR/Cas complex and restriction enzyme digest), electromagnetic radiation based (e.g., photolysis and photodetection), chemical cleavage (e.g, gaseous ammonia or methylamine treatment to cleave Thymidine-succinyl hexamide CED phosphoramidite (CLP-2244 from ChemGenes)), and affinity based (e.g., a sequence tag for hybridization, or incorporation of modified nucleotides with enhanced affinity to a capture reagent) forms of bioencryption. Following receipt of a particular bioencryption selection, a program module performs the step of converting the items of information to nucleic acid sequences and applying design instructions for design of a bioencrypted version of the sequence. A specific encryption subtype within the bioencryption category is selected. Synthesis instructions are then provided to a material deposition device for de novo synthesis of oligonucleotides.

Example 9

Selected Biodecryrption

Machine instructions are provided for application of one or more categories of biodecryption selected from enzymatic based (e.g., CRISPR/Cas complex or restriction enzyme digest), electromagnetic radiation based (e.g., photolysis or photodetection), chemical cleavage based (e.g, gaseous ammonia or methylamine treatment to cleave Thymidine-succinyl hexamide CED phosphoramidite (CLP-2244 from ChemGenes)), and affinity based (e.g., a sequence tag for hybridization, or incorporation of modified nucleotides with enhanced affinity to a capture reagent) biodecryption. Following receipt of a particular biodecryption selection, a program module performs the step of releasing the modulatory agent(s) for enrichment of the oligonucleotides. Following enrichment, the oligonucleotides are sequenced,

Example 10

Biological Encryption and Decryption of a DNA Ssequence with CRISPR/Cas9

A digital sequence encoding for an item of information is received. The digital sequence is then converted to a nucleic acid sequence. The nucleic acid sequence is encrypted in a larger population of nucleic acid sequences. The encryption process involves adding "junk" regions for detection and removal by a CRISPR/Cas9 complex. Nucleic acid sequences are synthesized as in Examples 2-3.

The population of nucleic acid sequences comprising the encrypted nucleic acid sequences are mixed with Cas9 and gRNAs in Cas9 buffer and incubated at 37° C. for 2 hours. Cas9 is then inactivated and removed by purification. The purified sample is then analyzed by next generation sequencing.

Example 11

Biological Encryption and Decryption of a DNA Sequence with CRISPR/Cas9 Comprising Sequence Swapping A digital sequence encoding for an item of information is received, the digital sequence is converted to nucleic acid sequences. The nucleic acid sequences are encrypted by addition of a specific sequence using CRISPR/Cas9 system and guide RNA sequence. Nucleic acid sequences are synthesized as in Examples 2-3.

The nucleic acid sequences are then mixed with fluorescent-tagged probes that are complementary to the swapped sequences. Nucleic acid sequences identified by the fluorescent-tagged probes are removed from the population.

Example 12

Biological Encryption and Decryption of a DNA Sequence Using Restriction Enzyme Digest A digital sequence encoding for an item of information is received, and the digital sequence is converted to nucleic acid sequences. A population of nucleic acid sequences is encrypted by addition of a specific sequence that is recognized by the restriction enzyme EcoRI. Nucleic acid sequences are synthesized, as in Examples 2-3, and stored.

The nucleic acid sequences are incubated with EcoRI. Encrypted nucleic acid sequences comprising the EcoRI recognition site are cleaved. Following cleavage of the encrypted nucleic acid sequences, sequences with complementary overhangs are hybridized and ligated to the released DNA. The ligated complex is then isolated and the purified sample is sequenced and the original digital information is assembled.

Example 13

Biological Encryption and Decryption of a DNA Sequence Using Photolysis

A digital sequence encoding for an item of information is received, and the digital sequence is converted to nucleic acid sequences. A population of nucleic acid sequences is designed to include nucleobases that are photocleavable. Nucleic acid sequences are synthesized as in Examples 2-3, and stored.

UV-B irradiation of 280 nm is applied to the nucleic acid sequences. Encrypted nucleic acid sequences comprising the photocleavable site are cleaved and removed. The nucleic acid sequences are then collected sequenced. Alternatively, nucleic acid sequences are released from the surface of a structure, such as by ammonia gas cleavage, and then exposed to electromagnetic radiation to provide for breaks in the nucleotide sequences. Portions of the population are enriched, such as by pull down assay using beads having complementary capture probes bound thereto, PCR using primers selected to only amplify target sequence, or size exclusion chromatography. Enriched nucleic acids are then sequenced, converted to digital sequence, and an item of information is received.

Example 14

Biological Encryption and Decryption of a DNA Sequence Using Chemical Enrichment A digital sequence encoding for an item of information is received, and the digital sequence is converted to nucleic acid sequences. A population of nucleic acid sequences is encrypted by addition of a specific sequence (e.g., Thymidine-succinyl hexamide CED phosphoramidite (CLP-2244 from ChemGenes)) that is chemically cleavable by ammonia gas. Nucleic acid sequences are synthesized as in Examples 2-3.

Ammonia gas is applied to the nucleic acid sequences. Encrypted nucleic acid sequences comprising the chemically cleavable sequence are released and enriched from the population using enrichment methods described herein. Enriched nucleic acids are then sequenced, converted to digital sequence, and an item of information is received.

Example 15

Biological Encryption and Decryption of a DNA Sequence Using Nucleic Acid Probes Comprising Biotin A digital sequence encoding for an item of information is received, and the digital sequence is converted to nucleic acid sequences. A population of nucleic acid sequences is encrypted by design of predetermined residues to comprise biotin containing nucleobases. Nucleic acid sequences are synthesized as in Examples 2-3.

The nucleic acid sequences are cleaved from a structure, and mixed with streptavidin containing beads. The nucleic acid sequences are then incubated with streptavidin magnetic beads. Nucleic acid sequences comprising biotin are pulled down by the magnetic beads. Enriched nucleic acids are then sequenced, converted to digital sequence, and an item of information is received.

Example 16

Biological Encryption and Decryption of a DNA Sequence Using Photodetection A digital sequence encoding for an item of information is received, and the digital sequence is converted to nucleic acid sequences. A population of nucleic acid sequences is encrypted by design to include specific sequence that is recognized by Alexa488-tagged nucleic acid probes. Nucleic acid sequences are synthesized as in Examples 2-3.

The nucleic acid sequences are released from a structure and mixed with Alexa488-tagged nucleic acid probes. The nucleic acid sequences are then sorted by fluorescence intensity. Nucleic acid sequences that are tagged with Alexa488-tagged nucleic acid probes are further analyzed. Probe bound nucleic acids are then sequenced, converted to digital sequence, and an item of information is received.

Example 17

Biological Encryption and Decryption of a DNA Sequence Using Modified Nucleotides A digital sequence encoding for an item of information is received, the digital sequence is converted to nucleic acid sequences. A population of nucleic acid sequences is encrypted by designing for the addition of predetermined nucleobases comprising peptide nucleic acid (PNA) at predetermined locations and for the design of restriction enzyme recognitions sizes to excise PNA containing sections. Nucleic acid sequences are synthesized as in Examples 2-3.

The nucleic acid sequences are released, subject to restriction enzyme digestion, and then amplified by PCR. Nucleic acid sequences comprising PNAs are unable to be amplified. Enriched, amplified nucleic acids are then sequenced, converted to digital sequence, and the item of information is received.

Example 18

Biological Encryption and Decryption of a DNA Sequence Using CRISPR/Cas9 and Chemical Cleavage A digital sequence encoding for an item of information is received, the digital sequence is converted to nucleic acid sequences. A population of nucleic acid sequences is encrypted by addition of a specific sequence using CRISPR/Cas9 and guide RNA sequence. The CRISPR/Cas9 system introduces a chemically cleavable site in the nucleic acid sequences at preselected locations. Nucleic acid sequences are synthesized as in Examples 2-3.

Ammonia gas is applied to the nucleic acid sequences. Encrypted nucleic acid sequences comprising the chemically cleavable site are cleaved and removed by size exclusion purification and analyzed by next generation sequencing.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for storing information, the method comprising:
   a) receiving, by a computing system, at least one item of information in a form of at least one digital sequence;
   b) receiving, by the computing system, instructions for enzymatic bioencryption;
   c) converting, by the computing system, the at least one digital sequence to digital sequences of a plurality of oligonucleotides based on the instructions, wherein the digital sequences of the plurality of oligonucleotides are configured for decryption by exposure of the plurality of oligonucleotides to a nuclease complex;
   d) synthesizing the plurality of oligonucleotides in a synthesizer; and
   e) storing the plurality of oligonucleotides.

2. The method of claim 1, wherein the enzymatic bioencryption comprises CRISPR/Cas-based bioencryption.

3. The method of claim 1, wherein the nuclease complex comprises an enzyme as set out in Table 1:

| Recognition Sequence | Enzyme |
|---|---|
| AA/CGTT | AclI |
| A/AGCTT | HindIII<br>HindII sold under the trademark HindIII-HF® |
| AAT/ATT | SspI<br>SspI sold under the trademark SspI-HF® |
| /AATT | MluCI<br>Tsp509I |
| A/CATGT | PciI |
| A/CCGGT | AgeI<br>AgeI sold under the trademark AgeI-HF® |
| ACCTGC(4/8) | BspMI<br>BfuAI |
| A/CCWGGT | SexAI |
| A/CGCGT | MluI<br>MluI sold under the trademark MluI-HF® |
| ACGGC(12/14) | BceAI |
| A/CGT | HpvCH4IV |
| ACN/GT | HpvCH4III |
| (10/15)ACNNNNNGTAYC(12/7)<br>(SEQ ID NO: 5) | BaeI |
| (9/12)ACNNNNNCTCC(10/7)<br>(SEQ ID NO: 6) | BsaXI |
| A/CRYGT | AflIII |
| A/CTAGT | SpeI<br>SpeI sold under the trademark SpeI-HF® |
| ACTGG(1/-1) | BsrI |
| ACTGGG(5/4) | BmrI |
| A/GATCT | BglII |
| AGC/GCT | AfeI |
| AG/CT | AluI |
| AGG/CCT | StuI |
| AGT/ACT | ScaI<br>ScaI sold under the trademark ScaI-HF® |
| AT/CGAT | ClaI<br>BspDI |
| ATCTATGTCGGGTGCGGAGAAAGAGG<br>TAAT(-15/-19)<br>(SEQ ID NO: 7) | PI-SceI |
| ATGCA/T | NsiI<br>NsiI sold under the trademark NsiI-HF® |
| AT/TAAT | AseI |
| ATTT/AAAT | SwaI |
| (11/13)CAANNNNNGTGG(12/10)<br>(SEQ ID NO: 8) | CspCI |
| C/AATTG | MfeI<br>MfeI sold under the trademark MfeI-HF® |
| CACGAG(-5/-1) | BssSI<br>BssSαI |
| CACGAG | Nb.BssSI |

| Recognition Sequence | Enzyme |
| --- | --- |
| CACGTC(-3/-3) | BmgBI |
| CAC/GTG | PmlI |
| CACNNN/GTG | DraIII<br>DraIII sold under the trademark DraIII-HF® |
| CACNN/NNGTG<br>(SEQ ID NO: 9) | AleI |
| CAGCAG(25/27) | EcoP15I |
| CAG/CTG | PvuII<br>PvuII sold under the trademark PvuII-HF® |
| CAGNNN/CTG | AlwNI |
| CAGTG(2/0) | BtsIMutI |
| NNCASTGNN/ | TspRI |
| CA/TATG | NdeI |
| CATG/ | NlaIII |
| C/ATG | CviAII |
| /CATG | FatI |
| CAYNN/NNRTG<br>(SEQ ID NO: 10) | MslI |
| CC(12/16) | FspEI |
| CCANNNNN/NNNNTGG<br>(SEQ ID NO: 11) | XcmI |
| CCANNNNN/NTGG<br>(SEQ ID NO: 12) | BstXI |
| CCANNNN/NTGG<br>(SEQ ID NO: 13) | PflMI |
| CCATC(4/5) | BccI |
| C/CATGG | NcoI<br>NcoI sold under the trademark NcoI-HF® |
| CCCAGC(-5/-1) | BseYI |
| CCCGC(4/6) | FauI |
| CCC/GGG | SmaI |
| C/CCGGG | XmaI<br>TspMI |
| (0/-1)CCD | Nt.CviPII |
| CCDG(10/14) | LpnPI |
| CCGC(-3/-1) | AciI |
| CCGC/GG | SacII |
| CCGCTC(-3/-3) | BsrBI |
| C/CGG | MspI<br>HpaII |
| CC/NGG | ScrFI |
| /CCNGG | BssKI<br>StvD4I |
| C/CNNGG | BsaJI |
| CCNNNNN/NNGG<br>(SEQ ID NO: 14) | BslI |
| C/CRYGG | BtgI |
| CC/SGG | NciI |
| C/CTAGG | AvrII |
| CCTC(7/6) | MnlI |
| CCTCAGC(-5/-2) | BbvCI |
| CCTCAGC | Nb.BbvCI |
| CCTCAGC(-5/-7) | Nt.BbvCI |
| CCTGCA/GG | SbfI<br>SbfI sold under the trademark SbfI-HF® |
| CCTNAGC(-5/-2) | Bpu10I |
| CC/TNAGG | Bsu36I |
| CCTNN/NNNAGG<br>(SEQ ID NO: 15) | EcoNI |
| CCTTC(6/5) | HpyAV |
| CC/WGG | BstNI |
| /CCWGG | PsoGI |
| C/CWWGG | StyI<br>StyI sold under the trademark StyI-HF® |
| (10/12)CGANNNNNNTGC(12/10)<br>(SEQ ID NO: 16) | BcgI |
| CGAT/CG | PvuI<br>PvuI sold under the trademark PvuI-HF® |
| CG/CG | BstUI |
| C/GGCCG | EagI<br>EagI sold under the trademark EagI-HF® |
| CG/GWCCG | RsrII |
| CGRY/CG | BsiEI |
| C/GTACG | BsiWI<br>BsiWI sold under the trademark BsiWI-HF® |
| CGTCTC(1/5) | BsmBI |
| CGWCG/ | Hdv99I |
| CMG/CKG | MspAlI |
| CNNR(9/13) | MspJI |
| CR/CCGGYG | SgrAI |
| C/TAG | BfaI |
| CTCAG(9/7) | BsdCNI |

| Recognition Sequence | Enzyme |
| --- | --- |
| C/TCGAG | XhoI<br>PaeR7I<br>TliI |
| CTCTTC(1/4) | EarI |
| CTGAAG(16/14) | AcuI |
| CTGCA/G | PstI<br>PstI sold under the trademark PstI-HF® |
| CTGGAG(16/14) | BpmI |
| C/TNAG | DdeI |
| C/TRYAG | SfcI |
| C/TTAAG | AflII |
| CTTGAG(16/14) | BpuEI |
| C/TYRAG | SmlI |
| C/YCGRG | AvaI<br>BsoBI |
| GAAGA(8/7) | MboII |
| GAAGAC(2/6) | BbsI<br>BbsI sold under the trademark BbsI-HF® |
| GAANN/NNTTC<br>(SEQ ID NO: 17) | XmnI |
| GAATGC(1/-1) | BsmI |
| GAATGC | Nb.BsmI |
| G/AATTC | EcoRI<br>EcoRI sold under the trademark EcoRI-HF® |
| GACGC(5/10) | HgaI |
| GACGT/C | AatII |
| GAC/GTC | ZraI |
| GACN/NNGTC | Tth111I<br>PflFI |
| GACNN/NNGTC<br>(SEQ ID NO: 18) | PshAI |
| GACNNN/NNGTC<br>(SEQ ID NO: 19) | AhdI |
| GACNNNN/NNGTC<br>(SEQ ID NO: 20) | DrdI |
| GAG/CTC | Eco53kI |
| GAGCT/C | SacI<br>SacI sold under the trademark SacI-HF® |
| GAGGAG(10/8) | BseRI |
| GAGTC(4/5) | PleI |
| GAGTC(4/-5) | Nt.BstNBI |
| GAGTC(5/5) | MlyI |
| G/ANTC | HinfI |
| GAT/ATC | EcoRV<br>EcoRV sold under the trademark EcoRV-HF® |
| /GATC | MboI<br>Sau3AI<br>DpnII<br>BfuCI |
| GA/TC | DpnI |
| GATNN/NNATC<br>(SEQ ID NO: 21) | BsaBI |
| G/AWTC | TfiI |
| GCAATG(2/0) | BsrDI |
| GCAATG | Nb.BsrDI |
| GCAGC(8/12) | BbvI |
| GCAGTG(2/0) | BtsI<br>Btsαl |
| GCAGTG | Nb.BtsI |
| GCANNNN/NTGC<br>(SEQ ID NO: 22) | BstAPI |
| GCATC(5/9) | SfaNI |
| GCATG/C | SphI<br>SphI sold under the trademark SphI-HF® |
| GCCC/GGGC | SrfI |
| GCCGAG(21/19) | NmeAIII |
| GCC/GGC | NaeI |
| G/CCGGC | NgoMIV |
| GCCNNNN/NGGC<br>(SEQ ID NO: 23) | BglI |
| GCGAT/CGC | AsiSI |
| GCGATG(10/14) | BtgZI |
| G/CGC | HinP1I |
| GCG/C | HhaI |
| G/CGCGC | BssHII |
| GC/GGCCGC | NotI<br>NotI sold under the trademark NotI-HF® |
| GC/NGC | Fnu4HI |
| GCN/NGC | Cac8I |
| GCNNNNN/NNGC<br>(SEQ ID NO: 24) | MwoI |
| G/CTAGC | NheI<br>NheI sold under the trademark NheI-HF® |
| GCTAG/C | BmtI<br>BmtI sold under the trademark BmtI-HF® |

| Recognition Sequence | Enzyme |
| --- | --- |
| GCTCTTC(1/4) | SapI |
| | BspQI |
| GCTCTTC(1/-7) | Nt.BspQI |
| GC/TNAGC | BlpI |
| G/CWGC | TseI |
| | ApeKI |
| GDGCH/C | Bsp1286I |
| GGATC(4/5) | AlwI |
| GGATC(4/-5) | Nt.AlwI |
| G/GATCC | BamHI |
| | BamHI sold under the trademark BamHI-HF® |
| GGATG(9/13) | FokI |
| GGATG(2/0) | BtsCI |
| GG/CC | HaeIII |
| | PhoI |
| GGCCGG/CC | FseI |
| GGCCNNNN/NGGCC (SEQ ID NO: 25) | SfiI |
| GG/CGCC | NarI |
| G/GCGCC | KasI |
| GGC/GCC | SfoI |
| GGCGC/C | PluTI |
| GG/CGCGCC | AscI |
| GGCGGA(11/9) | EciI |
| GGGAC(10/14) | BsmFI |
| GGGCC/C | ApaI |
| G/GGCCC | PspOMI |
| G/GNCC | Sau96I |
| GGN/NCC | NlaIV |
| GGTAC/C | KpnI |
| | KpnI sold under the trademark KpnI-HF® |
| G/GTACC | Acc65I |
| GGTCTC(1/5) | BsaI |
| | BsaI sold under the trademark BsaI-HF® |
| GGTGA(8/7) | HphI |
| G/GTNACC | BstEII |
| | BstEII sold under the trademark BstEII-HF® |
| G/GWCC | AvaII |
| G/GYRCC | BanI |
| GKGCM/C | BaeGI |
| GR/CGYC | BsaHI |
| GRGCY/C | BanII |
| GT/AC | RsaI |
| G/TAC | CviQI |
| GTA/TAC | BstZ17I |
| | BstZ17I sold under the trademark BstZ17I-HF® |
| GTATCC(6/5) | BciVI |
| G/TCGAC | SalI |
| | SalI sold under the trademark SalI-HF® |
| GTCTC(1/-5) | Nt.BsmAI |
| GTCTC(1/5) | BsmAI |
| | BcoDI |
| G/TGCAC | ApaLI |
| GTGCAG(16/14) | BsgI |
| GT/MKAC | AccI |
| GTN/NAC | Hpy166II |
| /GTSAC | Tsp45I |
| GTT/AAC | HpaI |
| GTTT/AAAC | PmeI |
| GTY/RAC | HincII |
| GWGCW/C | BsiHKAI |
| R/AATTY | ApoI |
| | ApoI-HF |
| RCATG/Y | NspI |
| R/CCGGY | BsrFI |
| | BsrFαI |
| R/GATCY | BstYI |
| RGCGC/Y | HaeII |
| RG/CY | CviKI-1 |
| RG/GNCCY | EcoO109I |
| RG/GWCCY | PpuMI |
| TAACTATAACGGTCCTAAGGTAGCGAA(-9/-13) (SEQ ID NO: 26) | I-CeuI |
| TAC/GTA | SnaBI |
| TAGGGATAACAGGGTAAT(9/-13) (SEQ ID NO: 27) | I-SceI |
| T/CATGA | BSpHI |
| T/CCGGA | BspEI |
| TCCRAC(20/18) | MmeI |
| T/CGA | Taqαl |

-continued

| Recognition Sequence | Enzyme |
|---|---|
| TCG/CGA | NruI<br>NruI sold under the trademark NruI-HF® |
| TCN/GA | Hpy188I |
| TC/NNGA | Hpy188III |
| T/CTAGA | XbaI |
| T/GATCA | BclI |
| TG/CA | HpyCH4V |
| TGC/GCA | FspI |
| TGGCAAACAGCTATTATGGGTATTA TGGGT(-13/-17)<br>(SEQ ID NO: 28) | PI-PspI |
| TGG/CCA | MscI |
| T/GTACA | BsrGI<br>BsrGI sold under the trademark BsrGI-HF® |
| T/TAA | MseI |
| TTAAT/TAA | PacI |
| TTA/TAA | PsiI |
| TT/CGAA | BstBI |
| TTT/AAA | DraI |
| VC/TCGAGB | PspXI |
| W/CCGGW | BsaWI |
| YAC/GTR | BsaAI |
| Y/GGCCR | EaeI |

4. The method of claim 1, wherein the plurality of oligonucleotides comprises at least 100,000 oligonucleotides.

5. The method of claim 1, wherein the plurality of oligonucleotides comprises at least 10 billion oligonucleotides.

6. A platform for storing information, the platform comprising:
  a) a computing system comprising at least one processor and instructions executable by the at least one processor to perform operations comprising:
    i) receiving at least one item of information in a form of at least one digital sequence;
    ii) receiving instructions for enzymatic bioencryption; and
    iii) converting the at least one digital sequence to digital sequences of a plurality of oligonucleotides based on the instructions, wherein the digital sequences of the plurality of oligonucleotides are configured for decryption by exposure of the plurality of oligonucleotides to a nuclease complex; and
  b) a material deposition system for deposition and storage of oligonucleotides comprising:
    i) a synthesizer for receiving instructions from the computing system for synthesizing the plurality of oligonucleotides,
    wherein the synthesizer comprises a substrate for storing the plurality of oligonucleotides.

7. The method of claim 1, wherein the decryption comprises contacting the plurality of oligonucleotides with Cas nuclease (CRISPR-associated nuclease), a Zinc Finger Nuclease (ZFN), a Transcription Activator-Like Effector Nuclease, an Argonaute nuclease, Si Nuclease, a mung bean nuclease, or a DNAse.

8. The method of claim 1, wherein the method further comprises sequencing the plurality of oligonucleotides.

9. The method of claim 1, wherein the plurality of oligonucleotides is stored ex-vivo.

10. The method of claim 1, wherein synthesizing the plurality of oligonucleotides comprises phosphoramidite chemical synthesis.

11. The method of claim 1, wherein the at least one digital sequence comprises at least 1 MB.

12. The platform of claim 6, wherein the decryption comprises contacting the plurality of oligonucleotides with Cas nuclease (CRISPR associated), a Zinc Finger Nuclease (ZFN), a Transcription Activator-Like Effector Nuclease, an Argonaute nuclease, Si Nuclease, a mung bean nuclease, or a DNAse.

13. The platform of claim 6, wherein the computing system comprises a distributed computing system.

* * * * *